(12) United States Patent
Steen et al.

(10) Patent No.: US 11,243,192 B2
(45) Date of Patent: Feb. 8, 2022

(54) 3-D GLASS PRINTABLE HAND-HELD GAS CHROMATOGRAPH FOR BIOMEDICAL AND ENVIRONMENTAL APPLICATIONS

(71) Applicant: VAON, LLC, Bowling Green, KY (US)

(72) Inventors: Henry Steen, Bowling Green, KY (US); Vladimir Dobrokhotov, Bowling Green, KY (US); Quentin Lineberry, Bowling Green, KY (US); Jon Paschal, Bowling Green, KY (US)

(73) Assignee: VAON, LLC, Bowling Green, KY (US)

( * ) Notice: Subject to any disclaimer, the term of this patent is extended or adjusted under 35 U.S.C. 154(b) by 0 days.

(21) Appl. No.: 17/202,026

(22) Filed: Mar. 15, 2021

(65) Prior Publication Data
US 2021/0199627 A1 Jul. 1, 2021

Related U.S. Application Data

(63) Continuation-in-part of application No. 17/001,672, filed on Aug. 24, 2020, which is a
(Continued)

(51) Int. Cl.
*G01N 30/60* (2006.01)
*G01N 30/30* (2006.01)
(Continued)

(52) U.S. Cl.
CPC .............. *G01N 30/30* (2013.01); *G01N 30/20* (2013.01); *G01N 30/32* (2013.01);
(Continued)

(58) Field of Classification Search
CPC ........................ G01N 30/60; G01N 2030/025
See application file for complete search history.

(56) References Cited

U.S. PATENT DOCUMENTS 4,555,383 A * 11/1985 Hall ....................... G01N 30/64
324/449
4,905,498 A * 3/1990 O'Donnell ........... B60K 28/066
180/272

(Continued)

*Primary Examiner* — Lisa M Caputo
*Assistant Examiner* — Alex T Devito
(74) *Attorney, Agent, or Firm* — Hollowell Patent Group; Kelly Hollowell

(57) ABSTRACT

A sensor structure is disclosed comprising at least four planar layers subsuming at least one cavity housed but not contained by overlapping apertures through at least two of the planar layers, wherein the at least one cavity comprises a plurality of chambers, and wherein at least one chamber of the plurality of chambers is configured to be in fluid coupling with at least one other chamber. The plurality of chambers may be defined by overlapping apertures through a plurality of the planar layers. The plurality of chambers may include a Gas Chromatograph (GC) column. The planar layers may be flexible flat glass. The planar layers may be fused together. The layers may be made with apertures through the layers disposed in a desired pattern to define complex structures by the apertures overlapping between abutting layers when the layers are stacked. The planar layers may be configured to admit ultraviolet light.

23 Claims, 44 Drawing Sheets

Related U.S. Application Data continuation-in-part of application No. 16/413,398, filed on May 15, 2019, now Pat. No. 10,821,707, and a continuation-in-part of application No. 15/907,410, filed on Feb. 28, 2018, now Pat. No. 10,802,008, and a continuation-in-part of application No. 15/717,581, filed on Sep. 27, 2017, now abandoned.

(60) Provisional application No. 63/129,732, filed on Dec. 23, 2020, provisional application No. 62/993,396, filed on Mar. 23, 2020, provisional application No. 62/990,397, filed on Mar. 16, 2020, provisional application No. 62/672,735, filed on May 17, 2018, provisional application No. 62/464,629, filed on Feb. 28, 2017, provisional application No. 62/400,152, filed on Sep. 27, 2016.

(51) Int. Cl.
*G01N 30/20* (2006.01)
*G01N 30/32* (2006.01)
*G01N 30/02* (2006.01)

(52) U.S. Cl.
CPC ......... *G01N 30/6095* (2013.01); *G01N 30/60* (2013.01); *G01N 2030/025* (2013.01); *G01N 2030/326* (2013.01)

(56) References Cited

U.S. PATENT DOCUMENTS

| | | | |
|---|---|---|---|
| 5,407,136 A * | 4/1995 | West | B41J 2/02 239/589 |
| 5,571,410 A * | 11/1996 | Swedberg | B01L 3/502707 204/451 |
| 6,537,506 B1 * | 3/2003 | Schwalbe | B01F 5/0604 422/129 |
| 2013/0105921 A1 * | 5/2013 | Najafi | G01C 19/574 257/415 |
| 2016/0187307 A1 * | 6/2016 | Jones | B01J 23/462 73/23.42 |
| 2017/0038349 A1 * | 2/2017 | Dessort | G01N 30/6095 |

* cited by examiner

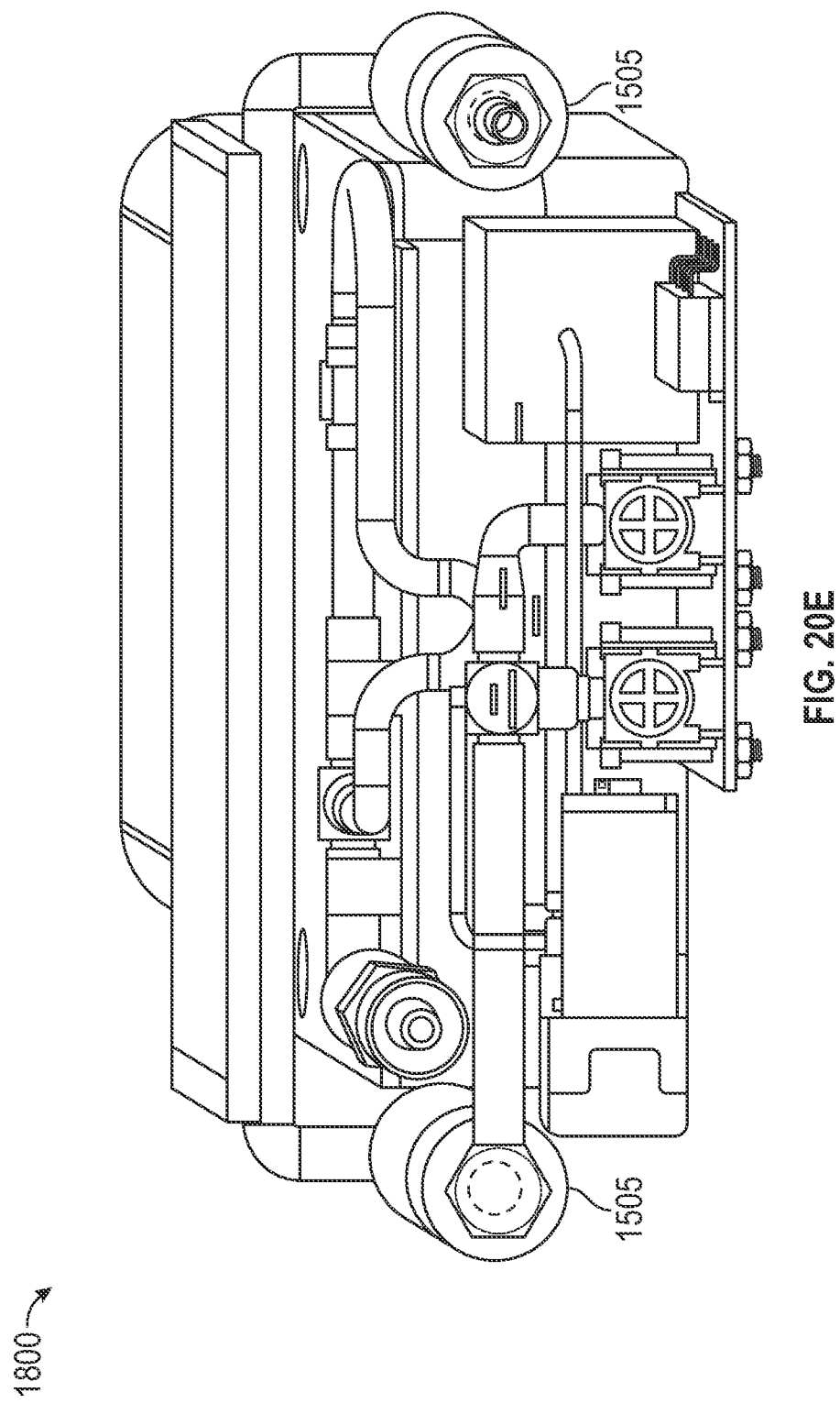

Step 1:
- Breathalyzer power is switched on
- Main pump turns on
- Thermostat heater turns on
- Stationary flow of clean air flows through the sensor

3100

Step 2:
- A human subject blows into the pre-concentrator
- One-way check valves opens up
- VOC molecules get adsorbed by the sorbent material

3115

3100

Step 3:
- Pre-concentrator heats up
- VOCs desorb from sorbent material

3120

3-D GLASS PRINTABLE HAND-HELD GAS CHROMATOGRAPH FOR BIOMEDICAL AND ENVIRONMENTAL APPLICATIONS

CROSS-REFERENCE TO RELATED APPLICATIONS

This application claims benefit of priority to U.S. Provisional Application No. 63/129,732 filed Dec. 23, 2020, U.S. Provisional Application No. 62/993,396 filed Mar. 23, 2020, and U.S. Provisional Application No. 62/990,397 filed Mar. 16, 2020. In addition, this application is also a Continuation-in-Part of U.S. application Ser. No. 17/001,672 filed Aug. 24, 2020, which is a Continuation-in-Part of U.S. application Ser. No. 16/413,398 filed May 15, 2019 (issued as U.S. Pat. No. 10,821,707 on Nov. 3, 2020), which claims priority to Provisional Application No. 62/672,735 filed May 17, 2018. In addition, said U.S. application Ser. No. 17/001,672 filed Aug. 24, 2020, is also a Continuation-in-Part of U.S. application Ser. No. 15/907,410 filed Feb. 28, 2018 (issued as U.S. Pat. No. 10,802,008 on Oct. 13, 2020), which claims priority to Provisional Application No. 62/464,629 filed Feb. 28, 2017. In addition, said U.S. application Ser. No. 17/001,672 filed Aug. 24, 2020, is also a Continuation-in-Part of U.S. application Ser. No. 15/717,581 filed Sep. 27, 2017, which claims priority to Provisional Application No. 62/400,152 filed Sep. 27, 2016. This application incorporates the entire contents of the above-referenced applications herein by reference.

TECHNICAL FIELD

This disclosure relates generally to pathogen identification based on multi-sensor chemical analysis by a portable or hand-held analyzer.

BACKGROUND

A pathogen is an organism that may produce disease. For example, a pathogen may be a virus, or bacteria. Disease produced by some pathogens may be serious. Some pathogens may cause infectious disease enabling contagious infected persons to spread the pathogen. Detecting a pathogen's presence in an infected person may assist effort directed to prevent the pathogen's spread. Identifying a pathogen may help medical treatment of an infected person.

A pathogen may be detected based on analysis of a chemical substance related to the pathogen. For example, some pathogens may directly emit a chemical substance. The body of an infected person may produce or emit a chemical substance resulting from the pathogen infection.

In an illustrative example, chemical analysis to detect or identify a pathogen may require complex and bulky equipment that is expensive, time consuming, and difficult to operate.

Real time field monitoring, which uses a conventional GC with standard sensors (FID, PID, etc.), has a lot of fundamental barriers and limitations, due to its bulky size, heavy weight, special carrier gases requirement and high maintenance. The special carrier gases requirement (bulky gas tanks need to be attached to the instrument for operation) is a major drawback in using conventional chromatography as it limits portability.

Traditionally, in the industrial setting, compact personal monitors and leak detectors are used. These devices are based on an array of electrochemical sensors, equipped with an air intake system, and capable of detecting 2-4 gases in the ppm range. Leak detectors have multiple drawbacks, such as cross-sensitivity between the sensors and an inability to work where complex chemical backgrounds are present. Leak detectors can never provide a user with a comprehensive picture of a volatile organic compound (VOC) sample, such as partial concentrations of benzene, toluene, ethylbenzene, and xylene at ppb levels in the mix. Presently, the only means of analysis is collecting a sample and sending it to a lab, which takes several hours, if not days, to process.

Conventional laboratory gas chromatographs (GCs) are capable of providing a comprehensive analysis of complex VOC samples, but are not suitable for monitoring of VOCs in the field due to their bulky size, heavy weight, special carrier gases requirement, and high maintenance. Another difficulty of implementing conventional GCs in the field conditions is related to the limited capabilities of these instruments to perform in a continuous regime. By continuous regime we imply one cycle of analysis every 20 min, making it 72 scans in 24 hours. Continuous monitoring is especially important for monitoring of VOCs in metropolitan areas, since the concentration of volatile pollutants in the air may vary by orders of magnitude during the day mainly due to traffic.

Typically, conventional gas chromatographs fail to operate at this capacity mainly because PID and FID detectors are not designed for such a frequent use. At the rate of three scans per hour, PID/FID detectors consume 40-50 liters of carrier gas per week. In addition, the use of PID/FID detectors in the field is quite different from the laboratory environment and cause frequent contaminations and drop in sensitivity. This concerns both industrial hygiene and occupational safety applications as well as the non-industrial applications, such as the monitoring of VOCs in big cities primarily caused by vehicles. As a result, a conventional GC in the field would require frequent calibrations and verifications by a trained specialist. On a long run, frequent use would cause a failure of PID/FID detectors within 2-3 months.

SUMMARY

The present disclosure describes the design and operation of an analyzer configured to identify a pathogen based on multi-sensor chemical analysis. The analyzer may include an analytical Gas Chromatograph (GC). The analyzer may be portable. The analyzer may be hand-held. By utilizing scrubbed ambient air as carrier gas, and using 3-D printing glass/metal technology or punctuated layered glass technology for the gas delivery and separation system of the GC, the size and weight of the device can be reduced by orders of magnitude. Various implementations may be designed with a combination of 3-D printing glass/metal technology and punctuated layered glass technology. Some implementations of punctuated layered glass structural technology may construct complex functional devices within a 3D structure. A 3D structure formed with punctuated layered glass technology may include a plurality of chambers defined by overlapping apertures through a plurality of abutting planar layers that form the 3D structure. The planar layers may be made with apertures through the layers disposed in desired patterns to define complex structures by the apertures overlapping between abutting layers when the layers are stacked. Some implementations in accordance with the present disclosure may be a universal compact hand-held analytical GC suitable for industrial and non-industrial applications with high selectivity, low limit Volatile Organic Compound (VOC) detection, rapid analysis cycle time, relatively low cost, and low maintenance. An exemplary implementation in accordance with the present disclosure may advantageously provide lab-quality analysis instantly in the field and, hence, has a wide range of possible applications. Various implementations according to the present disclosure may further comprise an analysis cycle having multiple stages or phases.

Herein disclosed is a sensing device capable to detect volatile organic compounds (VOCs, i.e., scents or odors) emanating from skin or exhaled breath, saliva, and different oral tissues from the oral cavity. Various implementations of the disclosed sensing device are capable to associate VOC patterns to patients with symptomatic and asymptomatic COVID-19. Implementations according to the disclosure can actively detect VOCs from skin and oral cavities of COVID-19 patients, without being invasive, or affecting the integrity of the skin and oral cavity. A design according to the disclosure may be implemented for detection, diagnosis, prediction, and monitoring of COVID-19 in clinical, community or applied settings. Various implementations may complement traditional virus and antibody detection to monitor the onset, progression, and resolution of COVID-19. Implementations according to the disclosure are envisioned to be used in a hospital, clinic setting, community, or even home and workplace.

For example, instead of taking temperatures at entrances to establishments, an implementation according to the disclosure may be used for more informative and accurate data. The danger of contamination is minimal as the disclosed design will probe the skin with minimal to no potential exposure to the virus. In addition, the key substrate for the invention are VOCs, i.e., scents or odors emanating through skin, which are easier to standardize with, at least, two ways to account for person-to-person differences in skin permeability, namely Total Evaporative Water Loss (TEWL) or skin impedance.

The oral cavity provides another alternative for VOC detection by the invention because it is readily accessible. For example, exhaled breath could be captured and analyzed for direct detection of the respiratory tract infection from unique volatile organic metabolite byproducts of SARS-CoV2 infection. VOCs from skin and oral cavity offer opportunities for continuous (i.e., wearable) or periodic monitoring of viral infection and disease presentation. The invention can be used to measure VOCs on skin and/or oral cavity, subsequently correlating those VOC patterns with COVID-19 signatures through AI/machine learning. This quick screening device would enable doctors to detect and diagnose COVID-19 symptomatic and asymptomatic individuals leading to appropriate treatment and/or quarantine procedures.

Additionally, implementations according to the disclosure may be able to differentiate between COVID-negative and COVID-positive-asymptomatic subjects. At the London School of Hygiene and Tropical Diseases, dogs are being trained to detect the scent of potential COVID-19 patients. This is possible because the dog's olfactory system contains 300 million receptors whereas the human nose has only 5 million receptors. The disclosed design mimics the biological sense of smell with a more robust, standardized, and mechanized approach. In the long run, the disclosed design is not limited to COVID-19 diagnosis, and can be readily adapted to other pandemics, as well as for the detection of other diseases and conditions.

In one embodiment, an implementation according to the present disclosure is a Multisensory Gas Chromatography (MGC) device and method of making a GC/Enose hybrid detector for diagnosis of diseases. Therefore, in one implementation, the present disclosure provides a portable lab that can be man-carried to any location for rapid diagnostics of infectious diseases in the field, at sea or abroad. The device is a compact and robust battery-powered analytical instrument for analysis of complex multicomponent mixtures of volatile organic compounds ("VOCs") emanated from bacteria. The device is based on principles of analytical gas chromatography ("GC") and uses a novel highly integrated multisensory detector, also known as electronic nose or Enose.

The sensors in the disclosed micro-electrical mechanical system, ("MEMS") integrated platform are near-orthogonal and possess very distinct catalytic properties. Hence, the time separation by chromatographic column can be complemented by the catalytic separation of a multisensory detector. The outcome of combining these technologies is GC/Enose hybrid technology, also referred to herein as Multisensory Gas Chromatography (MGC) which has the ability to monitor a very broad range of analytes from light to heavy on a relatively short and compact GC column in a short period of time of about 12.5 min. Also, the device can perform the analysis in a broad range of concentrations from sub-ppb to 100% for most of the analytes of interest.

Standard technology chromatograms are obtained from cultured bacteria. Using the multisensory detector, the present device collects multiple chromatograms in a single run providing rapid diagnostic of the infectious disease. More specifically, due to the quick response and recovery of the unique multisensory detector, VOC chemicals are separated in time as individual peaks. Because of the quasi-orthogonality of sensors in the array, the integrated electronic signature (combination of signals from 4 sensors) is unique for each of the analytes. By combining time separation, using a chromatography column with chemical separation (by catalytic reactivity), and using a quasi-orthogonal array of sensors, a substantially more comprehensive analysis of a gas mixtures, can be then obtained. That is, by utilizing 4 very different sensory elements in one detector, 4 chromatograms are obtained in a single analysis cycle, adding another dimension to the separation and recognition of chemicals providing a new diagnostic tool for rapidly identifying infectious diseases in remote locations.

These and other advantages of the invention will be further understood and appreciated by those skilled in the art by reference to the following written specification, claims and appended drawings.

Apparatus and associated methods relate to a portable pathogen identification lab configured with a Gas Chromatograph (GC) column and a multisensory detector to identify a pathogen of interest. The pathogen of interest may be identified based on detecting a substance in collected gases and vapors emitted directly by the pathogen. The portable pathogen identification lab includes pumps, valves, and a heater configured to separate a test sample retained by the GC column into a plurality of component analytes, generate a test sample electronic signature determined from captured sensor signals combined as a function of time, identify the test sample electronic signature based on associating the test sample electronic signature with a predetermined reference sample signature generated based on collected gases and vapors produced by the pathogen, and separating a plurality of chromatograph peaks using sensor response differences determined as a function of catalytic reactivity diversity between the multisensory detector sensors.

In an aspect, an apparatus may comprise: at least four planar layers comprising at least one cavity housed but not contained by overlapping apertures through at least two of the planar layers, wherein the at least one cavity comprises a plurality of chambers and a Gas Chromatograph (GC) column, wherein at least one chamber of the plurality of chambers is configured to be in fluid coupling with at least one other chamber of the plurality of chambers, wherein at least one chamber of the plurality of chambers is configured to be in fluid coupling with the GC column, and wherein at least one chamber of the plurality of chambers comprises a pre-concentrator in fluid communication with a sampling pump fluidly coupled with a sampling port fluidly coupled with a collection device configured to collect gases and vapors emitted by a pathogen in the collection device; a processor; at least one valve operably coupled with the processor, wherein the at least one valve is configured when operated to govern fluid coupling interchangeable between a coupled and an uncoupled state among at least one chamber and the GC column; at least one pump operably coupled with the processor, wherein the at least one pump is configured when activated to pump fluid between at least one chamber and the GC column; at least one heater operably coupled with the processor, wherein the at least one heater is configured when activated to heat at least a portion of the at least one cavity; a plurality of sensors operably coupled with the processor, wherein each sensor of the plurality of sensors is disposed in one chamber of the plurality of chambers, and wherein each sensor is distinctly configured to measure a physical quantity of at least one chemical component of a fluid chemical component sample, wherein each sensor has a different response characteristic than each of the other sensors of the plurality of sensors, and to communicate the measured physical quantity of the at least one chemical component to the processor as a sensor signal understandable by the processor; and a memory configured to be operably coupled to the processor, wherein the memory comprises encoded processor executable program instructions and data, wherein said instructions and data program and configure the processor that when executed by the processor cause the apparatus to perform operations comprising: separate a fluid test sample comprising at least one chemical component retained by the GC column into at least one chemical component analyte, wherein when separated at least a portion of each chemical component analyte is substantially retained by one chamber of the plurality of chambers, based on operating the at least one valve in combination with activating the at least one pump and activating the at least one heater to separate a desorbed test sample in the GC column while capturing a sensor signal from each sensor of the plurality of sensors for at least a predetermined capture time period; and generate a test sample electronic signature determined based on the plurality of captured sensor signals combined as a function of time over at least a portion of the sensor signal capture time period; and identify the test sample electronic signature based on associating the test sample electronic signature with a predetermined reference sample signature generated as a function of collected gases and vapors produced by a pathogen.

The gases and vapors may further comprise VOCs.

The collection device configured to collect VOCs produced by a pathogen may further comprise a Petri dish.

The pathogen may further comprise bacteria.

The pathogen may further comprise virus.

The VOCs may further comprise a pathogen metabolite emitted by the pathogen into the device configured to collect gases and vapors.

Separate the test sample may further comprise inject the desorbed sample into the GC column.

The sensor signal capture time period may be determined as a function of at least one component analyte's retention time on the GC column, and wherein the retention time is determined as a function of at least one captured sensor signal.

The plurality of sensors may further comprise a thermal conductivity detector (TCD).

The plurality of sensors may further comprise a dual oxide $SnO_2$/CuO sensor.

The plurality of sensors may further comprise an Au/Pd bimetal nanoparticle metal oxide sensor.

The plurality of sensors may further comprise an unmodified $SnO_2$ sensor.

The at least one heater may be operably coupled with the processor wherein the heater is activated when one or more sensor is active, and wherein the one or more sensor is operably coupled with the processor.

In some implementations, the at least one heater may be directly controlled by the processor.

In some implementations, the at least one heater may not be directly controlled by the processor. In an implementation wherein the at least one heater is not directly controlled by the processor, the at least one heater may be configured to be activated when one or more sensor is active.

The test sample electronic signature may further comprise a plurality of chromatograms having data peaks separated based on different sensor measurement response characteristics of each sensor of the plurality of sensors.

The different response characteristics of the plurality of sensors may be based on differences in catalytic reactivity between each sensor of the plurality of sensors.

The different response characteristics of the plurality of sensors may be a result of sensor measurement response time diversity due to different chemical reaction rates by the sensors with the chemical component quantity each sensor is configured to measure.

At least one of the planar layers may be flexible flat glass.

In another aspect, an apparatus may comprise: at least four planar layers comprising at least one cavity housed but not contained by overlapping apertures through at least two of the planar layers, wherein the at least one cavity comprises a plurality of chambers defined by overlapping apertures through a plurality of the planar layers and a Gas Chromatograph (GC) column defined by overlapping apertures through a plurality of the planar layers, wherein at least one chamber of the plurality of chambers is configured to be in fluid coupling with at least one other chamber of the plurality of chambers, wherein at least one chamber of the plurality of chambers is configured to be in fluid coupling with the GC column, wherein at least one chamber of the plurality of chambers comprises a pre-concentrator configured to be in fluid communication with a sampling pump, wherein the sampling pump is configured to be fluidly coupled with a sampling port that is fluidly coupled with a collection device configured to collect gases and vapors emitted by a pathogen in the collection device, and wherein at least one chamber of the plurality of chambers comprises a scrubber configured to be fluidly coupled with the GC column and the environment to inject scrubbed air carrier gas into the GC column; a processor; at least one valve operably coupled with the processor, wherein the at least one valve is configured when operated to selectively govern fluid coupling interchangeable between a coupled and an uncoupled state among at least one chamber of the plurality of chambers and the GC column; at least one pump operably coupled with the processor, wherein the at least one pump is configured when activated to selectively pump fluid between at least one chamber of the plurality of chambers and the GC column; at least one heater operably coupled with the processor, wherein the at least one heater is configured when activated to selectively heat at least a portion of the at least one cavity, the plurality of chambers, the pre-concentrator, and the GC column; a plurality of sensors operably coupled with the processor, wherein each sensor of the plurality of sensors is disposed in one chamber of the plurality of chambers, wherein each sensor is distinctly configured to measure a physical quantity of at least one chemical component of a fluid chemical component sample, wherein each sensor has a different response characteristic than each of the other sensors of the plurality of sensors, wherein the different response characteristics of the plurality of sensors are based on differences in catalytic reactivity between each sensor of the plurality of sensors, and to communicate the measured physical quantity of the at least one chemical component to the processor as a sensor signal understandable by the processor, and wherein the plurality of sensors comprises: a thermal conductivity detector (TCD), a dual oxide $SnO_2/CuO$ sensor, a Au/Pd bimetal nanoparticle metal oxide sensor, and an unmodified $SnO_2$ sensor; and a memory configured to be operably coupled to the processor, wherein the memory comprises encoded processor executable program instructions and data, wherein said instructions and data program and configure the processor that when executed by the processor cause the apparatus to perform operations comprising: separate a fluid test sample comprising at least one chemical component retained by the GC column into at least one chemical component analyte, wherein when separated at least a portion of each chemical component analyte is substantially retained by one chamber of the plurality of chambers, based on operating the at least one valve in combination with activating the at least one pump and activating the at least one heater to separate a desorbed test sample comprising scrubbed air carrier gas in the GC column while capturing a sensor signal from each sensor of the plurality of sensors for at least a predetermined capture time period; and generate a test sample electronic signature determined based on the plurality of captured sensor signals combined as a function of time over at least a portion of the sensor signal capture time period, wherein the capture time period is based on the retention time, determined as a function of the plurality of captured sensor signals, of the heaviest analyte in the sample on the GC column; purge the pre-concentrator and GC column with scrubbed air; and identify the test sample electronic signature based on associating the test sample electronic signature with a predetermined reference sample signature generated as a function of collected gases and vapors produced by a pathogen.

The plurality of sensors may be configured in a quasi-orthogonal array.

Associating the test sample electronic signature may further comprise pattern recognition.

Associating the test sample electronic signature may further comprise separating a plurality of data point clouds determined as a function of a plurality of pathogen gas and vapor exposure patterns.

The pathogen may further comprise a coronavirus.

At least one of the planar layers may be flat glass.

In another aspect, an apparatus may comprise: at least four planar layers comprising at least one cavity housed but not contained by overlapping apertures through at least two of the planar layers, wherein the at least one cavity comprises a plurality of chambers defined by overlapping apertures through a plurality of the planar layers and a Gas Chromatograph (GC) column defined by overlapping apertures through a plurality of the planar layers, wherein at least one chamber of the plurality of chambers is configured to be in fluid coupling with at least one other chamber of the plurality of chambers, wherein at least one chamber of the plurality of chambers is configured to be in fluid coupling with the GC column, wherein at least one chamber of the plurality of chambers comprises a pre-concentrator configured to be in fluid communication with a sampling pump, wherein the sampling pump is configured to be fluidly coupled with a sampling port that is fluidly coupled with a collection device configured to collect gases and vapors emitted by a pathogen comprising a coronavirus in the collection device, and wherein at least one chamber of the plurality of chambers comprises a scrubber configured to be fluidly coupled with the GC column and the environment to selectively inject scrubbed air carrier gas into the GC column and the pre-concentrator; a processor; at least one valve operably coupled with the processor, wherein the at least one valve is configured when operated to selectively govern fluid coupling interchangeable between a coupled and an uncoupled state among at least one chamber of the plurality of chambers and the GC column; at least one pump operably coupled with the processor, wherein the at least one pump is configured when activated to selectively pump fluid between at least one chamber of the plurality of chambers and the GC column; at least one heater operably coupled with the processor, wherein the at least one heater is configured when activated to selectively heat at least a portion of the at least one cavity, the plurality of chambers, the pre-concentrator, and the GC column; a plurality of sensors operably coupled with the processor, wherein each sensor of the plurality of sensors is disposed in one chamber of the plurality of chambers, wherein each sensor is distinctly configured to measure a physical quantity of at least one chemical component of a fluid chemical component sample, wherein each sensor has a different response characteristic than each of the other sensors of the plurality of sensors, wherein the different response characteristics of the plurality of sensors are based on differences in catalytic reactivity between each sensor of the plurality of sensors, and to communicate the measured physical quantity of the at least one chemical component to the processor as a sensor signal understandable by the processor, wherein the plurality of sensors comprises: a thermal conductivity detector (TCD), a dual oxide $SnO2/CuO$ sensor, a Au/Pd bimetal nanoparticle metal oxide sensor, and an unmodified $SnO2$ sensor, and wherein the plurality of sensors are configured in a quasi-orthogonal array; and a memory configured to be operably coupled to the processor, wherein the memory comprises encoded processor executable program instructions and data, wherein said instructions and data program and configure the processor that when executed by the processor cause the apparatus to perform operations comprising: separate a fluid test sample comprising at least one chemical component retained by the GC column into at least one component analyte, wherein when separated at least a portion of each chemical component analyte is substantially retained by one chamber of the plurality of chambers, based on operating the at least one valve in combination with activating the at least one pump and activating the at least one heater to separate a desorbed test sample comprising scrubbed air carrier gas in the GC column while capturing a sensor signal from each sensor of the plurality of sensors for at least a predetermined capture time period; and generate a test sample electronic signature determined based on the plurality of captured sensor signals combined as a function of time over at least a portion of the sensor signal capture time period, wherein the capture time period is based on the retention time, determined as a function of the plurality of captured sensor signals, of the heaviest analyte in the sample on the GC column; purge the pre-concentrator and GC column with scrubbed air; and identify the test sample electronic signature based on associating the test sample electronic signature with a predetermined reference sample signature generated as a function of collected gases and vapors produced by a pathogen comprising a coronavirus, based on separating a plurality of data point clouds determined as a function of a plurality of pathogen exposure patterns.

The apparatus may further comprise a portable lab.

The portable lab may be hand-held.

The apparatus may further comprise at least one layer configured to admit ultraviolet (UV) light into at least one chamber of the plurality of chambers.

The apparatus may further comprise a user interface operably coupled with the processor, and the operations performed by the apparatus may further comprise indicate the identified test sample to a user via the user interface.

The coronavirus may further comprise COVID-19.

At least one of the planar layers may be glass.

In an aspect, an apparatus may comprise: a processor; at least one chamber; a plurality of sensors operably coupled with the processor, wherein each sensor of the plurality of sensors is disposed in one chamber, and wherein each sensor is distinctly configured to measure a physical quantity of at least one chemical component of a fluid chemical component sample, wherein each sensor has a different response characteristic than each of the other sensors of the plurality of sensors, and wherein each sensor of the plurality of sensors is configured that when the sensor is activated, the sensor communicates the measured physical quantity of the at least one chemical component to the processor as a sensor signal understandable by the processor; at least one valve operably coupled with the processor and configured to be fluidly coupled with at least one chamber; at least one pump operably coupled with the processor and configured to be fluidly coupled with at least one chamber; at least one heater configured to be activated when at least one sensor is active, wherein the at least one heater is configured that when activated the at least one heater heats at least a portion of at least one chamber; and a memory configured to be operably coupled to the processor, wherein the memory comprises encoded processor executable program instructions and data, wherein said instructions and data program configure the processor that when executed by the processor cause the apparatus to perform operations.

The operations performed by the apparatus may further comprise: construct a chromatogram combining retention time separation data and catalytic separation data for a chemical component test sample substantially retained by at least one chamber; generate a test sample electronic signature determined as a function of the combined chromatogram; and identify a pathogen of interest in the test sample based on associating the test sample electronic signature with a predetermined reference sample signature.

The apparatus may further comprise at least one chamber comprising a Gas Chromatograph (GC) column.

The apparatus may further comprise a GC.

At least one chamber may be defined by a structure comprising: at least four planar layers comprising at least one cavity housed but not contained by overlapping apertures through at least two of the planar layers.

Construct the chromatogram combining retention time separation data and catalytic separation data may further comprise operating the at least one valve in combination with activating the at least one pump and activating at least one sensor to separate the test sample while capturing a sensor signal from each sensor of the plurality of sensors.

The different response characteristics of the plurality of sensors may be based on differences in catalytic reactivity between each sensor of the plurality of sensors, and wherein the test sample electronic signature further comprises a plurality of chromatograms having data peaks separated based on different response characteristics of each sensor of the plurality of sensors.

The pathogen may further comprise bacteria.

The pathogen may further comprise virus.

The virus may further comprise a coronavirus.

The coronavirus may further comprise COVID-19.

In another aspect an apparatus may comprise: a processor; at least one chamber; a plurality of sensors operably coupled with the processor, wherein each sensor of the plurality of sensors is disposed in one chamber, and wherein each sensor is distinctly configured to measure a physical quantity of at least one chemical component of a fluid chemical component sample, wherein each sensor has a different response characteristic than each of the other sensors of the plurality of sensors, wherein the different response characteristics of the plurality of sensors are based on differences in catalytic reactivity between each sensor of the plurality of sensors, and wherein each sensor of the plurality of sensors is configured that when the sensor is activated, the sensor communicates the measured physical quantity of the at least one chemical component to the processor as a sensor signal understandable by the processor; at least one valve operably coupled with the processor and configured to be fluidly coupled with at least one chamber; at least one pump operably coupled with the processor and configured to be fluidly coupled with at least one chamber; at least one heater configured to be activated when at least one sensor is active, wherein the at least one heater is configured that when activated the at least one heater heats at least a portion of at least one chamber; and a memory configured to be operably coupled to the processor, wherein the memory comprises encoded processor executable program instructions and data, wherein said instructions and data program configure the processor that when executed by the processor cause the apparatus to perform operations comprising: construct a chromatogram combining retention time separation data and catalytic separation data for a chemical component test sample substantially retained by at least one chamber, based on operating the at least one valve in combination with activating the at least one pump and activating the at least one heater to separate the test sample while capturing a sensor signal from each sensor of the plurality of sensors; generate a test sample electronic signature determined as a function of the combined chromatogram; and identify a pathogen of interest in the test sample based on associating the test sample electronic signature with a predetermined reference sample signature generated as a function of a gases and vapors emitted by a pathogen.

The apparatus may further comprise a pre-concentrator configured to be fluidly coupled with at least one chamber.

The apparatus may further comprise a sampling port fluidly coupled with a collection device configured to collect gases and vapors emitted by a pathogen in the collection device.

The pathogen may further comprise bacteria.

The pathogen may further comprise virus.

The virus may further comprise a coronavirus.

The coronavirus may further comprise COVID-19.

In another aspect, an apparatus may comprise: a processor; at least one chamber defined by a structure comprising: at least four planar layers comprising at least one cavity housed but not contained by overlapping apertures through at least two of the planar layers; a pre-concentrator configured to be fluidly coupled with at least one chamber; a sampling port fluidly coupled with at least one chamber and a collection device configured to collect gases and vapors emitted by a pathogen in the collection device; a plurality of sensors operably coupled with the processor, wherein each sensor of the plurality of sensors is disposed in one chamber, and wherein each sensor is distinctly configured to measure a physical quantity of at least one chemical component of a fluid chemical component sample, wherein each sensor has a different response characteristic than each of the other sensors of the plurality of sensors, wherein the different response characteristics of the plurality of sensors are based on differences in catalytic reactivity between each sensor of the plurality of sensors, and wherein each sensor of the plurality of sensors is configured that when the sensor is activated, the sensor communicates the measured physical quantity of the at least one chemical component to the processor as a sensor signal understandable by the processor; at least one valve operably coupled with the processor and configured to be fluidly coupled with at least one chamber; at least one pump operably coupled with the processor and configured to be fluidly coupled with at least one chamber; at least one heater configured to be activated when at least one sensor is active, wherein the at least one heater is configured that when activated the at least one heater heats at least a portion of at least one chamber; and a memory configured to be operably coupled to the processor, wherein the memory comprises encoded processor executable program instructions and data, wherein said instructions and data program configure the processor that when executed by the processor cause the apparatus to perform operations comprising: construct a chromatogram combining retention time separation data and catalytic separation data for a chemical component test sample substantially retained by at least one chamber, based on operating the at least one valve in combination with activating the at least one pump and activating the at least one heater to separate the test sample while capturing a sensor signal from each sensor of the plurality of sensors; generate a test sample electronic signature determined as a function of the combined chromatogram; and identify the test sample based on associating the test sample electronic signature with a predetermined reference sample signature generated as a function of gases and vapors emitted by a pathogen of interest comprising a coronavirus.

The pathogen may further comprise bacteria.

The reference sample may be a single compound, or a number of compounds tested separately, not necessarily a mixture.

The reference sample may be a mixture.

Separate the test sample may further comprise desorb the test sample.

Separate the test sample may further comprise inject the desorbed sample into at least one chamber.

The plurality of sensors may further comprise a thermal conductivity detector (TCD).

The plurality of sensors may further comprise a dual oxide $SnO_2/CuO$ sensor.

The plurality of sensors may further comprise a Au/Pd bimetal nanoparticle metal oxide sensor.

The plurality of sensors may further comprise an unmodified $SnO_2$ sensor.

In an aspect, a method may comprise: constructing, by a Gas Chromatograph (GC), a chromatogram combining retention time separation data and catalytic separation data for a chemical component test sample, wherein the chromatogram combining retention time separation data and catalytic separation data is based on data captured from a plurality of sensors, wherein each sensor is distinctly configured to measure a physical quantity of at least one chemical component of a fluid chemical component test sample, wherein each sensor has a different response characteristic than each of the other sensors of the plurality of sensors, and wherein the different response characteristics of the plurality of sensors are based on differences in catalytic reactivity between each sensor of the plurality of sensors; generating, by a processor, a test sample electronic signature determined as a function of the combined chromatogram; and identifying, by a processor, a pathogen in the test sample based on associating the test sample electronic signature with a predetermined reference sample signature generated as a function of a pathogen of interest.

Identifying the pathogen in the test sample may further comprise identifying the pathogen in the test sample as the pathogen of interest.

The pathogen of interest may further comprise virus.

The virus may further comprise a coronavirus.

Apparatus and associated methods relate to a hand-held breathalyzer configured with a Gas Chromatograph (GC) column and a multisensory detector to identify a pathogen of interest. The pathogen may be identified based on detecting a substance from a test subject's body as gases and vapors in exhaled breath. The breathalyzer includes a mouthpiece, pumps, valves, and a heater configured to separate an exhaled test sample retained by the GC column into a plurality of component analytes, generate a test sample electronic signature determined from captured sensor signals combined as a function of time, identify the test sample electronic signature based on associating the test sample electronic signature with a predetermined reference sample signature generated based on a collected test sample exhaled by a test subject, and separating a plurality of chromatograph peaks using sensor response differences resulting from catalytic reactivity diversity between multisensory detector sensors. The pathogen may be COVID-19.

In an aspect, an apparatus may comprise: at least four planar layers comprising at least one cavity housed but not contained by overlapping apertures through at least two of the planar layers, wherein the at least one cavity comprises a plurality of chambers and a Gas Chromatograph (GC) column, wherein at least one chamber of the plurality of chambers is configured to be in fluid coupling with at least one other chamber of the plurality of chambers, wherein at least one chamber of the plurality of chambers is configured to be in fluid coupling with the GC column, and wherein at least one chamber of the plurality of chambers comprises a pre-concentrator in fluid communication with a sampling port fluidly coupled with a mouthpiece configured to receive in the exhaled breath of the test subject gases and vapors produced in the body of the test subject; a processor; at least one valve operably coupled with the processor, wherein the at least one valve is configured when operated to govern fluid coupling interchangeable between a coupled and an uncoupled state among at least one chamber and the GC column; at least one pump operably coupled with the processor, wherein the at least one pump is configured when activated to pump fluid between at least one chamber and the GC column; at least one heater operably coupled with the processor, wherein the at least one heater is configured when activated to heat at least a portion of the at least one cavity; a plurality of sensors operably coupled with the processor, wherein each sensor of the plurality of sensors is disposed in one chamber of the plurality of chambers, and wherein each sensor is distinctly configured to measure a physical quantity of at least one chemical component of a fluid chemical component sample, wherein each sensor has a different response characteristic than each of the other sensors of the plurality of sensors, and to communicate the measured physical quantity of the at least one chemical component to the processor as a sensor signal understandable by the processor; and a memory configured to be operably coupled to the processor, wherein the memory comprises encoded processor executable program instructions and data, wherein said instructions and data program and configure the processor that when executed by the processor cause the apparatus to perform operations comprising: separate a fluid test sample comprising at least one chemical component retained by the GC column into at least one chemical component analyte, wherein when separated at least a portion of each chemical component analyte is substantially retained by one chamber of the plurality of chambers, based on operating the at least one valve in combination with activating the at least one pump and activating the at least one heater to separate a desorbed test sample in the GC column while capturing a sensor signal from each sensor of the plurality of sensors for at least a predetermined capture time period; and generate a test sample electronic signature determined based on the plurality of captured sensor signals combined as a function of time over at least a portion of the sensor signal capture time period; and identify the test sample electronic signature based on associating the test sample electronic signature with a predetermined reference sample signature generated as a function of gases and vapors in exhaled breath.

The sample may further comprise gases and vapors.

The gases and vapors may further comprise a Volatile Organic Compound (VOC).

The test subject may further comprise a human test subject.

The gases and vapors exhaled by the test subject may further comprise a metabolite released in the test subject's body as a result of a pathogen in the test subject.

The pathogen may further comprise bacteria.

The pathogen may further comprise virus.

Separate the test sample may further comprise inject the desorbed sample into the GC column.

The sensor signal capture time period may be determined as a function of at least one component analyte's retention time on the GC column, and wherein the retention time may be determined as a function of at least one captured sensor signal.

The plurality of sensors may further comprise a thermal conductivity detector (TCD).

The plurality of sensors may further comprise a dual oxide $SnO_2/CuO$ sensor.

The plurality of sensors may further comprise an Au/Pd bimetal nanoparticle metal oxide sensor.

The plurality of sensors may further comprise an unmodified $SnO_2$ sensor.

The test sample electronic signature may further comprise a plurality of chromatograms having data peaks separated based on different response characteristics of each sensor of the plurality of sensors.

The different response characteristics of the plurality of sensors may be based on differences in catalytic reactivity between each sensor of the plurality of sensors.

At least one of the planar layers may be flexible flat glass.

In another aspect, an apparatus may comprise: at least four planar layers comprising at least one cavity housed but not contained by overlapping apertures through at least two of the planar layers, wherein the at least one cavity comprises a plurality of chambers defined by overlapping apertures through a plurality of the planar layers and a Gas Chromatograph (GC) column defined by overlapping apertures through a plurality of the planar layers, wherein at least one chamber of the plurality of chambers is configured to be in fluid coupling with at least one other chamber of the plurality of chambers, wherein at least one chamber of the plurality of chambers is configured to be in fluid coupling with the GC column, wherein at least one chamber of the plurality of chambers comprises a pre-concentrator configured to be in fluid communication with a sampling port fluidly coupled with a mouthpiece configured to receive in the exhaled breath of a test subject comprising gases and vapors produced in the body of the test subject, and wherein at least one chamber of the plurality of chambers comprises a scrubber configured to be fluidly coupled with the GC column and the environment to inject scrubbed air carrier gas into the GC column; a processor; at least one valve operably coupled with the processor, wherein the at least one valve is configured when operated to selectively govern fluid coupling interchangeable between a coupled and an uncoupled state among at least one chamber of the plurality of chambers and the GC column; at least one pump operably coupled with the processor, wherein the at least one pump is configured when activated to selectively pump fluid between at least one chamber of the plurality of chambers and the GC column; at least one heater operably coupled with the processor, wherein the at least one heater is configured when activated to selectively heat at least a portion of the at least one cavity, the plurality of chambers, the pre-concentrator, and the GC column; a plurality of sensors operably coupled with the processor, wherein each sensor of the plurality of sensors is disposed in one chamber of the plurality of chambers, wherein each sensor is distinctly configured to measure a physical quantity of at least one chemical component of a fluid chemical component sample, wherein each sensor has a different response characteristic than each of the other sensors of the plurality of sensors, wherein the different response characteristics of the plurality of sensors are based on differences in catalytic reactivity between each sensor of the plurality of sensors, and to communicate the measured physical quantity of the at least one chemical component to the processor as a sensor signal understandable by the processor, and wherein the plurality of sensors comprises: a thermal conductivity detector (TCD), a dual oxide SnO2/CuO sensor, a Au/Pd bimetal nanoparticle metal oxide sensor, and an unmodified SnO2 sensor; and a memory configured to be operably coupled to the processor, wherein the memory comprises encoded processor executable program instructions and data, wherein said instructions and data program and configure the processor that when executed by the processor cause the apparatus to perform operations comprising: separate a fluid test sample comprising at least one chemical component retained by the GC column into at least one chemical component analyte, wherein when separated at least a portion of each chemical component analyte is substantially retained by one chamber of the plurality of chambers, based on operating the at least one valve in combination with activating the at least one pump and activating the at least one heater to separate a desorbed test sample comprising scrubbed air carrier gas in the GC column while capturing a sensor signal from each sensor of the plurality of sensors for at least a predetermined capture time period; and generate a test sample electronic signature determined based on the plurality of captured sensor signals combined as a function of time over at least a portion of the sensor signal capture time period, wherein the capture time period is based on the retention time, determined as a function of the plurality of captured sensor signals, of the heaviest analyte in the sample on the GC column; purge the pre-concentrator and GC column with scrubbed air; and identify a pathogen in the test sample based on associating the test sample electronic signature with a predetermined reference sample signature generated as a function of gases and vapors in exhaled breath.

The plurality of sensors may be configured in a quasi-orthogonal array.

Associating the test sample electronic signature may further comprise pattern recognition.

Associating the test sample electronic signature may further comprise separating a plurality of data point clouds determined as a function of a plurality of pathogen exposure patterns.

The pathogen may further comprise a coronavirus.

At least one of the planar layers may be flat glass.

In another aspect, an apparatus may comprise: at least four planar layers comprising at least one cavity housed but not contained by overlapping apertures through at least two of the planar layers, wherein the at least one cavity comprises a plurality of chambers defined by overlapping apertures through a plurality of the planar layers and a Gas Chromatograph (GC) column defined by overlapping apertures through a plurality of the planar layers, wherein at least one chamber of the plurality of chambers is configured to be in fluid coupling with at least one other chamber of the plurality of chambers, wherein at least one chamber of the plurality of chambers is configured to be in fluid coupling with the GC column, wherein at least one chamber of the plurality of chambers comprises a pre-concentrator configured to be in fluid communication with a sampling port fluidly coupled with a mouthpiece configured to receive in the exhaled breath of a test subject gases and vapors produced in the body of the test subject, and wherein at least one chamber of the plurality of chambers comprises a scrubber configured to be fluidly coupled with the GC column and the environment to selectively inject scrubbed air carrier gas into the GC column and the pre-concentrator; a processor; at least one valve operably coupled with the processor, wherein the at least one valve is configured when operated to selectively govern fluid coupling interchangeable between a coupled and an uncoupled state among at least one chamber of the plurality of chambers and the GC column; at least one pump operably coupled with the processor, wherein the at least one pump is configured when activated to selectively pump fluid between at least one chamber of the plurality of chambers and the GC column; at least one heater operably coupled with the processor, wherein the at least one heater is configured when activated to selectively heat at least a portion of the at least one cavity, the plurality of chambers, the pre-concentrator, and the GC column; a plurality of sensors operably coupled with the processor, wherein each sensor of the plurality of sensors is disposed in one chamber of the plurality of chambers, wherein each sensor is distinctly configured to measure a physical quantity of at least one chemical component of a fluid chemical component sample, wherein each sensor has a different response characteristic than each of the other sensors of the plurality of sensors, wherein the different response characteristics of the plurality of sensors are based on differences in catalytic reactivity between each sensor of the plurality of sensors, and to communicate the measured physical quantity of the at least one chemical component to the processor as a sensor signal understandable by the processor, wherein the plurality of sensors comprises: a thermal conductivity detector (TCD), a dual oxide $SnO_2/CuO$ sensor, a Au/Pd bimetal nanoparticle metal oxide sensor, and an unmodified $SnO_2$ sensor, and wherein the plurality of sensors are configured in a quasi-orthogonal array; and a memory configured to be operably coupled to the processor, wherein the memory comprises encoded processor executable program instructions and data, wherein said instructions and data program and configure the processor that when executed by the processor cause the apparatus to perform operations comprising: separate a fluid test sample comprising at least one chemical component retained by the GC column into at least one chemical component analyte, wherein when separated at least a portion of each chemical component analyte is substantially retained by one chamber of the plurality of chambers, based on operating the at least one valve in combination with activating the at least one pump and activating the at least one heater to separate a desorbed test sample comprising scrubbed air carrier gas in the GC column while capturing a sensor signal from each sensor of the plurality of sensors for at least a predetermined capture time period; and generate a test sample electronic signature determined based on the plurality of captured sensor signals combined as a function of time over at least a portion of the sensor signal capture time period, wherein the capture time period is based on the retention time, determined as a function of the plurality of captured sensor signals, of the heaviest analyte in the sample on the GC column; purge the pre-concentrator and GC column with scrubbed air; and identify a pathogen of interest in the test sample based on associating the test sample electronic signature with a predetermined reference sample signature generated as a function of gases and vapors in exhaled breath from a test subject infected with a coronavirus, based on separating a plurality of data point clouds determined as a function of a plurality of pathogen exposure patterns.

The apparatus may further comprise a breathalyzer.

The breathalyzer may be hand-held.

The apparatus may further comprise at least one layer configured to admit ultraviolet (UV) light into at least one chamber of the plurality of chambers.

The apparatus may further comprise a user interface operably coupled with the processor, and the operations performed by the apparatus may further comprise indicate the identified pathogen to a user via the user interface.

The coronavirus may further comprise COVID-19.

At least one of the planar layers may be glass.

In an aspect, an apparatus may comprise: a processor; at least one chamber; a mouthpiece fluidly coupled with at least one chamber; a plurality of sensors operably coupled with the processor, wherein each sensor of the plurality of sensors is disposed in one chamber, and wherein each sensor is distinctly configured to measure a physical quantity of at least one chemical component of a fluid chemical component sample, wherein each sensor has a different response characteristic than each of the other sensors of the plurality of sensors, and wherein each sensor of the plurality of sensors is configured that when the sensor is activated, the sensor communicates the measured physical quantity of the at least one chemical component to the processor as a sensor signal understandable by the processor; at least one valve operably coupled with the processor and configured to be fluidly coupled with at least one chamber; at least one pump operably coupled with the processor and configured to be fluidly coupled with at least one chamber; at least one heater configured to be activated when at least one sensor is active, wherein the at least one heater is configured that when activated the at least one heater heats at least a portion of at least one chamber; and a memory configured to be operably coupled to the processor, wherein the memory comprises encoded processor executable program instructions and data, wherein said instructions and data program configure the processor that when executed by the processor cause the apparatus to perform operations.

The operations performed by the apparatus may further comprise: construct a chromatogram combining retention time separation data and catalytic separation data for a chemical component test sample substantially retained by at least one chamber; generate a test sample electronic signature determined as a function of the combined chromatogram; and identify a pathogen of interest comprising COVID-19 in the test sample based on associating the test sample electronic signature with a predetermined reference sample signature.

At least one chamber may further comprise a Gas Chromatograph (GC) column.

The apparatus may further comprise a GC.

The apparatus may further comprise at least one chamber defined by a structure comprising: at least four planar layers comprising at least one cavity housed but not contained by overlapping apertures through at least two of the planar layers.

Construct the chromatogram combining retention time separation data and catalytic separation data may further comprise operating the at least one valve in combination with activating the at least one pump and activating at least one sensor to separate the test sample while capturing a sensor signal from each sensor of the plurality of sensors.

The different measurement response characteristics of the plurality of sensors may be based on differences in catalytic reactivity between each sensor of the plurality of sensors, and wherein the test sample electronic signature further comprises a plurality of chromatograms having data peaks separated based on different response characteristics of each sensor of the plurality of sensors.

In another aspect, an apparatus may comprise: a processor; at least one chamber; a mouthpiece fluidly coupled with at least one chamber; a plurality of sensors operably coupled with the processor, wherein each sensor of the plurality of sensors is disposed in one chamber, and wherein each sensor is distinctly configured to measure a physical quantity of at least one chemical component of a fluid chemical component sample, wherein each sensor has a different response characteristic than each of the other sensors of the plurality of sensors, wherein the different response characteristics of the plurality of sensors are based on differences in catalytic reactivity between each sensor of the plurality of sensors, and wherein each sensor of the plurality of sensors is configured that when the sensor is activated, the sensor communicates the measured physical quantity of the at least one chemical component to the processor as a sensor signal understandable by the processor; at least one valve operably coupled with the processor and configured to be fluidly coupled with at least one chamber; at least one pump operably coupled with the processor and configured to be fluidly coupled with at least one chamber; at least one heater configured to be activated when at least one sensor is active, wherein the at least one heater is configured that when activated the at least one heater heats at least a portion of at least one chamber; and a memory configured to be operably coupled to the processor, wherein the memory comprises encoded processor executable program instructions and data, wherein said instructions and data program configure the processor that when executed by the processor cause the apparatus to perform operations comprising: construct a chromatogram combining retention time separation data and catalytic separation data for a chemical component test sample substantially retained by at least one chamber, based on operating the at least one valve in combination with activating the at least one pump and activating the at least one heater to separate the test sample received from the mouthpiece while capturing a sensor signal from each sensor of the plurality of sensors; generate a test sample electronic signature determined as a function of the combined chromatogram; and identify a pathogen of interest in the test sample based on associating the test sample electronic signature with a predetermined reference sample signature generated as a function of gases and vapors received from exhaled human breath.

The apparatus may further comprise a pre-concentrator configured to be fluidly coupled with at least one chamber.

The apparatus may further comprise the pre-concentrator fluidly coupled with the mouthpiece.

The pathogen may further comprise bacteria.

The pathogen may further comprise virus.

The virus may further comprise a coronavirus.

The coronavirus may further comprise COVID-19.

In another aspect, an apparatus may comprise: a processor; at least one chamber defined by a structure comprising: at least four planar layers comprising at least one cavity housed but not contained by overlapping apertures through at least two of the planar layers; a mouthpiece fluidly coupled with at least one chamber to receive a test sample of gases and vapors in a test subject's breath exhaled into the mouthpiece; a pre-concentrator configured to be fluidly coupled with at least one chamber; a plurality of sensors operably coupled with the processor, wherein each sensor of the plurality of sensors is disposed in one chamber, and wherein each sensor is distinctly configured to measure a physical quantity of at least one chemical component of a fluid chemical component sample, wherein each sensor has a different response characteristic than each of the other sensors of the plurality of sensors, wherein the different response characteristics of the plurality of sensors are based on differences in catalytic reactivity between each sensor of the plurality of sensors, and wherein each sensor of the plurality of sensors is configured that when the sensor is activated, the sensor communicates the measured physical quantity of the at least one chemical component to the processor as a sensor signal understandable by the processor; at least one valve operably coupled with the processor and configured to be fluidly coupled with at least one chamber; at least one pump operably coupled with the processor and configured to be fluidly coupled with at least one chamber; at least one heater configured to be activated when at least one sensor is active, wherein the at least one heater is configured that when activated the at least one heater heats at least a portion of at least one chamber; and a memory configured to be operably coupled to the processor, wherein the memory comprises encoded processor executable program instructions and data, wherein said instructions and data program configure the processor that when executed by the processor cause the apparatus to perform operations comprising: construct a chromatogram combining retention time separation data and catalytic separation data for a chemical component test sample substantially retained by at least one chamber, based on operating the at least one valve in combination with activating the at least one pump and activating the at least one heater to separate the test sample received from the mouthpiece while capturing a sensor signal from each sensor of the plurality of sensors; generate a test sample electronic signature determined as a function of the combined chromatogram; and identify a pathogen of interest in the test sample based on associating the test sample electronic signature with a predetermined reference sample signature generated as a function of gases and vapors comprising a coronavirus received from exhaled human breath.

The pathogen may further comprise bacteria.

Separate the test sample may further comprise desorb the test sample.

Separate the test sample may further comprise inject the desorbed sample into at least one chamber.

The plurality of sensors may further comprise a thermal conductivity detector (TCD).

The plurality of sensors may further comprise a dual oxide SnO2/CuO sensor.

The plurality of sensors may further comprise a Au/Pd bimetal nanoparticle metal oxide sensor.

The plurality of sensors may further comprise an unmodified SnO2 sensor.

The gases and vapors may further comprise Hydrogen Sulfide.

The gases and vapors may further comprise Carbon Monoxide.

The gases and vapors may further comprise Mercaptans.

The gases and vapors may further comprise Ammonia.

The gases and vapors may further comprise a Volatile Organic Compound (VOC).

The gases and vapors may further comprise a substance generated by a pathogen, wherein the substance generated by the pathogen is not a VOC.

The gases and vapors may further comprise a plurality of VOCs.

In an aspect, a method may comprise: constructing, by a Gas Chromatograph (GC), a chromatogram combining retention time separation data and catalytic separation data for a chemical component test sample; generating a test sample electronic signature determined as a function of the combined chromatogram; and identifying the test sample based on associating the test sample electronic signature with a predetermined reference sample signature.

The chromatogram combining retention time separation data and catalytic separation data may further comprise data captured from a plurality of sensors.

The method may further comprise the plurality of sensors configured that each sensor of the plurality of sensors has a response characteristic difference with respect to each of the other sensors of the plurality of sensors.

The method may further comprise the plurality of sensors configured that each sensor of the plurality of sensors has a response characteristic difference with respect to some but not all of the other sensors of the plurality of sensors.

The method may further comprise the plurality of sensors configured that each sensor of the plurality of sensors has a response characteristic difference with respect to at least one of the other sensors of the plurality of sensors.

The sensor response characteristic may further comprise catalytic reactivity.

The method may further comprise the plurality of sensors configured that each sensor of the plurality of sensors has a catalytic reactivity difference with respect to at least one of the other sensors of the plurality of sensors.

The method may further comprise the plurality of sensors configured that each sensor of the plurality of sensors is designed to have a catalytic reactivity difference with respect to at least one of the other sensors of the plurality of sensors.

The method may further comprise the plurality of sensors is four sensors.

Identify the test sample electronic signature may further comprise identify a pathogen of interest.

The pathogen of interest may further comprise a coronavirus.

The pathogen of interest may further comprise COVID-19.

The method may further comprise the reference sample signature predetermined as a function of a pathogen of interest.

The method may further comprise the reference sample signature predetermined as a function of a coronavirus.

The method may further comprise the reference sample signature predetermined as a function of COVID-19.

The method may further comprise the test sample received from a mouthpiece.

The test sample may further comprise a test subject's exhaled breath.

The method may further comprise the sample test sample captured from a collection device retaining a pathogen.

The collection device may further comprise a covered dish.

The collection device may further comprise a Petri dish.

The method may further comprise decontamination based on purging a portion of the GC with scrubbed air.

The method may further comprise decontamination based on exposing to UV light a portion of the GC configured to admit UV light.

Associating the test sample electronic signature with a predetermined reference sample signature may further comprise separating a plurality of data point clouds determined as a function of a plurality of VOC exposure patterns.

Associating the test sample electronic signature with a predetermined reference sample signature may further comprise pattern recognition.

Associating the test sample electronic signature with a predetermined reference sample signature may further comprise correlation.

Associating the test sample electronic signature with a predetermined reference sample signature may further comprise cross-correlation of the test sample electronic signature with the predetermined reference sample signature.

Associating the test sample electronic signature with a predetermined reference sample signature may further comprise template matching.

Associating the test sample electronic signature with a predetermined reference sample signature may further comprise filtering.

Associating the test sample electronic signature with a predetermined reference sample signature may further comprise frequency domain processing.

Associating the test sample electronic signature with a predetermined reference sample signature may further comprise autocorrelation of the test sample electronic signature.

Associating the test sample electronic signature with a predetermined reference sample signature may further comprise autocorrelation of the predetermined reference sample signature.

Associating the test sample electronic signature with a predetermined reference sample signature may further comprise machine learning.

Associating the test sample electronic signature with a predetermined reference sample signature may further comprise classification.

Associating the test sample electronic signature with a predetermined reference sample signature may further comprise using a decision tree.

Associating the test sample electronic signature with a predetermined reference sample signature may further comprise using a neural network.

A sensor structure is disclosed comprising at least four planar layers subsuming at least one cavity housed but not contained by overlapping apertures through at least two of the planar layers, wherein the at least one cavity comprises a plurality of chambers, and wherein at least one chamber of the plurality of chambers is configured to be in fluid coupling with at least one other chamber. The plurality of chambers may be defined by overlapping apertures through a plurality of the planar layers. The plurality of chambers may include a Gas Chromatograph (GC) column. The planar layers may be flexible flat glass. The planar layers may be 3D printed. The layers may be made with apertures through the layers disposed in a desired pattern to define complex structures by the apertures overlapping between abutting layers when the layers are stacked. The planar layers may be configured to admit ultraviolet light.

In an aspect, an apparatus may comprise: at least four planar layers comprising at least one cavity housed but not contained by overlapping apertures through at least two of the planar layers, wherein the at least one cavity comprises a plurality of chambers, and wherein at least one chamber of the plurality of chambers is configured to be in fluid coupling with at least one other chamber.

The apparatus may further comprise a Gas Chromatograph (GC).

The at least one cavity may further comprise a GC column defined by overlapping apertures through a plurality of the planar layers.

The GC column may further comprise a linear GC column.

The GC column may further comprise a spiral GC column.

The apparatus may further comprise a valve configured to govern the fluid coupling interchangeably between a coupled and an uncoupled state.

The apparatus may further comprise a sensor.

The apparatus may further comprise a heater.

The plurality of chambers may be at least four chambers.

The at least one cavity may further comprise at least one bend.

The at least one bend may be defined by apertures disposed in at least two planar layers.

The at least one cavity may further comprise at least one bend defined by apertures disposed in more than two planar layers.

The planar layers may be flat.

The planar layers may be glass.

The planar layers may be flexible.

The planar layers may be flexible flat glass.

At least four of the planar layers may be flexible flat glass.

At least one planar layer may be 3D printed.

In another aspect, an apparatus may comprise: at least four flexible flat glass layers comprising at least one cavity housed but not contained by overlapping apertures through at least two of the flat glass layers, wherein the at least one cavity comprises at least four chambers, wherein at least one chamber is configured to be in fluid communication with at least one other chamber, and wherein the fluid communication is governed by a valve.

The at least one cavity may further comprise a Gas Chromatograph (GC) column defined by overlapping apertures through a plurality of the flat glass layers.

The at least one cavity may further comprise a Gas Chromatograph (GC) column defined by overlapping apertures through a plurality of the flat glass layers, wherein the GC column further comprises at least one bend defined by apertures disposed in more than two planar layers.

The at least one cavity may further comprise an injector defined by overlapping apertures through a plurality of the flat glass layers.

The at least one cavity may further comprise a pre-concentrator tube defined by overlapping apertures through a plurality of the flat glass layers.

The apparatus may further comprise a pump.

The apparatus may further comprise at least one 3D printed sensor disposed on at least one of the layers.

The apparatus may further comprise at least one 3D printed sensor that was deposited by 3D printing on at least one of the layers.

The apparatus may further comprise a mouthpiece.

In another aspect, an apparatus may comprise: at least four planar layers comprising at least one cavity housed but not contained by overlapping apertures through at least two of the planar layers, wherein the at least one cavity comprises a plurality of chambers, and wherein at least one of the planar layers is configured to admit ultraviolet (UV) light into at least one chamber of the plurality of chambers.

The at least one cavity may further comprise a Gas Chromatograph (GC) column defined by overlapping apertures through a plurality of the planar layers.

The apparatus may further comprise a scrubber configured to be in fluid communication with the GC column.

The at least one cavity may further comprise a pre-concentrator defined by overlapping apertures through a plurality of the planar layers, and wherein the apparatus may further comprise a mouthpiece configured to be in fluid communication with the pre-concentrator.

The planar layers may be flexible flat glass.

The apparatus may further comprise at least one 3D printed structure disposed on at least one of the at least four planar layers.

At least two of the planar layers may be stacked.

At least two of the planar layers may be fused.

The at least one cavity may further comprise at least one bend.

The at least one cavity may further comprise at least one bend defined by apertures disposed in more than two planar layers.

In an aspect, a flat glass-sensor structure apparatus may comprise at least four flexible flat glass layers comprising at least one cavity housed but not contained by overlapping openings through at least two of the flat glass layers.

The flat glass-sensor structure may further comprise a sensor configured to be operably coupled with the at least one cavity.

The flat glass-sensor structure may further comprise a sensor within the at least one cavity.

The flat glass-sensor structure may further comprise a membrane with at least one sensory sub-area and a plurality of flat glass connectors.

The flat glass-sensor structure may further comprise each flat glass connector of the plurality of flat glass connectors in contact with the at least one sensory sub-area.

The flat glass-sensor structure may further comprise a resistive heating element.

The resistive heating element may be on top of one of the flat glass layers.

The resistive heating element may be in plane with one of the flat glass layers.

At least two of the at least four flexible flat glass layers may be stacked.

At least two of the at least four flexible flat glass layers may be fused.

In another aspect, a flat glass-sensor structure may comprise: at least four flexible flat glass layers comprising at least one cavity housed but not contained by overlapping openings through at least two of the flat glass layers; and a sensor operably coupled with the at least one cavity.

The sensor may be within the at least one cavity.

The sensor may further comprise a membrane.

The membrane may further comprise at least one sensory sub-area and a plurality of flat glass connectors.

Each flat glass connector of the plurality of flat glass connectors may be in contact with the at least one sensory sub-area.

The openings through at least two flat glass layers may be different sizes.

The openings through at least two flat glass layers may be different patterns.

The at least one cavity may be contained by the at least four flexible flat glass layers.

The flat glass-sensor structure may further comprise a fluid port operably coupling the at least one cavity with the environment.

The flat glass-sensor structure may further comprise an electrical port configured to operably couple the sensor with a device external to the flat glass-sensor structure.

In another aspect, a flat glass-sensor structure may comprise: at least four flexible flat glass layers comprising at least one cavity housed but not contained by overlapping openings through at least two of the flat glass layers; at least one sensor operably coupled with the at least one cavity, said at least one sensor comprising: a membrane with at least one sensory sub-area and a plurality of flat glass connectors, wherein each flat glass connector of the plurality of flat glass connectors is in contact with the at least one sensory sub-area; and a resistive heating element that is on top of or in plane with one of the flat glass layers.

The at least one sensor may be within the at least one cavity.

The flat glass-sensor structure may further comprise at least one alignment hole through at least one of the at least two flat glass layers having overlapping openings.

The flat glass-sensor structure may further comprise at least one alignment post configured in at least one of the at least two flat glass layers having overlapping openings.

The flat glass-sensor structure may further comprise at least one alignment hole in mechanical union with at least one alignment post.

The flat glass-sensor structure may further comprise at least one alignment hole disposed in each layer of a plurality of layers, wherein the at least one alignment hole disposed in one layer of the plurality of layers is in mechanical union with at least one alignment post configured in another layer of the plurality of layers.

The flat glass-sensor structure may further comprise at least one alignment hole disposed in at least one of the at least two flat glass layers having overlapping openings, and at least one alignment post in mechanical union with the at least one alignment hole, wherein the at least one alignment post is configured in a layer distinct from the layer having the at least one alignment hole.

The flat glass-sensor structure may further comprise a pattern cut in at least two stacked layers.

The flat glass-sensor structure may further comprise a different pattern cut in each layer of the at least two stacked layers.

The at least one cavity may further comprise a continuous channel defined by a distinct pattern cut in each layer of the at least two stacked layers.

The present disclosure teaches a chemical analyzer. The chemical analyzer may comprise a GC. The chemical analyzer may be portable. The chemical analyzer may be a portable lab. The chemical analyzer may be hand-held. The hand-held chemical analyzer may be a breathalyzer. The chemical analyzer may be configured to analyze a sample emitted by a pathogen within a collection device. The chemical analyzer may be configured to analyze a sample collected from a test subject's exhaled breath. The chemical analyzer may identify a pathogen based on determining a test sample electronic chemical signature and associating the test sample electronic chemical signature with a predetermined reference sample electronic chemical signature. The chemical analyzer may determine the test sample electronic chemical signature based on fusing or combining retention time separation on the GC column with catalytic separation determined as a function of measurement data captured during time separation. The measurement data captured during time separation may be captured from multiple sensors having catalytic reactivity differences among the multiple sensors. The catalytic reactivity differences among the multiple diverse sensors results in sensor response characteristic differences among the sensors, permitting multiple chromatogram peaks to be more effectively separated, resulting in more selective chemical signature identification. The multiple sensors may be configured in a quasi-orthogonal array. The multiple sensors may be more than one sensor. The multiple sensors may be four sensors. The multiple sensors may be more than four sensors. The chemical analyzer may determine a diagnosis for a patient based on the reference sample associated with the test sample. Associating a reference sample with the test sample may comprise pattern recognition, classification, or correlation. The chemical analyzer may be configured to use scrubbed ambient air as carrier gas. The chemical analyzer may be configured to purge analyzer components using scrubbed ambient air. Some chemical analyzer components may be constructed with punctuated layered glass technology. Some chemical analyzer components may be constructed with 3D printing technology. The chemical analyzer components may be configured to admit UV light to enhance decontamination.

Various implementations may achieve one or more technical effect. For example, some implementations may improve a user's ease of access to disease diagnosis. This facilitation may be a result of increasing the availability of effective disease diagnostic devices, to reduce the user's effort scheduling a lab test and traveling to a lab to be tested. Various designs may reduce the cost to test for pathogen infection. Such reduced pathogen infection testing cost may be a result of a testing device designed to provide faster testing cycle times. For example, some multi-sensor pathogen identification device designs may be configured to purge analyzer components with scrubbed ambient air, permitting faster cleaning, and increasing the number of tests that can be administered in a time period. Some implementations may improve disinfection effectiveness. This facilitation may be a result of a testing device designed to admit UV light through layered glass to chemical analyzer components, to disinfect the components more thoroughly between tests that may contaminate the device with an infectious pathogen.

Some designs may improve testing device portability. Such improved testing device portability may be a result of a testing device designed to use scrubbed ambient air carrier gas, eliminating the need for a bulky and expensive carrier gas tank to be located with or transported with the testing device. Some test devices may improve pathogen identification accuracy. This facilitation may be a result of improved separation of data peaks from multiple combined chromatograms, based on combining retention time separation on the GC column with catalytic separation achieved with sensor catalytic reactivity diversity. For example, combining retention time separation on the GC column with catalytic separation determined as a function of measurement data captured from multiple sensors having catalytic reactivity differences among the multiple sensors may permit more selective chemical signature identification.

The details of various aspects are set forth in the accompanying drawings and the description below. Other features and advantages will be apparent from the description and drawings, and from the claims.

BRIEF DESCRIPTION OF THE DRAWINGS

FIGS. 20A-F show various views of an exemplary micro GC in an illustrative hand-held configuration.

Like reference symbols in the various drawings indicate like elements.

DETAILED DESCRIPTION

To aid understanding, this document is organized as follows. First, detecting and identifying a pathogen of interest based on an electronic chemical signature determined as a function of sensor measurement response characteristic differences resulting from catalytic reactivity diversity among a plurality of sensors is briefly introduced with reference to FIG. 1. Second, with reference to FIGS. 2-12, the discussion turns to exemplary implementations that illustrate 3-D printing glass/metal and punctuated layered glass technology. Specifically, various 3-D printed glass/metal and punctuated layered glass technology sensor structure examples are disclosed. Finally, with reference to FIGS. 13-37, exemplary MGC component and configuration designs and pathogen detection and identification results are presented with exemplary MGC processing techniques, to explain improvements in pathogen detection and identification technology.

It is to be understood that the specific devices and processes illustrated in the attached drawings and described in the following specification are exemplary embodiments of the inventive concepts defined in the appended claims. Hence, specific dimensions and other physical characteristics relating to the embodiments disclosed herein are not to be considered as limiting, unless the claims expressly state otherwise.

Comprehensive analysis of complex gas mixtures can be accomplished through implementation of analytical gas chromatography. A gas chromatographic column separates complex sample mixtures into individual components. As a result, the individual components of the mixture are delivered to the detector separated in time. Retention times on the GC column are indicative of the component identity. Analytical gas chromatograph can be combined with a pre-concentrator to deliver higher concentrations of components to the detector than are in the original sample.

Gas delivery and separation system for analytical gas chromatographs can be 3-D printed from metal or glass. Contrary to traditional manufacturing processes such as drilling, milling, sawing, molding, and joining, 3D printing offers freedom of design, complex geometry with high precision, elimination of tooling, rapid prototyping, and cost-effective customization. A 3D-printed glass or metal column can be developed towards micro-GC applications. The 3-D printed portion of the device includes the chromatography column, the injector module, and a pre-concentrator.

Figure 1:
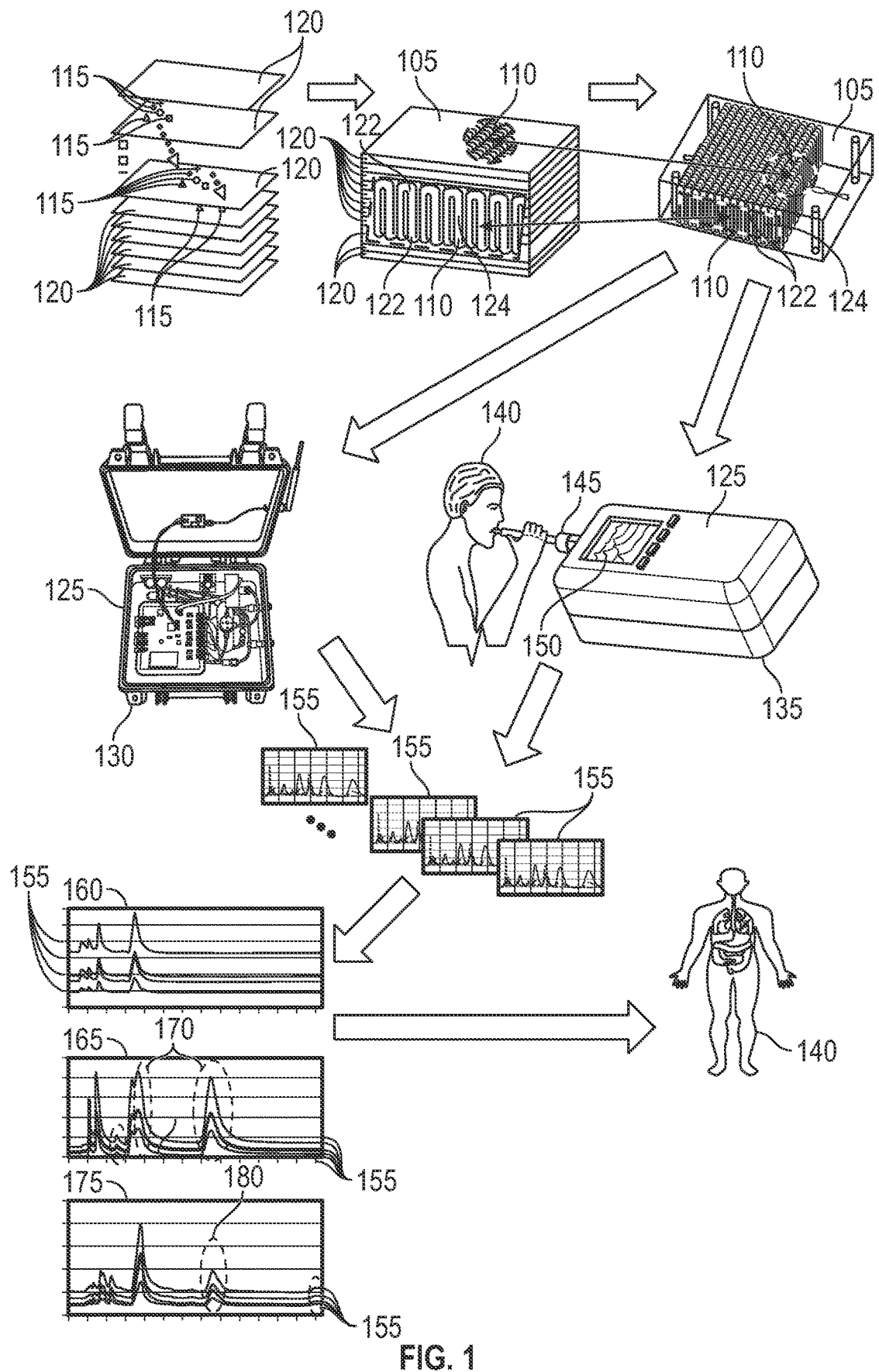
FIG. 1 shows an illustrative example using an exemplary Multisensory Gas Chromatography (MGC) device to detect and identify a pathogen of interest.

FIG. 1 shows an illustrative example using an exemplary Multisensory Gas Chromatography (MGC) device to detect and identify a pathogen of interest. In FIG. 1, the structure 105 includes the internal device 110 defined by the apertures 115 overlapping between abutting planar layers 120 when the planar layers 120 are stacked. In the depicted example, the internal device 110 is a linear GC column, also depicted at least by FIG. 2. In the illustrated example, the apertures 115 include holes of various shapes and sizes through planar layers 120. The depicted apertures 115 are disposed in various patterns in the planar layers 120. In the depicted example, the patterns the apertures 115 are disposed in are designed to define the linear GC column within the structure 105, based on the apertures 115 overlapping between abutting planar layers 120 when the planar layers 120 are stacked. The exemplary linear GC column may be considered a channel within the structure 105. In FIG. 1, the exemplary linear GC column includes channel bend 122 structural features defining curved or bent edges in the exemplary channel 124. Each exemplary channel 124 bend 122 may result from apertures 115 located in the planar layers 120 so the apertures 115 overlap to form the curved or bent edges as abutting layers are stacked. Multiple channel 124 bend 122 features having distinct radii may be formed based on adjusting the number of planar layers 120, adjusting the planar layer 120 thickness, and the locations, sizes, and shapes of apertures 115 in each planar layer 120, such that the apertures 115 located in the planar layers 120 would overlap to form a curved or bent edge defined by the aperture 115 interior edges, as abutting planar layers 120 are stacked. In an illustrative example, a sensor structure having an exemplary channel 124 defined by apertures 115 located in the planar layers 120 so the apertures 115 would overlap to form a curved or bent edge as abutting planar layers 120 are stacked may result in improved flow in the channel 124. Various implementations of the internal structure 110 may include a spiral GC column, depicted at least by FIG. 3. The patterns the apertures 115 are disposed in on the planar layers 120 may be designed to define any device 110 within the structure 105, based on the apertures 115 overlapping between abutting planar layers 120 when the planar layers 120 are stacked. The planar layers 120 may be flat. The planar layers 120 may be glass. The planar layers 120 may be flexible. The planar layers 120 may be flat glass. The planar layers 120 may be flexible flat glass. The planar layers 120 may be 3D printed. In the depicted example, portions of the linear GC column structure illustrated as within the structure 105 are visible in cutaway views delineated by dashed lines on the top of and one side of the structure 105. The structure 105 may include a cavity defined by the apertures 115 overlapping between abutting planar layers 120. The cavity may include one or more chamber defined by the apertures 115 overlapping between abutting planar layers 120. The cavity may include one or more channel defined by the apertures 115 overlapping between abutting planar layers 120. The structure 105 may be operably coupled with one or more sensor 125 configured with the GC column in the portable GC lab 130. The structure 105 may be operably coupled with one or more sensor 125 configured with the GC column in the handheld GC 135. In the illustrated example, the portable GC lab 130 may receive a test sample of a fluid chemical component sample emitted by a pathogen into a collection device fluidly coupled with the portable GC lab 130. In the depicted example, the handheld GC 135 may receive a test sample of a fluid chemical component sample emitted in the exhaled breath of the test subject 140 into the mouthpiece 145. In the illustrated example, the portable GC lab 130 is configured to detect and identify a pathogen of interest in the test sample collected from a pathogen. In the illustrated example, the handheld GC 135 is configured to detect and identify a pathogen of interest in the test sample received in the test subject 140 exhaled breath. In the depicted example, the portable GC lab 130 is configured with digital interfaces adapted to communicate test results and to receive control directives and configuration data. In the illustrated example, the handheld GC 135 includes the user interface 150 configured to communicate with an operator. In the depicted example, the portable GC lab 130 and the handheld GC 135 are each configured with four sensors 125, wherein each sensor 125 is distinctly configured to measure a physical quantity of a chemical component of the fluid chemical component test sample, during chemical component separation from the sample on the GC column. The sensors 125 are configured to communicate as a sensor signal the measured chemical component physical quantity to a processor configured in the portable GC lab 130 or the handheld GC 135. In the depicted example, each sensor 125 has a different sensor measurement response characteristic than each of the other sensors 125 of a sensor 125 array configured in each of the portable GC lab 130 and the handheld GC 135. The sensor 125 array may include any number of sensors 125. In the depicted example, each of the portable GC lab 130 or the handheld GC 135 are configured with a sensor array including four sensors 125. In the depicted example, the processor creates a distinct individual chromatogram 155 for each of the signals received by the processor from the more than one sensor 125. In the illustrated example, the processor constructs a combined chromatogram from the multiple individual chromatograms 155 generated by the processor from the sensor 125 signals. In the depicted example, the processor generates a test sample electronic signature determined as a function of the combined chromatogram. In the illustrated example, the combined chromatogram 160 includes the multiple individual chromatograms 155. In the depicted example, the processor constructed the combined chromatogram 160 based on sensor 125 measurement of clean air as a baseline. In the illustrated example, the combined chromatogram 165 was constructed by the processor based on sensor 125 measurement of emissions from a pathogen of interest in a test sample collected by an exemplary portable GC lab 130. In the illustrated example, the portable GC lab 130 processor identifies the pathogen of interest based on associating the test sample electronic signature with a predetermined reference sample signature. The predetermined reference sample signature may be a signature of a known pathogen. In the depicted example, the circled peaks 170 belong to the signature of the pathogen identified by the portable GC lab 130. In the illustrated example, the combined chromatogram 175 was constructed by the processor based on sensor 125 measurement of a pathogen of interest in a test sample received by an exemplary handheld GC 135. In the illustrated example, the handheld GC 135 processor identifies the pathogen of interest based on associating the test sample electronic signature with a predetermined reference sample signature. The predetermined reference sample signature may be a signature of a known pathogen. In the depicted example, the circled peaks 180 belong to the signature of the pathogen identified by the handheld GC 135. The known pathogen reference signature may be, for example, a coronavirus, such as COVID-19. In the depicted example, the disclosed MGC provides a test result for the test subject 140, based on the signature of the pathogen identified by the MGC processor. The disclosed MGC devices improve pathogen identification accuracy and reduce the cost to test for a pathogen's presence. This facilitation may be a result of improved separation of data peaks from multiple combined chromatograms, based on combining retention time separation on the GC column with catalytic separation achieved with sensor catalytic reactivity diversity. For example, combining retention time separation on the GC column with catalytic separation determined as a function of measurement data captured from multiple sensors having catalytic reactivity differences among the multiple sensors may permit more selective chemical signature identification.

Figure 2:
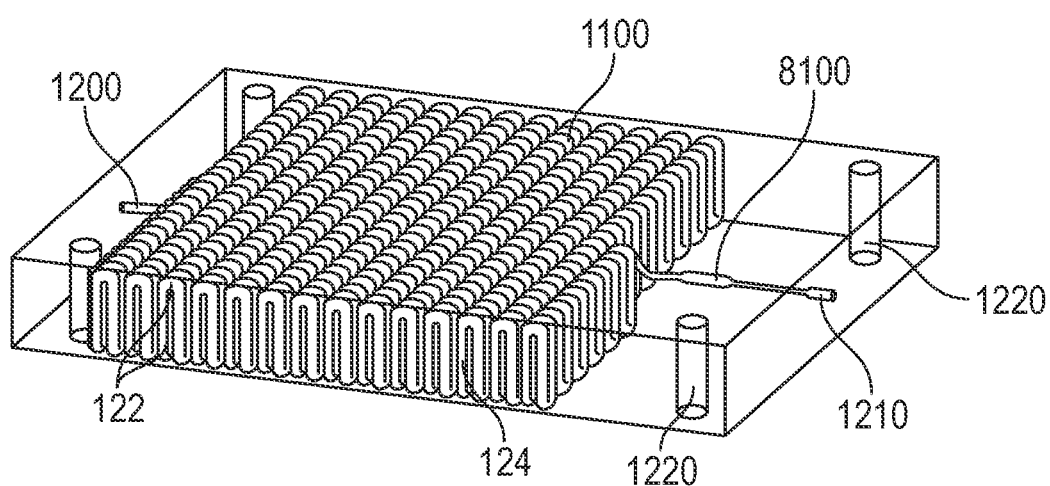
FIG. 2 shows a perspective view of a multi-layer, flat glass structure wherein a linear gas chromatography (GC) column is formed from the glass.

FIG. 2 shows a perspective view of a multi-layer, flat glass structure wherein a linear gas chromatography (GC) column is formed from the glass. In one embodiment, the entire structure shown can be 3-D printed from metal or glass, using flexible flat glass that can be quickly laser cut, stacked, and formed into unitary multi-layer, flat glass structures. These unitary structures can be functional (e.g., designed for fluids to flow through them), and/or can house entire instruments or components thereof (e.g., mobiles phones, sensors, batteries, circuit boards, etc.). Because the structures can be transparent or translucent one can take advantage of the ability to direct light (e.g., UV light) into and/or through them.

Glass: Glass refers to a substance typically formed by melting sand, sodium carbonate (soda), and calcium oxide (lime)(silicate glass). The glass can also be formed with $B_2O_3$ and/or $Al_2O_3$ to form borosilicate, aluminosilicate, or alumino-borosilicate glass. Additional additives can also be included during the formation of the glass or afterwards (e.g., polymer or metal oxide coatings). The glass can be transparent, translucent, or opaque. For translucent or opaque, the glass can be formed with this property. Alternatively, the glass can be modified to be translucent or opaque. Examples of modification include the addition of a translucent or opaque layer (e.g., a coating on one or both sides of one or more glass layers). The glass can be made or modified such that it reflects (in or out) and/or filters (in or out) certain wavelengths of light. In another aspect, a modified glass layer can further comprise another glass layer (e.g., to sandwich a coating to protect and/or enhance the modification).

Flat: Flat refers to both the geometry and the roughness of the glass. The flat glass used in the present invention is both planar (geometry) and smooth (roughness). Planar means that the top and bottom of each layer is in the same geometric plane. The flat glass has length, width, and thickness (height), with the thickness being very small (see examples of thickness below). Roughness is defined via a roughness average (Ra) and peak-to-valley roughness (Rpv). Examples of the roughness average (Ra) of the flat glass include less than 5, 4, 3, 2, 1, 0.9, 0.8, 0.7, 0.6, 0.5, 0.4, 0.3, 0.2, and 0.1 nm. Examples of peak-to-valley roughness (Rpv) include less than 50, 45, 40, 35, 30, 25, 20, 15, 10, and 5 nm.

Fluid: Throughout this disclosure, the term "fluid" is used interchangeably with the term "gas." For example, an element that is "fluidly coupled" or "fluidly connected" or in "fluid communication" is capable to or would be capable to be in a coupled, connected, or communication mode with respect to gas, fluid, gas and fluid, gas or fluid, or any combination or mixture of gas or fluid.

When the structure is cylindrical, the flat glass is a plane curve (e.g., the flexible glass has wound around a spool).

Examples of the thickness of the flat glass include 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, to 225 pm, or greater.

As an example, the presently claimed invention uses glass that is stable to at least 600° C. Other examples of the temperature at which the glass remains stable includes 625, 650, 675, 700, 725, 750, 775, and 800° C.

Typically, the glass used in the present invention is flexible. For example, the glass is bendable or capable of forming a curved structure without shattering (e.g., a non-brittle substance). This allows for the glass to be formed into rolls, which can be unwound and cut during the present manufacturing process.

Examples of commercially available flat glass useful in the present invention include ultra-thin glass from Schott (e.g., AF 32® eco and AF 32® eco) as well as Corning® Willow® glass.

An advantage of the present unitary structures is that they form what is essentially a solid block (or cylinder) of hermetically sealed glass. The solid block (or cylinder) is sturdy and is resistant to numerous environmental challenges (freezing temperatures, high temperatures, precipitation, submersion in water, etc.).

In an aspect, the present invention provides a novel multi-layer, flat glass structure comprises a. a top flat glass layer; b. a bottom flat glass layer; and, c. at least four (4) internal flat glass layers, wherein the internal flat glass layers are each, individually, in contact with two other flat glass layers and the top and bottom flat glass layers are each, independently, in contact with one internal flat glass layer; the structure has a top, bottom, and four sides; and, at least one portion of glass (cut-out) is missing from a plurality of the layers.

In another aspect, a plurality of portions of glass (cut-outs) are missing from a plurality of the layers. In another aspect, a plurality of the missing glass portions in the plurality of layers are aligned to form a channel(s) (e.g., via) and/or a chamber(s). In another aspect, the structure, comprises at least 10 layers. In another aspect, the structure, comprises at least 50 layers. In another aspect, the structure, comprises at least 100 layers.

The number of flat glass layers (the total of top, bottom, and internal) is only limited by the design of the structures, specifically their thickness (height). Examples include 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, and 2000. Examples also include: (a) 10-2000, (b) 10-1000, (c) 100-2000, (d) 100-1000, and (e) 100-500.

The geometry of the structures can vary depending on the function of the structure and/or the function of the components housed by the structure. In another aspect, the structure is a quadrilateral. Examples of quadrilaterals include square, rectangular, rhombus, parallelogram, trapezoid, and kite (adjacent pairs of equal length sides). In another aspect, the structure is round. Examples of round structures include circular, oblong, and egg-shaped. In another aspect, the unitary structure is a combination of part quadrilateral and par round. An example of the combination geometry is a structure that is round on one end and square or rectangular on the other.

In another aspect, the structure, further comprises: a plurality of fluid ports. The ports allow for gases and/or liquids to be introduced into and flow through the structure. Examples of the number of ports include 2, 3, 4, 5, 6, 7, 8, 9, and 10. The ports are connected to an internal structure (e.g., glass channel) for the gas or liquid to flow into and through. This is useful when the structure houses a sensor (e.g., a gas sensor or plurality of gas sensors) or functions as a gas chromatograph (GC) column. In another aspect, the ports allow for external tubing or connectors to be inserted into and/or connected with the structure. For internal connection, external tubing is plugged into the completed structure. The ports can be the glass of the structure itself or can be a non-flat glass connecter that is affixed to the inside of the completed structure. For glass ports, they can be formed in the structure during manufacture. Alternatively, ports can be formed (e.g., drilled) after the unitary structure has been made. For external connection, a connector can affix (e.g., glued, fused, or mechanically attached) to the structure thereby allowing a connection that is external to the structure. Attachment of the external connector can occur during the stacking of the layers or after the structure has been made.

In another aspect, the structure, further comprises electrical connectors. Examples of the number of electrical connectors include 2, 3, 4, 5, 6, 7, 8, 9, and 10-100. As an example, the connectors are electrical ports than can allow an electrical device (e.g., cable or wire) to be plugged into the structure. Another example of electrical connectors is external conducting pins (e.g., gold- or gold-plated pins) that extend from the inside of the structure to the outside of the structure, thereby allowing for clipping, crimping, plugging, or other ways of electrical connection.

Electrical connectors as well as electrical components housed (partially or fully) in the completed structure are typically electronically connected to one another via internal electronic connections. Examples of these connections include wires, traces, solder, and combinations thereof. Internal electronic connections are cut during the manufacturing process. The internal (and external, if present) electrical connections are inserted/laid/deposited during the manufacturing process or after the structure has been made. As an example, an electrical port can also be a glass inlet housing an electrical connector a wire, trace, or solder located inside or close enough to electronically communicate with a plug inserted therein.

In another aspect, the structure, further comprises: a plurality of mechanical pins 1220. In one embodiment these mechanical pins pass through the top and bottom of a single layer flat glass structure. In another embodiment, they also pass through the internal layers of the glass-sensor and at least into the top and bottom layers of a multi-layer structure. In one embodiment, one or more of the mechanical pins 1220 pass through at least one of the top or bottom of a single flat glass layer structure. In one embodiment, the mechanical pins pass through at least one of the top or bottom layers and extend beyond the structure of a multi-layer flat glass structure. The mechanical pins can be used to mount the structure (e.g., attach the structure to a vehicle or a computer case). The mechanical pins 1220 can also be screws or bolts or other types of fasteners. The mechanical pins 1220 can also be electrically conductive.

Figure 3:
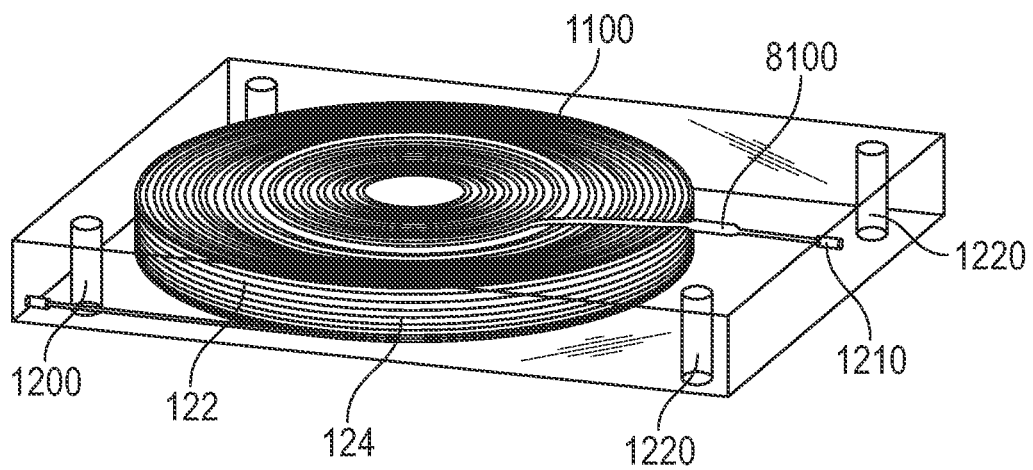
FIG. 3 shows a perspective view of a multi-layer, flat glass structure wherein a spiral GC column is formed from the glass.

In another aspect, the mechanical pins 1220 are electrically conductive and are in electrical connection with at least one component housed in the structure. In another aspect, the plurality of mechanical pins extends beyond the bottom and/or top of the structure, are electrically conductive, and are in electrical connection with at least one of component housed in the structure. A glass structure that is a GC column is illustrated in FIG. 2 and FIG. 3 comprising an inlet port 1200, an outlet port 1210 and a glass column 1100.

In FIG. 2, the column is formed via a pathway in the internal layers. More specifically, the column runs up and down the height of the glass structure. At least the top and bottom layers house but do not contain the column. Additional internal layers adjacent to the top and/or bottom layers can also house, but not contain the column. The remaining inner layers have been cut (comprise missing portions or cut outs) so that when stacked a continuous glass channel (column) is formed. A linear column is shown in FIG. 2 while FIG. 3 shows a spiral column.

Typical column lengths for GC columns are 30 m and 60 m. Due to the ease of manufacturing the present GC columns, the column length is easily adjusted. Examples include 10, 15, 20, 25, 30, 35, 40, 45, 50, 55, 60, 65, 70, 75, 80, 85, 90, 95 and 100 m.

The internal diameter (I.D.) of the column is also variable as it is set by the laser cut. Examples of the column I.D. include 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, and 0.80 mm.

One of the advantages of the present invention is the ability to rapidly and precisely manufacture small, unitary, functional, single and multi-layer, flat glass structures. These structures avoid the need for tubing, connectors, and other parts that the glass can function as or for which the need is removed. For example, the GC structure in FIG. 2 can be 63.5 mm wide, 80 mm long, and 10 mm high. Other dimensions are possible. The length of the structure in FIG. 2 is determined by how much glass is cut off from the starting roll. The height is determined by the number of flat glass layers that are stacked and fused together. The width is usually set by the width of the roll. However, the width could be narrower than the roll if desired (e.g., one or both edges could be removed during manufacture). Alternatively, the width is determined by how much glass is cut off from the roll and the length corresponds to the width of the roll.

In another aspect, the GC column structure, further comprises: a detector. The structure can comprise a detector that is or contains a sensor 8100 or can be connected to a detector that is or contains a sensor 8100 via the outlet port 1210.

The GC detector can be a sensor such as those described in WO 2017/165567, WO 2018/160650, U.S. Pat. No. 10,132,769, US Patent Publication No. 2018/0086664, and US Patent Publication No. 2018/0215611, the contents of which are incorporated by reference, in their entirety. Alternatively, the GC detector can be selected from: (a) flame ionization detector (FID), thermal conductive detector (TCD), akali flame detector (AFD), alkali flame ionization detector (AFID), catalytic combustion detector (CCD), flame photometric detector (FPD), electron capture detector (ECD), and combinations thereof (e.g., TCD in sequence with an FID). The detector can also be a spectrometer such as a mass spectrometer (MS) or NMR (nuclear magnetic resonance spectrometer), or a combination (e.g. GC-MS, GC-NMR or GC-MS-NMR).

In another aspect, the present invention provides a novel method of manufacturing a multi-layer, flat glass structure, the method, comprising: a. unrolling a spool of flat glass to provide a first length of flat glass; b. cutting the first length of glass away from the spool to form a bottom layer of flat glass, wherein the cutting optionally includes cutting a desired pattern into the first length of glass; c. placing the bottom layer of flat glass into an alignment frame; d. unrolling the spool to provide a second length of flat glass; e. cutting the second length of glass away from the spool to form an internal layer of flat glass, wherein the cutting optionally includes cutting a desired pattern into the second length of glass; f placing the internal layer of flat glass into the alignment frame and in contact with the bottom layer; g. repeating steps (d)-(f) for each internal layer of flat glass, wherein each additional internal layer is placed in contact with another internal layer; h. unrolling the spool to provide a last length of flat glass; i. cutting the last length of glass away from the spool to form a top layer of flat glass, wherein the cutting optionally includes cutting a desired pattern into the last length of glass; j. placing the top layer of flat glass into the alignment frame and in contact with an internal layer; and k. fusing the stacked glass layers to form a multi-layer, flat glass structure.

Cutting of the flat glass layers is typically done via laser. Using a laser allows for precision, accuracy, and speed. The pieces cut out drop away as the glass layer is moved. Optionally, mechanical force (e.g., agitation, twisting, or forced air) is applied to the cut layer to ensure all unwanted glass pieces drop away.

In another aspect, at least one alignment hole is cut into each layer. Examples of the number of alignment holes include 1, 2, 3, and 4. The alignment hole(s) allows for a light to shine through each layer to ensure precise alignment. Alternatively, an alignment post (or posts) can be used and each layer can be stacked onto the alignment post (or posts) via the alignment hole(s). In this aspect, the alignment frame, comprises at least one alignment post.

Figure 4:
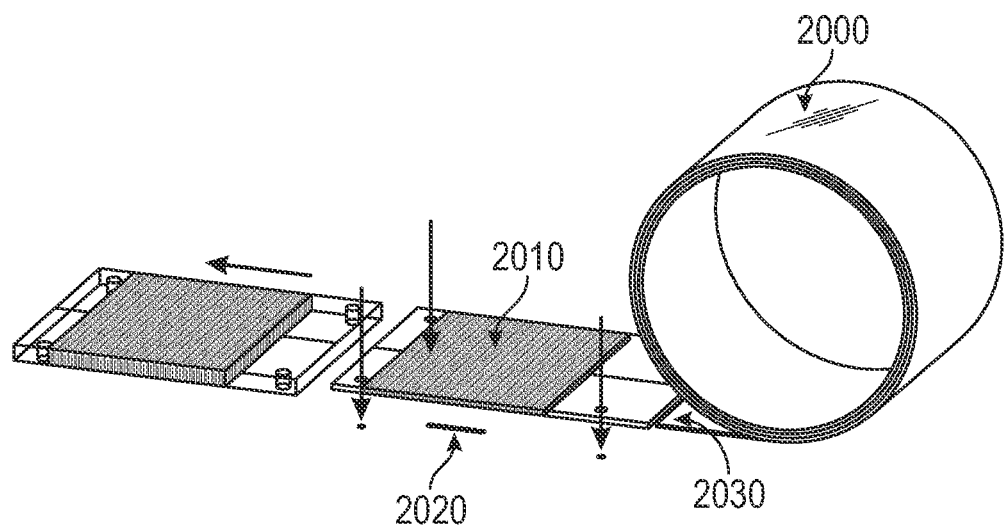
FIG. 4 shows a perspective view of a full and partially formed multi-layer, flat glass structure wherein a linear GC column is formed from the flat glass.
Figure 5:
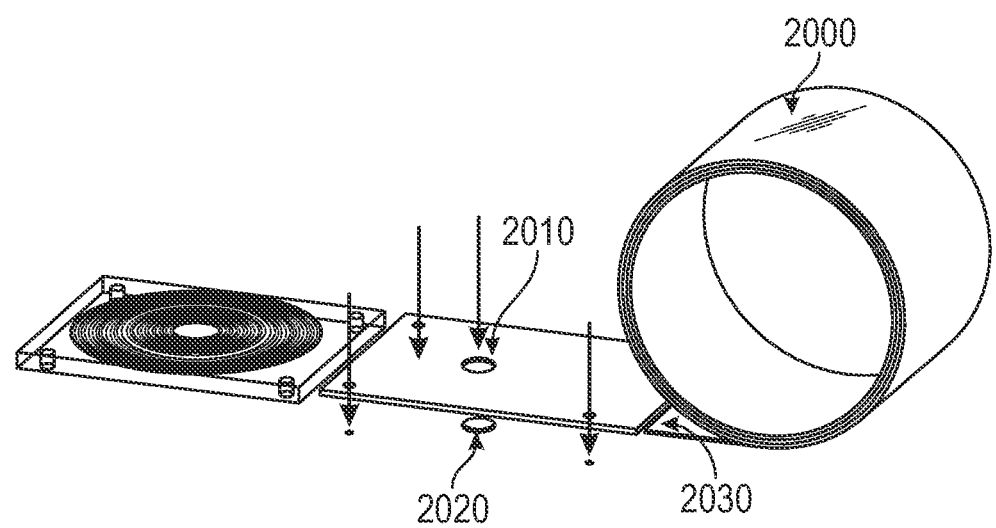
FIG. 5 shows a partially formed multi-layer, flat glass structure wherein a spiral GC column is formed from the glass.

FIG. 4 shows a partially formed flat glass structure that is forming a linear GC column. As can be seen in this figure, flat glass has been unwound from a spool of glass 2000, a laser pattern 2010 has been formed, the cut-outs 2020 have dropped away, a cut line 2030 has been made (see the line near the glass spool), and layers have been stacked. The process shown in FIG. 4 is repeated until the desired number of layers have been cut and stacked. FIG. 5 shows how a spiral column is formed.

One of the advantages of the present manufacturing process is that each layer can be patterned the same or differently from other layers. The process can be automated by pre-programming the pattern into a computer-controlled laser. The unrolling, cutting, stacking, etc. can all be automated, thereby allowing for high-speed, precision manufacturing of the present flat-glass structures.

In another aspect, fusing is performed using ultrasound and/or applying pressure. In another aspect, the fusing step is performed by pressing the layers of the structure together with enough pressure that the layers fuse (adhere) to one another. In another aspect, the integrity of the stack is maintained by the alignment frame while pressure is applied. This is to ensure that the layers remain aligned, which can be important if channels or other structures are formed by the stacking.

In another aspect, pressure is applied to the partially completed structure to limit the amount of pressure required to fuse the entire structure. For example, pressure can be applied after every 5, 10, 15, 20, 25, 30, 35, 40, 45, 50, or 100 layers have been stacked.

In another aspect, the top layer is cut and stacked first and the bottom layer is cut and stacked last. This would be building the structure from the top up as opposed to the bottom-up process described above. In another aspect, the optional pattern cutting and cutting a length of flat glass away from the spool can be done simultaneously, sequentially (e.g., from one side to another), or in parts or segments.

As described above, the present multi-layer glass structures can comprise various components (e.g., sensors, batteries, and wiring). One way to include components in the structure is to add them as the layers of glass are stacked. The patterns created in the glass layers can result in cavities/openings as layers are stacked. The cavities/openings allow for components to be installed during stacking.

In another aspect, the method, further comprises 1. installing one or more components into a cavity formed by at one or more internal layers. This installing step can occur at any time during the stacking of internal layers (or before or after if the top and/or bottom layer has a cut-out in it). It can also occur multiple times in order to assemble a multi-component system. Cavity includes individual or multiple small holes (e.g., channel(s) and via(s)) and individual or multiple larger cut-outs (e.g., circular, square, and rectangular openings), which can form a chamber(s). For example, the battery of a cellular phone could be located near the bottom of the structure and an LED screen could be located at the top of the structure. The battery would be installed before the LED in a bottom up build (and vice versa). Electrical contacts, wiring, etc. could be installed throughout the stacking process (multiple installing steps). Fusing of the glass structure could occur before each component is installed (multiple fusing steps), after each component is installed (multiple fusing steps), or after the stacking is complete (one fusing step).

In another aspect, the method, further comprises m. placing a first modified layer onto the stack. In this aspect, a flat glass layer is modified before or during the manufacturing process and placed onto the stack as the structure is made. This allows one to maintain a high-speed process without stopping to modify a layer (e.g., deposit metal traces). The layer to be modified can come from the same flat glass roll being used to form the structure, from a different roll, or a different source (e.g., a large sheet onto which a plurality of modifications is made). Examples of the modifications include building an integrated circuit or sensor on a glass layer and forming metal traces onto the layer (e.g., metal deposition or via an etching method). By having a supply of modified layers on hand, structures can be rapidly made with the modified layer (or layers) being placed on the stack at the appropriate time (first (top/bottom), last (top/bottom), or somewhere in the middle). In another aspect, the method, further comprises n. placing a plurality of modified layers onto the stack. Examples of the number of modified layers in this aspect include 2, 3, 4, 5, 6, 7, 8, 9, 10, 11, 12, 13, 14, 15, 16, 17, 18, 19, and 20.

By forming the glass structure as two or more modified layers, at least one component can be encased in the structure by placing the component(s) into (onto) one layer and then bringing the other layer into contact and fusing them together. As an example, a radiation sensitive beacon (e.g., sensor, battery, and transmitter) could be enclosed in a multi-layer glass structure by first forming a top half and bottom half, placing the beacon between the halves, and then fusing the halves together. As noted above, if it is necessary to be able to open the structure to repair or replace components (e.g., faulty battery), the plurality of structures can be mechanically connected (e.g., corner clips, screws, bolts, mechanical snaps, etc.). To prevent fusion of two structures, a spacer (e.g., rubber gasket) can be used between the two structures.

Figure 6:
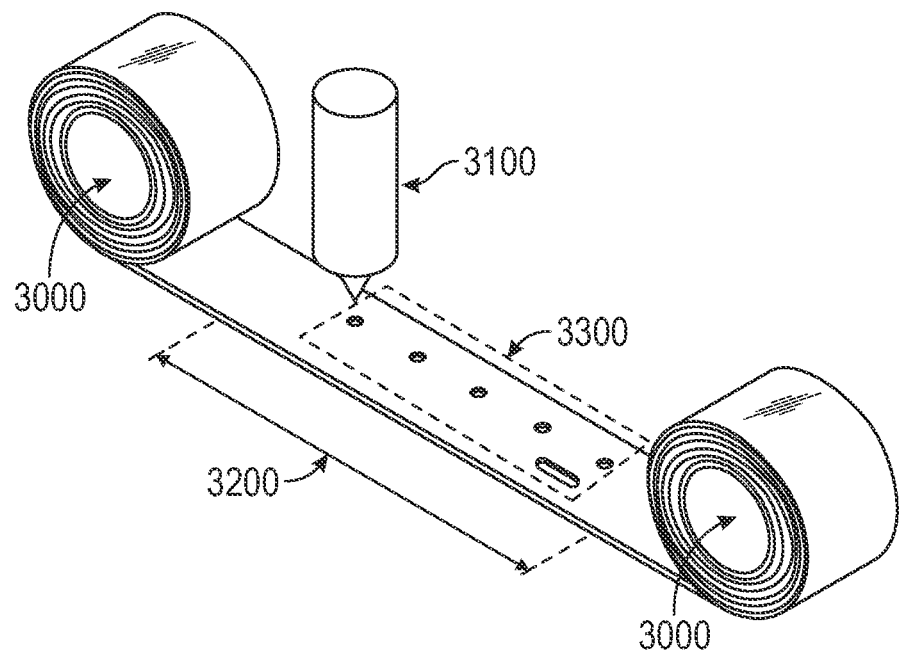
FIG. 6 shows a diagram of a reel-to-reel process for making a cylindrical flat glass structure.

In another embodiment, the single or multi-layer, flat glass structure is a patterned, multilayer roll of flat glass that is formed from a first roll of flat glass that is unrolled from a first spool, optionally cut (patterned), and then rolled onto a second spool to form a unitary cylindrical structure that is patterned, multi-layer of flat glass as shown in FIG. 6. In this aspect, each "layer" as described above is a singular turn of glass in the patterned, fused, multi-layer roll (as opposed to a single, separate length of glass).

In another aspect, the present invention provides a novel patterned, multi-layer, roll of flat glass: comprising a multi-layer roll of flat glass, comprising, at least a plurality of layers that are missing at least one portion of glass, wherein the layers of flat glass are fused together; and the roll is cylindrical. A layer is one turn or circumference of the cylinder. In addition, the cylindrical roll has a hollow (open) center (see FIG. 6). This opening can be equivalent to the diameter of a spool if one is used in the process of manufacture.

In another aspect, a plurality of portions of glass (cut-outs) are missing from a plurality of the layers (not shown). In another aspect, a plurality of the missing glass portions in the plurality of layers are aligned to form a channel(s) (e.g., via) and/or a chamber(s). In another aspect, the roll, comprises at least 10 layers. In another aspect, the roll, comprises at least 50 layers. In another aspect, the roll, comprises at least 100 layers.

An advantage of the cylindrical roll is that a "reel to reel" process can be shown in FIG. 6. The space between the reels is variable can be set based on the size and speed of the laser cutting 3100 and also if components are being deposited (e.g., metal deposition or soldering) onto the unrolled section prior to rolling onto the second reel.

Figure 7:
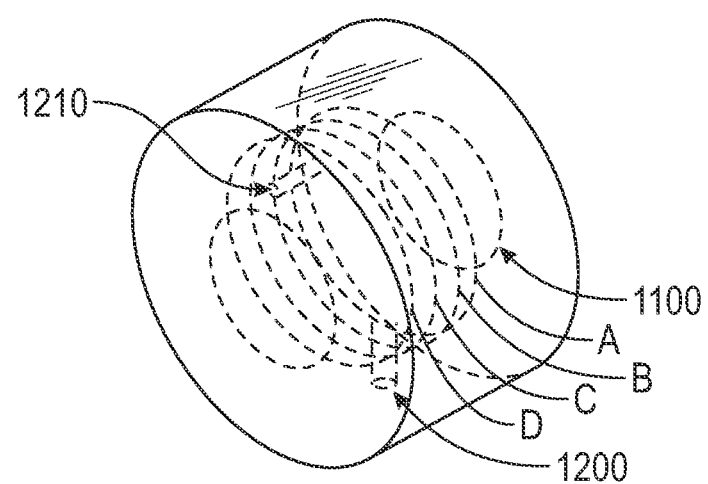
FIG. 7 shows a perspective view of a cylindrical, multi-layer, flat glass structure.

In another aspect, the present invention provides a novel method of manufacturing a cylindrical, multi-layer, flat glass structure, the method illustrated in FIG. 6 comprising a. unrolling a length 3200 of flat glass from a first spool 3000, comprising: a first roll of flat glass; b. optionally cutting a desired pattern 3300 into the length of glass; c. rolling the optionally cut length of glass onto a second spool 3000 to form a second roll; d. repeating steps (a)-(c) until the desired structure is formed by the second roll; and e. optionally, cutting away the remainder of the first spool from the second spool and optionally rolling any remainder onto the second roll, wherein at least one portion of glass is missing from a plurality of the layers. FIG. 7 shows a view of the unitary cylindrical, multi-layer flat glass structure after it is completed.

In the cylindrical structure, the flat glass has a plane curve shape (e.g., has been wound around a spool). In another aspect, the process of rolling the glass onto the second spool causes it to fuse to the adjacent layers A, B, C, D of the roll. In another aspect, the cylinder is formed from one, continuous piece of flat glass. In another aspect, the cylinder comprises flat glass having a plurality of thickness (e.g., 2, 3, 4, 5, or 6 different thickness). For a cylinder with a plurality of thicknesses, the first thickness comes from the first roll used to make the cylinder, the second thickness comes from a second roll, the third thickness, if present, comes from a third roll. This is accomplished by using a first roll, then continuing the rolling with the next roll. The ends of the first roll and beginning of the next roll can be touching or a space can be left. This is repeated for each subsequent roll. The remainder of the description of non-cylindrical multi-layer, flat glass structures applies to the cylindrical structures (except where incompatible with a cylindrical structure).

Figure 8:
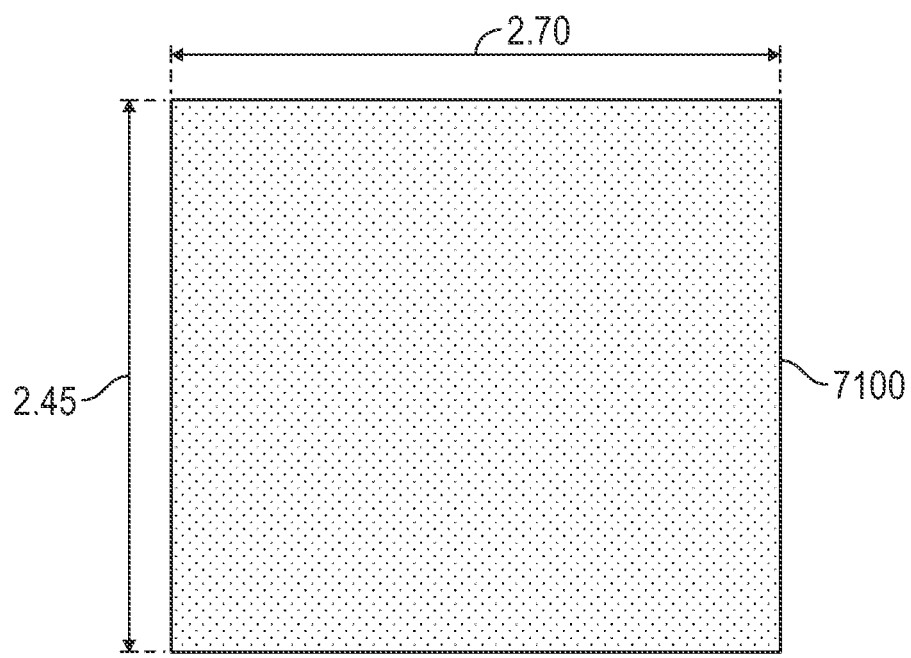
FIG. 8 shows sample dimensions in mm of a piece of flat glass.
Figure 9:
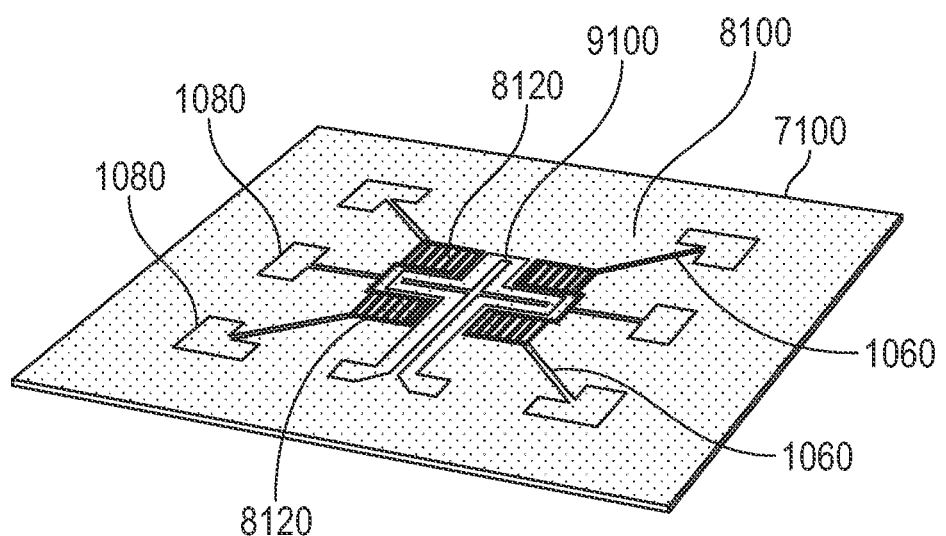
FIG. 9 shows an embodiment of single layer flat glass sensor structure.
Figure 10:
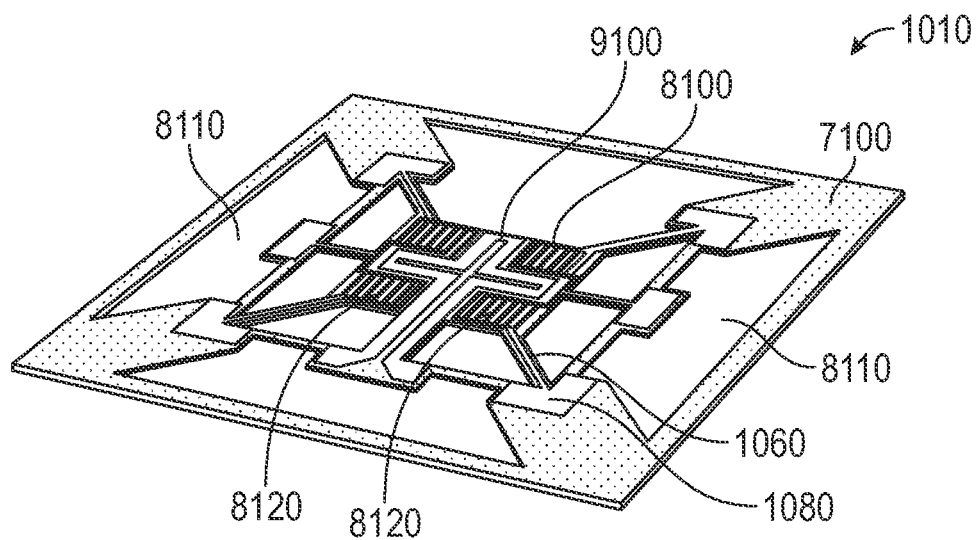
FIG. 10 shows an embodiment of single layer flat glass sensor structure with cutouts and a heating element on the flat glass layer.

FIG. 8 shows sample dimensions of a piece of flat glass 7100. FIG. 9 shows an embodiment of single layer flat glass 7100 with sensor 8100. FIG. 10 shows a single layer glass sensor structure 1010 comprising a single layer flat glass 7100 with a plurality of cutouts 8110, a sensor 8100 and a heater 9100. The cutouts 8110 increase temperature insulation and isolation of the sensor 8100. In other words, removal of the glass near the edges of the sensory element helps to isolate the sensor from the glass-sensor structure. Isolating the sensor can provide benefits such as thermal stability and decreased power consumption. In one embodiment, the flat glass 7100 comprises a reflective surface on its top or bottom; and, a sensory element.

In one embodiment shown in FIG. 10, the glass-sensor structure 1010 is hereafter interchangeably referred to as "Layer A" 1010 comprising the flat glass 7100 with cutouts 8110, sensor 8100 and heater 9100. In one embodiment shown in FIG. 10, the single glass-sensor structure 1010 is a unitary structure and/or device. In one embodiment shown in FIG. 11A, the glass-sensor structure further comprises from 1-4 additional glass Layers B 1020, Layer C 1030, Layer D 1040 and/or Layer E 1050 which are directly or indirectly in contact with Layer A 1010 forming a multi-layer glass-sensor structure 8185 is a unitary structure and/or device 8185.

In one embodiment, Layer B 1020 is a flat glass layer located on top of and at least partially in contact with Layer A 1010. Layer C 1030 is a flat glass layer located on top of and at least partially in contact with Layer B 1020, if present, or Layer A 1010. Layer D 1040 is a flat glass layer located on the bottom of and at least partially in contact with Layer A 1010. Layer E 1050 is a flat glass layer located on the bottom of and at least partially in contact with Layer D 1040. In one embodiment shown in FIG. 11A, FIG. 11B and FIG. 12A, the multi-layer glass-sensor structure 8185 is a unitary structure and/or device.

In another aspect, the present invention provides a novel glass-sensor structure, wherein Layer A 1010 comprises a plurality of sensors. Examples of plurality include 2, 3, 4, 5, 6, 7, 8, 10, 11, 12, 13, 14, 15, 16, 17, 18, 19, 20, 21, 22, 23, 24, 25, 26, 27, 28, 29, 30, 32, etc. The number of sensors on Layer A 1010 is only limited by the starting size of Layer A 1010 and the size of each individual sensor. A single layer glass sensor 1010 comprising a plurality of sensors, can be cut into multiple sensor glass layers and or unitary devices. For example, if there are 64 sensory elements on Layer A 1010 then this structure can be cut into 16 glass sensor layers, each with 4 sensors thereon. In another example, the 64-sensor structure can be cut into 4 glass sensor structures each with 16 sensory elements. In another example, the 64-sensor structure can be cut into 64 sensor glass layers, each with 1 sensor. In another aspect, parts of a sensor can be present on the top, bottom or in plane with the flat glass layer 7100 in a single layer glass sensor structure 1010 or a multi-layer glass sensor structure 8185.

In one embodiment, the present invention provides a novel glass-sensor structure, wherein the sensory element is in contact with at least a portion of the top of Layer A 1010 and has a smaller surface area than Layer A 1010. In another aspect, the sensory element is built directly onto the top of Layer A 1010. In another aspect, the sensory element is attached (e.g., glued) to the top of Layer A 1010. In another aspect, a middle portion of Layer A 1010 located under the sensory element is absent.

Figure 11A:
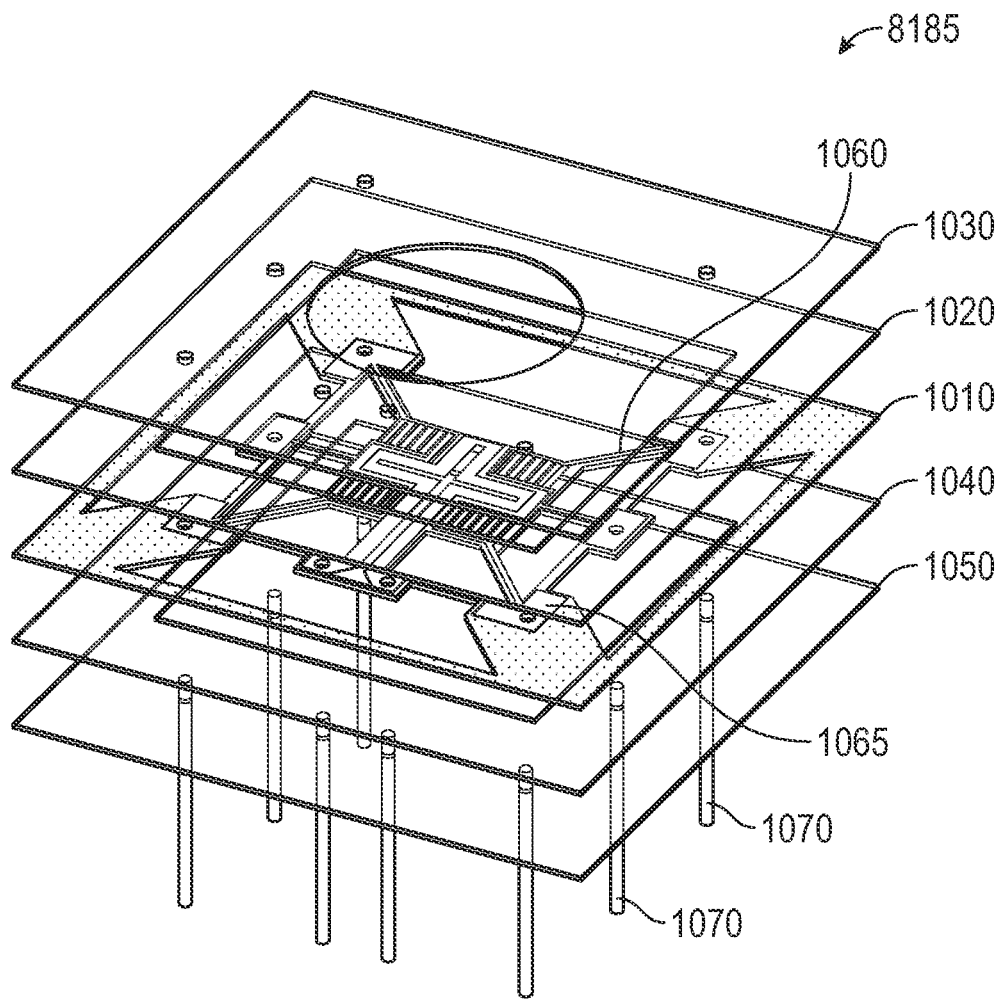
FIG. 11A shows an expanded view of an embodiment multi-layer flat glass sensor structure.

In one embodiment, the present invention provides a novel glass-sensor structure, wherein Layers B 1020 and C 1030 are present. As shown in FIG. 11A, a middle portion cutout 8100 of Layer B 1020 and/or Layer C 1030 is absent, such that an inner portion of Layer B 1020 is near the edges of the sensory element. Typically, when the sensor is on top of Layer A 1010, Layer B 1020 is not in contact with the sensor. In another aspect, there is a least one channel in Layer B 1020 (and/or Layer E 1050 when present) from an outside edge through to an absent middle portion. This channel forms an environmental connection and allows for gasses to flow into or out of the space between layers A 1010 and C 1030 (and/or A 1010 and E 1050), which is formed by the absence of a middle portion cutout 8110 of Layer B 1020 and/or Layer D 1040.

In another aspect, the present invention provides a novel glass-sensor structure, wherein a middle portion of Layer C 1030 is absent. A middle portion of Layer C 1030 being absent connects the sensor 8100 to the environment when the absent portions of Layers and B 1020 and C 1030 at least partially overlap. In another aspect, the reflective surface is present on Layer C 1030. In another aspect, the reflective surface is on top of Layer C 1030. In another aspect, the reflective surface is on bottom of Layer C 1030. One of ordinary skill in the art can configure the multiple layers with sensor location, cutouts, ports and or channels as required for a specific device and or system.

In one embodiment, the present invention provides a novel glass-sensor structure, wherein the sensor is in the same plane as Layer A 1010 and is housed in an opening in the middle of Layer A 1010 that is at least the size of the sensor. In this aspect, Layer A 1010 "houses" the sensor by having an opening in it that is large enough to fit the sensor. This opening can be just large enough to fit the membrane (e.g., at least the size of the sensor sub-areas 8120) or large enough that the sensor 8100 contacts the flat glass 7100 only through the glass connectors 1060.

In another embodiment, the membrane contacts the flat glass 7100 via the heater 9100. That is the heater 9100 is in direct contact with the flat glass 7100 and the membrane is in contact with the flat glass 7100 directly through the glass connectors 1060 and indirectly via the heater 9100. In one embodiment, the heater 9100 is in direct contact with the flat glass 7100 but not directly contact with the sensor 8100. The sensor 8100 can be indirectly heated via the flat glass 7100.

FIG. 11A shows one embodiment in which Layer A 1010 has one or more (e.g., a plurality of) contact points 1065 with the flat glass 7100. In one embodiment, these contact points 1065 are edge-to-edge contact points (i.e., an edge portion of sensor 8100 with an edge portion of the flat glass 7100). For example, an edge of a protrusion or tab in the middle of the flat glass 7100 can be in contact with an edge of the sensor 8100 (not shown). Examples of the number of these contact points include 1, 2, 3, 4, 5, 6, 7, 8, 9, 10, or more. The contact can also be continuous. For example, one complete edge (e.g., one side of a square or rectangular shaped sensor) of the sensor can be in contact with an edge of flat glass 7100. In another example, all four edges of a square, rectangular, or similarly shaped sensor, can be in contact with a flat glass layer 7100. In one embodiment, the above can readily be applied by substituting flat glass layer 7100 with Layer A 1010 and/or any of the Layers B 1020-E 1050. That is placing any sensor 8100 in plane with Layers A 1010, B 1020, C 1030, D 1040, and/or E 1050 or any combination of Layers A 1010, B 1020, C 1030, D 1040 and/or E 1050 are embodiments contemplated by the present invention.

One of the problems encountered when sensors are placed in the real world is damage caused to the sensor by the environment. The damage can be caused by weather (e.g., rain or humidity), dust, light, etc. A way to prevent, slow, or limit sensory element damage is to limit its exposure to the environment. Exposure of the sensor to its surrounding environment can be limited by one of Layers B, C, D, and/or E acting as a "cover" for (or "covering") the sensory element. Covering can be achieved by one of Layers A, B, C, D, and/or E being movable. Thus, in another aspect, at least one of Layers A, B, C, D, and E and/or any combination of these Layers is movable.

Movement may be by rotation, side-to-side motion (e.g., a layer slides in one direction to expose the sensory element to the environment and back to close) and/or up and down motion (e.g., a layer (or an edge thereof) lifts are raises far enough to allow environmental exposure and then settles back down to close). There are numerous ways to drive movement. For example, the movement can be driven by a lever, piezoelectric, magnetics, etc. In addition, the glass-sensor structure itself can be moved (e.g., tilting or shaking or inverting) to expose the sensor.

In another aspect, the present invention provides a novel glass-sensor structure as described above, further comprising: a plurality of mechanical pins 1070. In one embodiment, these mechanical pins 1070 pass through the middle layers of the glass-sensor structure and at least into the top and bottom glass layers. In another embodiment, one or more of the mechanical pins 1070 pass through at least one of the top or bottom glass layer and extend beyond the glass-sensor structure. A benefit of at least one or more pins 1070 extending beyond the structure (e.g., extending beyond the bottom glass layer) is that it allows for external electrical connection with the sensor 8100.

In another aspect, the mechanical pins 1070 are electrically conductive and are in electrical connection either directly or indirectly with the sensor 8100. In another aspect, the plurality of mechanical pins 1070 extend beyond the bottom glass layer 7100 of the glass-sensor structure, are electrically conductive, and are in electrical connection with the sensor 8100.

Figure 11B:
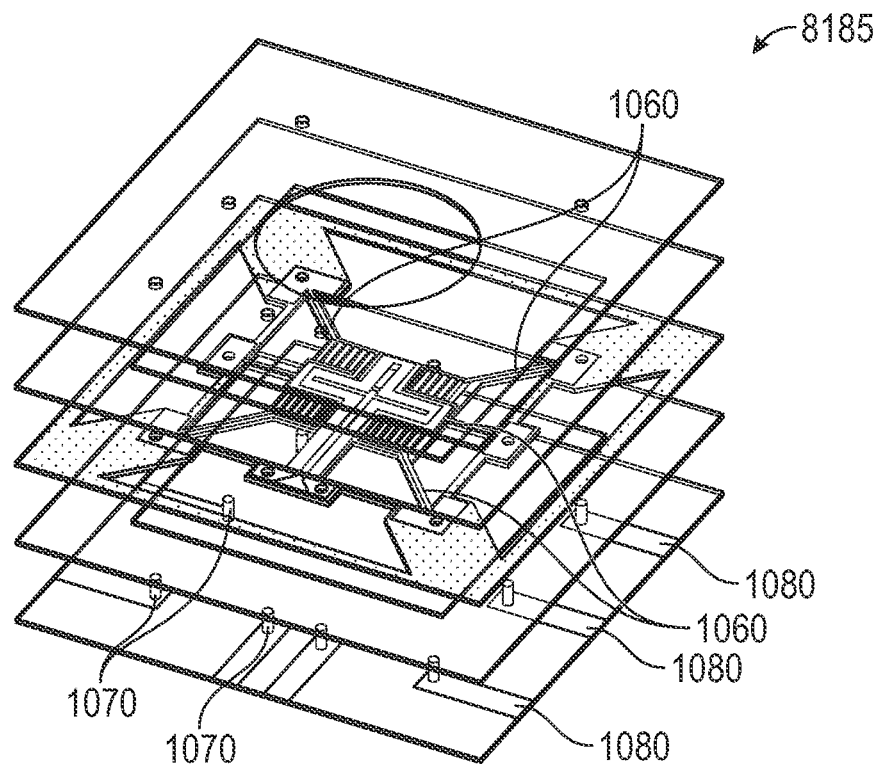
FIG. 11B shows an expanded view of an embodiment multi-layer flat glass sensor structure.
Figure 12A:
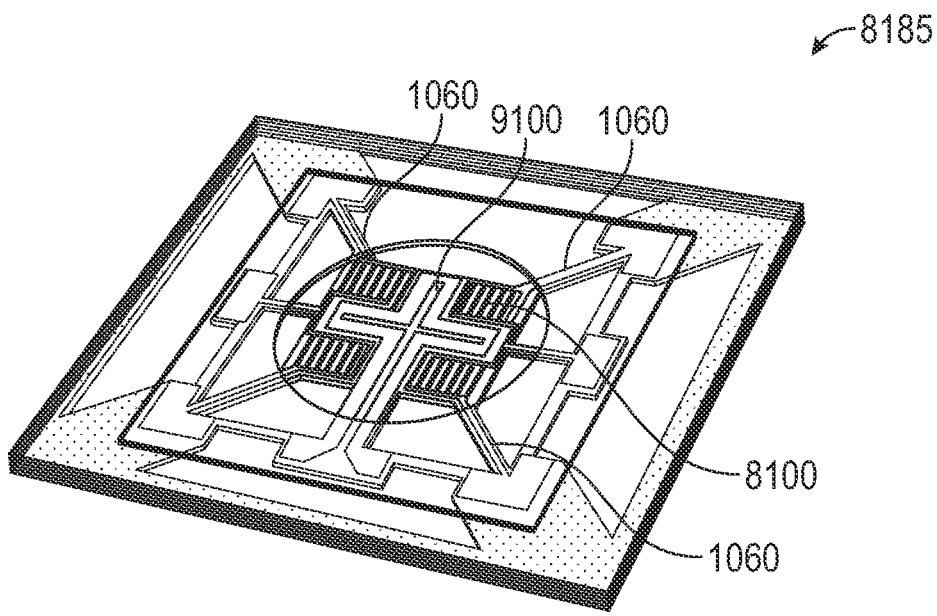
FIG. 12A shows a collapsed view of an embodiment multi-layer flat glass sensor structure.
Figure 12B:
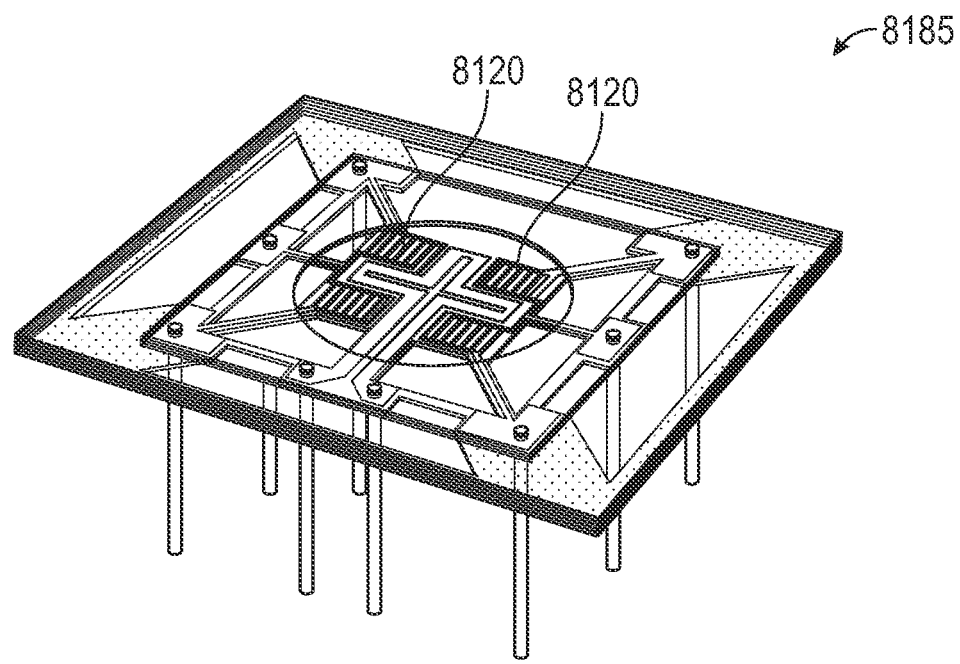
FIG. 12B shows a collapsed view of an embodiment multi-layer flat glass sensor structure.

FIG. 11B shows a novel glass-sensor structure as described above, further comprising a plurality of mechanical pins 1070 and a plurality of surface mount pads 1080, wherein the pads are located on top of the bottom layer (e.g., Layer E 1050) and are in electrical connection with the mechanical pins 1070. Typically, when surface mount pads 1080 are present, the mechanical pins 1070 are electrically conductive and pass into the outermost layers of the structure, but do not substantially extend beyond these outermost layers. The pins 1070 are useful as mechanical connectors and can facilitate the electrical connection of the sensor portion of the glass-sensor to external components (e.g., power source, detector, etc.). FIG. 12A is a collapsed view of a multi-layer glass-sensor structure 8185 of FIG. 11B. FIG. 12B is a collapsed view of the multi-layer glass-sensor structure 8185 with pins 1070 depicted by FIG. 11A.

The present disclosure describes the design and operation of a hand-held analytical Gas Chromatograph (GC). Some GC implementations may use scrubbed ambient air as carrier gas and 3-D printing or flat glass technology disclosed herein for components of the GC. In one embodiment, the 3-D printed portion of the device includes the chromatography column, the injector module, and a pre-concentrator (FIG. 13).

Figure 13:
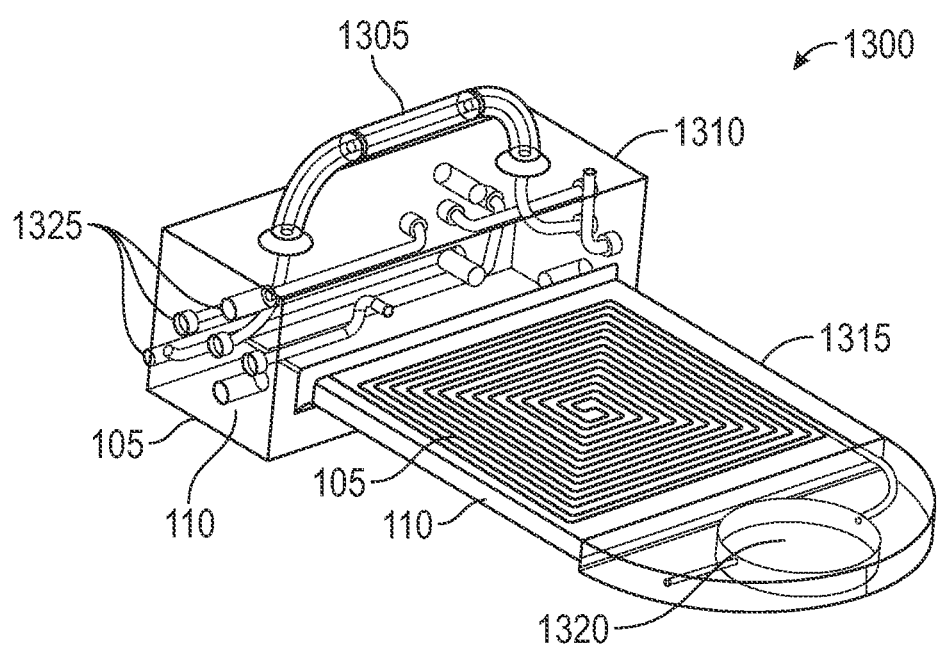
FIG. 13 shows a perspective view of a three-dimensional computer-aided design (3D-CAD) model of a gas delivery and separation system of a micro-GC.

FIG. 13 shows a perspective view of a three-dimensional computer-aided design (3D-CAD) model of a gas delivery and separation system of a micro-GC. In FIG. 13, the exemplary micro-GC 1300 includes the pre-concentrator 1305, the injector module 1310, the micro-column 1315, the flow cap 1320 for a sensor, and multiple chambers 1325. The multiple chambers 1325 are subsumed, or in other words, housed but not contained, by the injector module 1310. In the depicted example, the micro-column 1315 and the chambers 1325 are devices 110 disposed on or defined within the respective structures 105. In the illustrated example, the micro-column 1315 and the chambers 1325 are defined by apertures overlapping between abutting planar layers when the planar layers are stacked as depicted by FIG. 1. The micro-GC 1300 depicted by FIG. 13 may be constructed using 3-D printing glass/metal technology or punctuated layered glass technology disclosed herein.

In the example depicted by FIG. 13, the pre-concentrator 1305 is a short tube filled with sorbent material that absorbs molecules from a larger volume and then thermally desorbs them into a smaller volume. Heat and lower flow rate cause molecules to desorb at a higher concentration. The concentration is effectively the ratios of the two flow volumes if the trapping material is 100% efficient at trapping the molecules of interest. Traditional gas delivery systems for gas chromatographs may be assembled from pumps and valves, connected by stainless steel and plastic tubing. In one embodiment according to the present disclosure, a single compact 3-D printed glass/metal module (injector) replaces distributed tubing with a miniaturized system of channels inside the glass/metal block. Inlets and outlets of channels are threaded so pumps and valves can connect to the injector from outside. A miniature injector design can significantly reduce the size of the GC sampling system. FIG. 13 shows the three-dimensional computer-aided design (3D-CAD) model of the injector module 1310 as well as the printed prototype micro-GC 1300.

For trapping heavy hydrocarbons in oil and natural gas products, graphitized carbon material CARBOPACK B can be used as sorbent in pre-concentrators. For smaller molecules, such as ethylene, TENAX TA can be used as a pre-concentrator sorbent. TENAX TA is a porous polymer that has been used historically in many trap and purge applications.

In the chromatography column, the mobile phase (or carrier gas) carries the sample mixture through a stationary phase. The stationary phase is a chemical that can selectively attract components in a sample mixture. The mixture of compounds in the mobile phase interacts with the stationary phase. Each compound in the mixture interacts at a different rate. Those that interact the fastest will exit (or elute from) the column first. Those that interact slowest will exit the column last. By changing characteristics of the mobile phase and the stationary phase, different mixtures of chemicals can be separated. Typically, the light compounds propagate through the columns faster and have shorter retention times than compounds with high molecular weight.

Figure 14A:
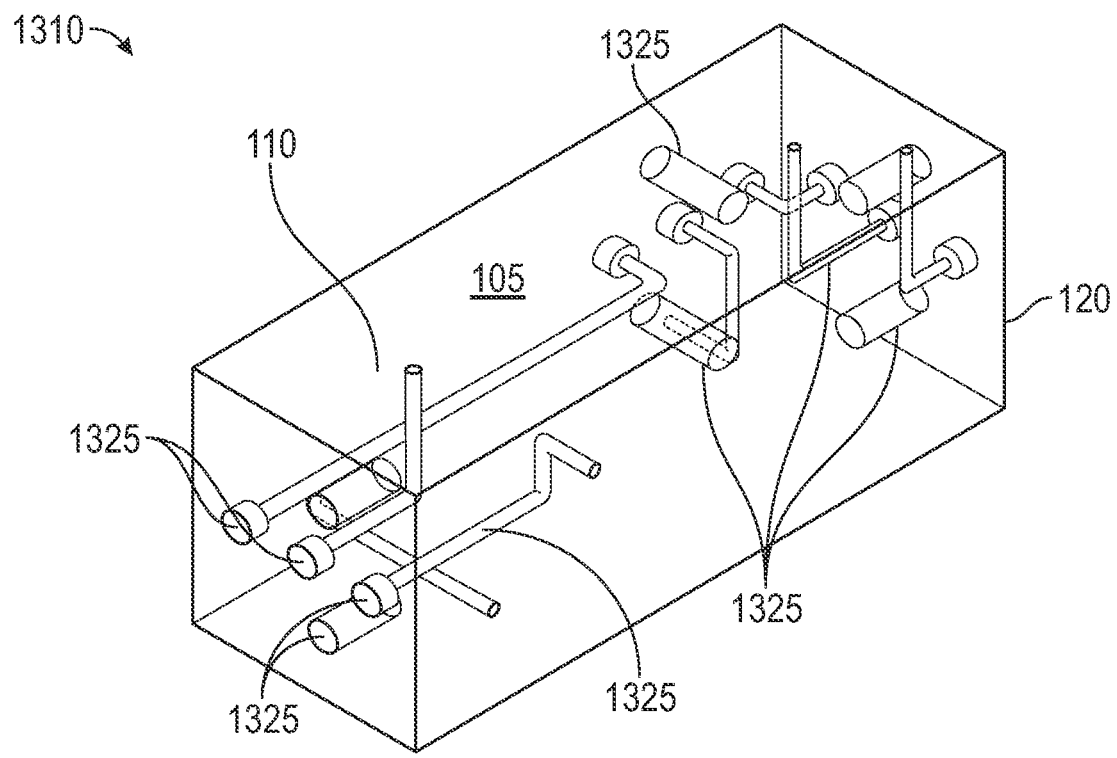
FIGS. 14A-B show perspective views of a 3-D model of an exemplary injector module.
Figure 14B:
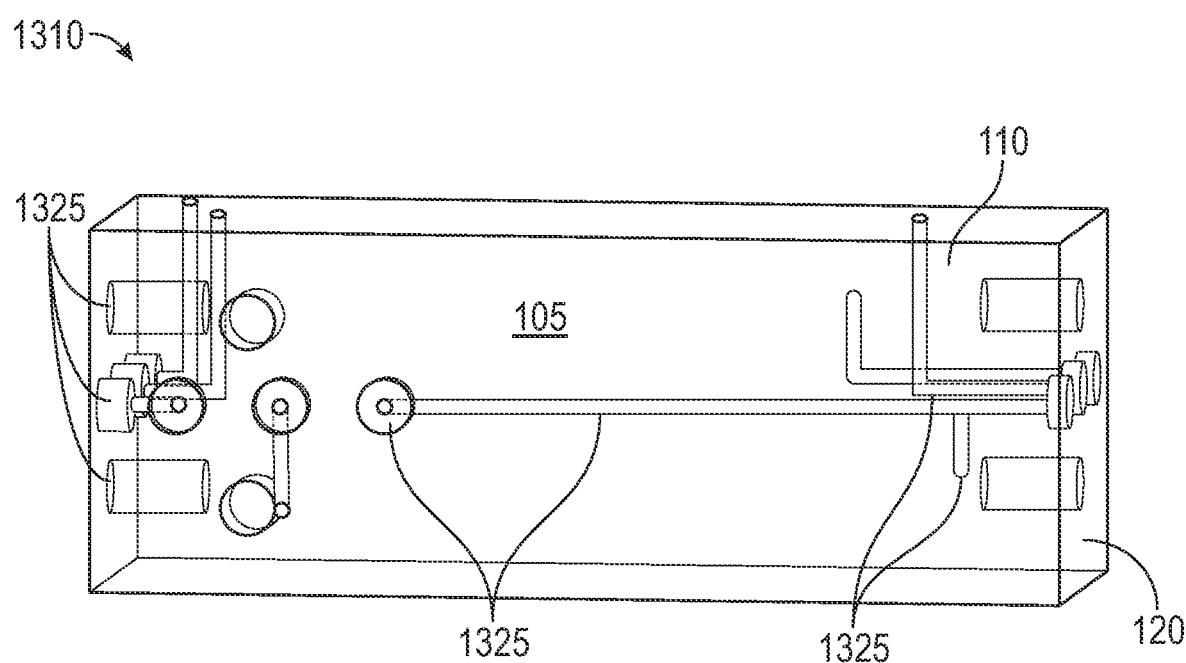
Figure 14C:
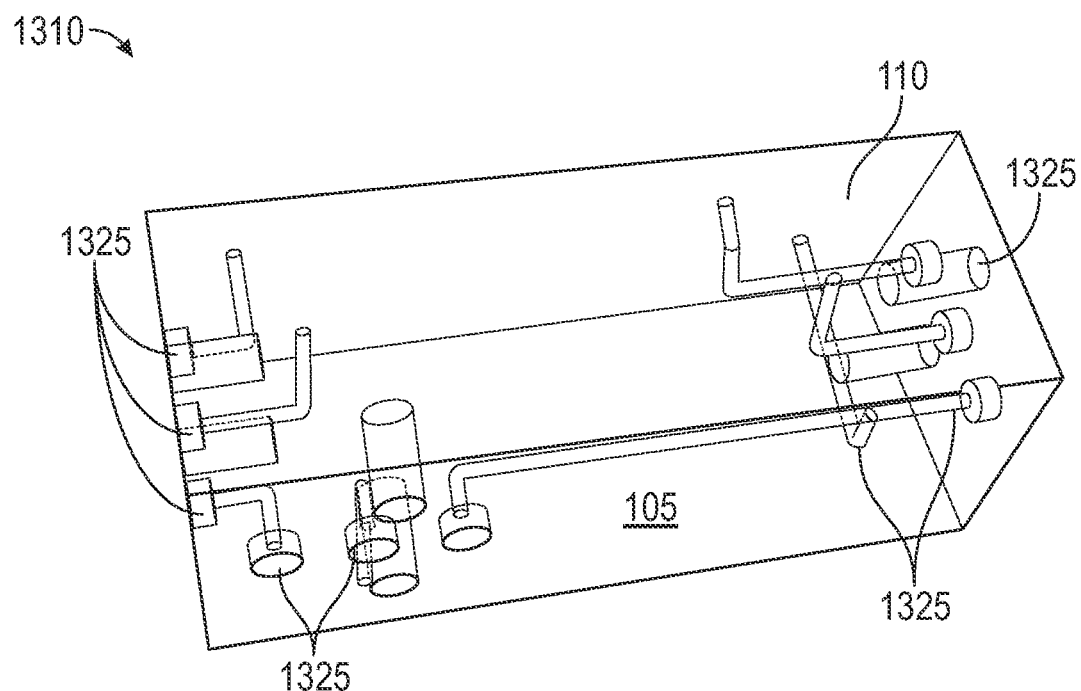
FIGS. 14C-F show perspective views of a clear resin 3-D print of an exemplary injector module.
Figure 14D:
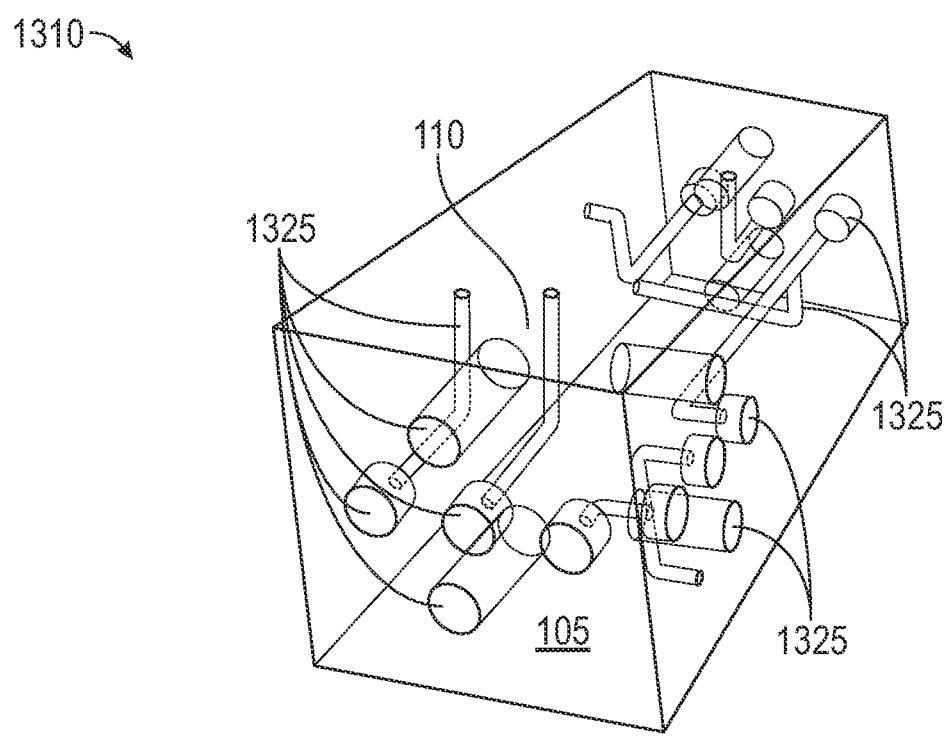
Figure 14E:
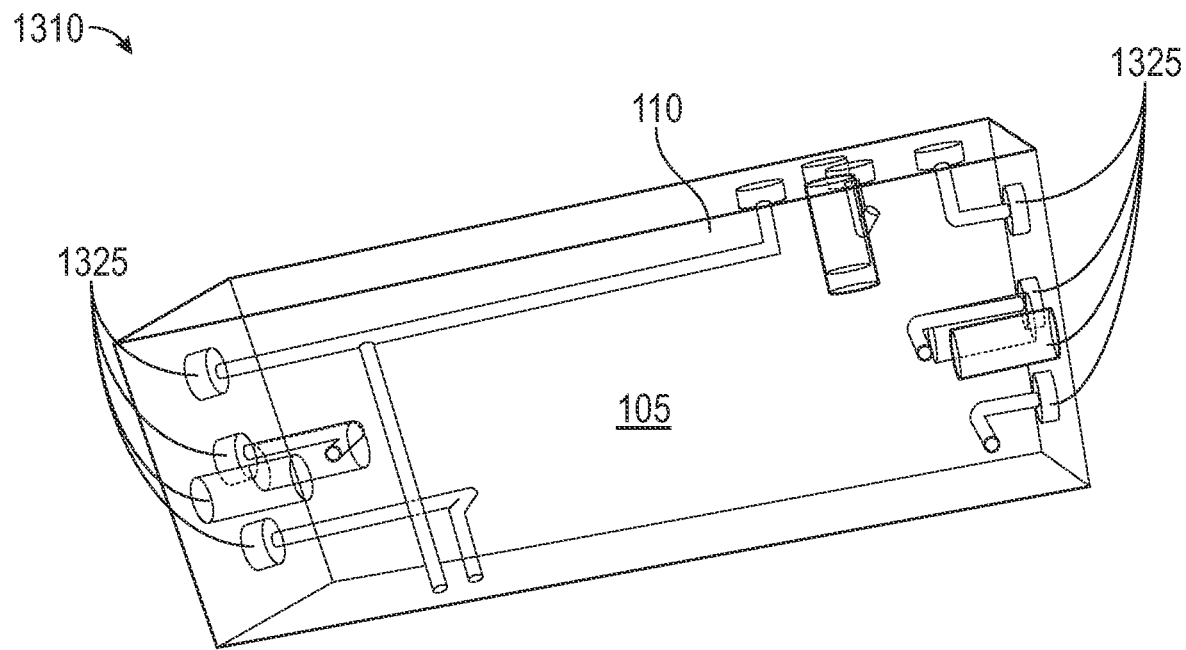
Figure 14F:
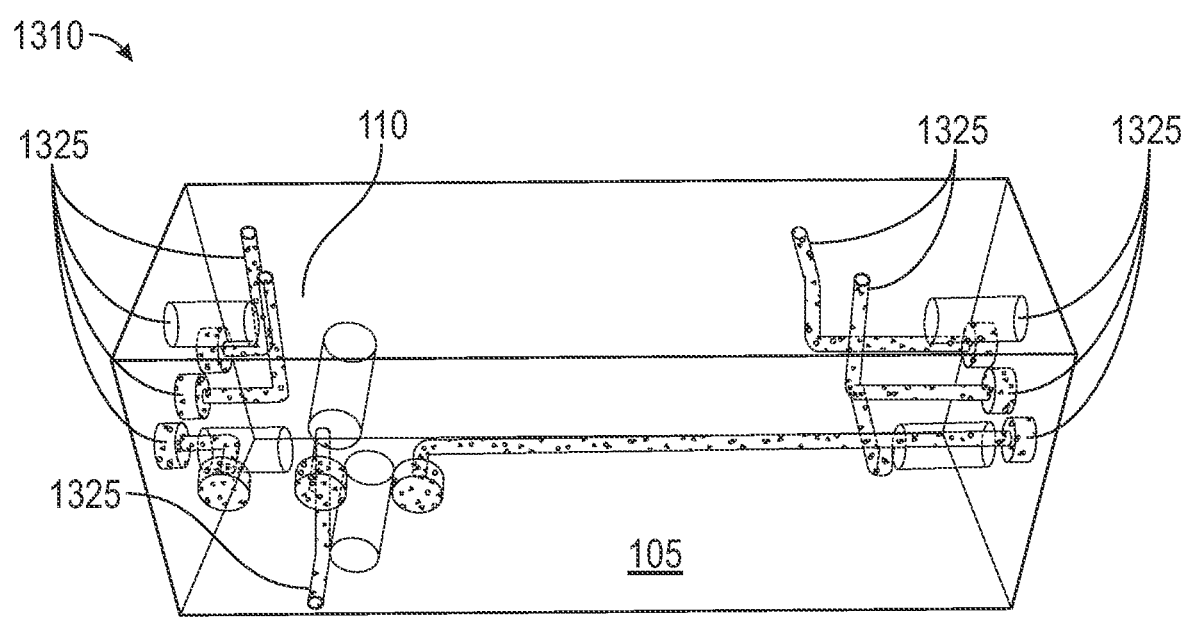
Figure 15A:
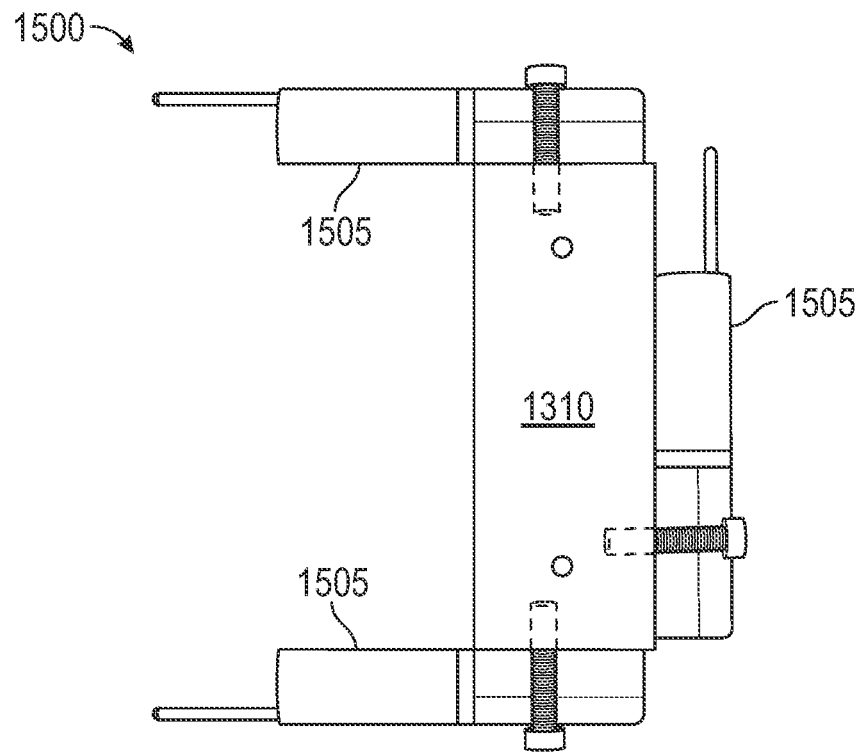
FIGS. 15A-E shows perspective views of a 3-D print of an exemplary injector module with attached micro-solenoid valves.
Figure 15B:
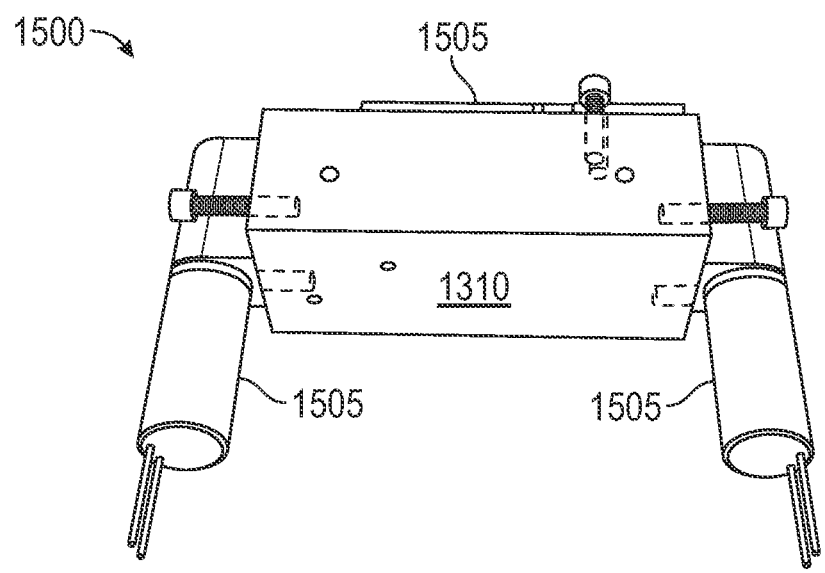
Figure 15C:
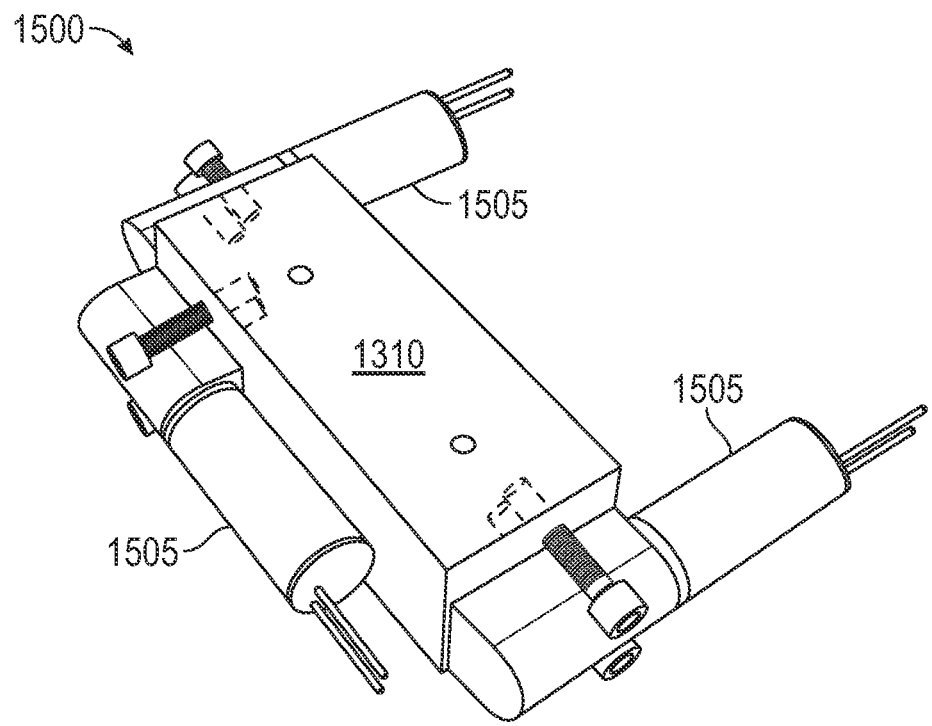
Figure 15D:
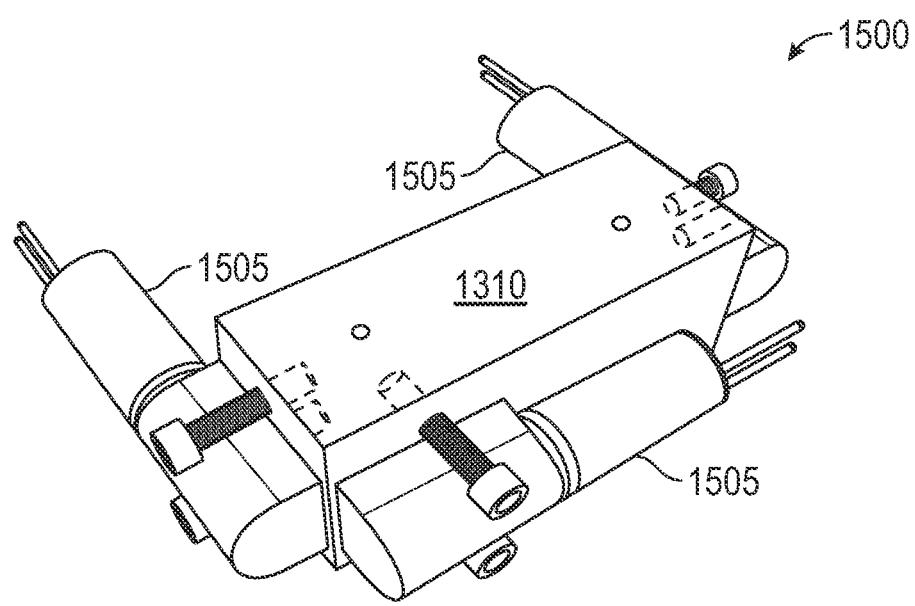
Figure 15E:
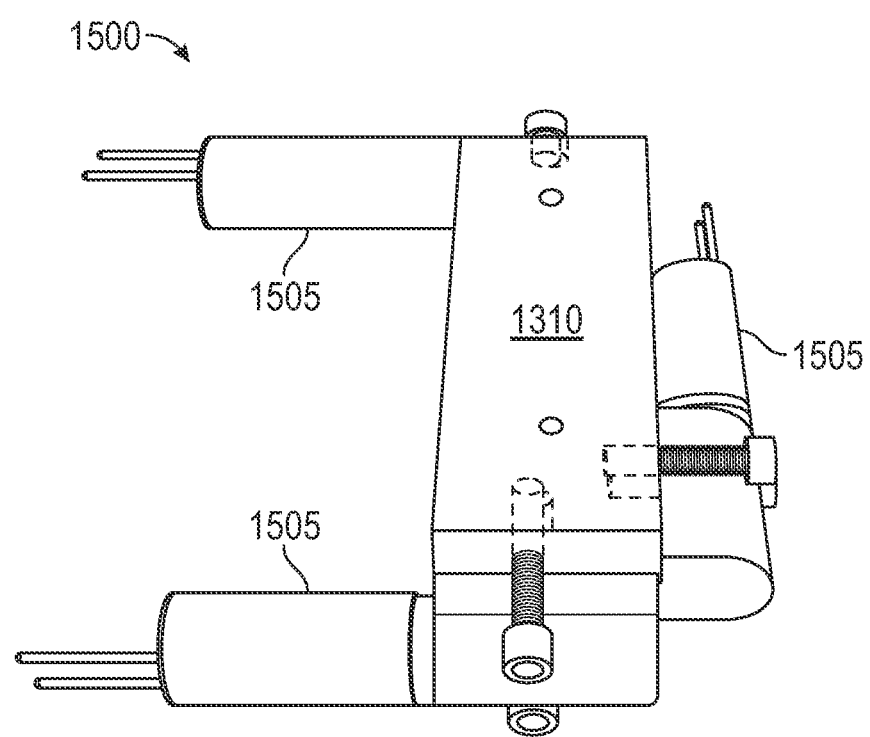

FIGS. 14A-B show perspective views of a 3-D model of an exemplary injector module. In FIGS. 14A-B, the exemplary injector module 1310 includes multiple chambers 1325. In the examples depicted by FIGS. 14A-B, the multiple chambers 1325 are devices 110 defined within the injector module 1310 structure 105 by apertures overlapping between abutting planar layers 120 when the planar layers 120 are stacked as depicted by FIG. 1 to form the injector module 1310.

FIGS. 14C-F show perspective views of a clear resin 3-D print of an exemplary injector module. In FIGS. 14C-F, the exemplary injector module 1310 includes multiple chambers 1325. In the examples depicted by FIGS. 14C-F, the multiple chambers 1325 are devices 110 defined within the injector module 1310 structure 105 by 3-D printing to form the injector module 1310.

FIGS. 15A-E shows perspective views of a 3-D print of an exemplary injector module with attached micro-solenoid valves. In FIGS. 15A-E, the exemplary injector module assembly 1500 includes the exemplary 3-D printed injector module 1310 configured with three micro-solenoid valves 1505.

Figure 16A:
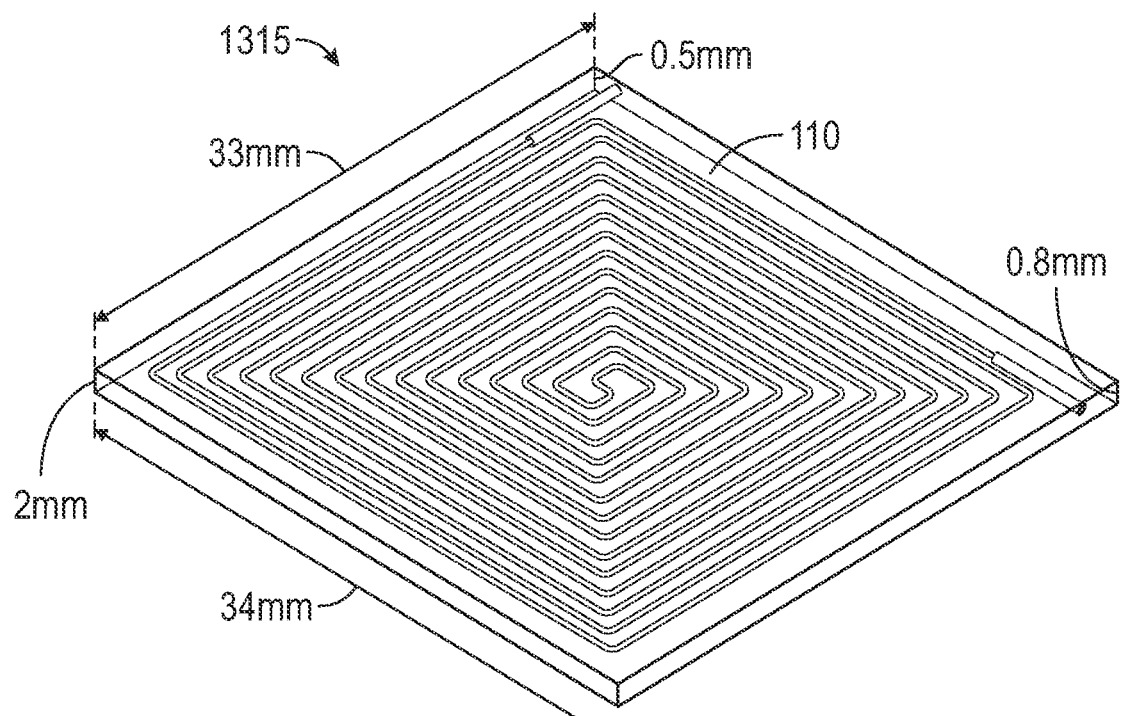
FIG. 16A shows a perspective view of a 3-D model of an exemplary GC microcolumn with sample dimensions in mm.

FIG. 16A shows a perspective view of a 3-D model of an exemplary GC microcolumn with sample dimensions in mm. In the example depicted by FIG. 16A, the exemplary GC micro-column 1315 is a device 110 defined by apertures overlapping between abutting planar layers when the planar layers are stacked to form the GC micro-column 1315. The exemplary GC micro-column 1315 is depicted by FIG. 16A with a square spiral one-meter-long column (3D-microcolumn) on a planar substrate of 34×33×2 mm. The GC micro-column 1315 may be 3D-printed followed by coating stationary phase onto the inner wall of the micro-channel.

Figure 16B:
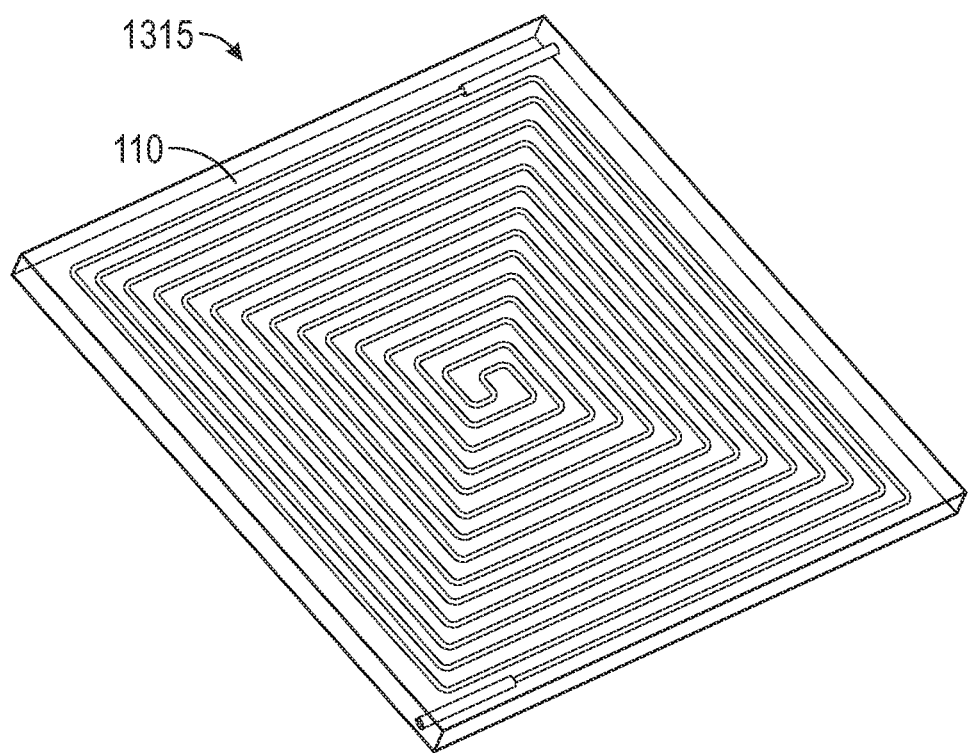
FIG. 16B shows a perspective view of a 3-D model of an exemplary GC microcolumn.

FIG. 16B shows a perspective view of a 3-D model of an exemplary GC microcolumn. In the example depicted by FIG. 16B, the exemplary GC micro-column 1315 is a device 110 defined by apertures overlapping between abutting planar layers when the planar layers are stacked to form the GC micro-column 1315.

Figure 16C:
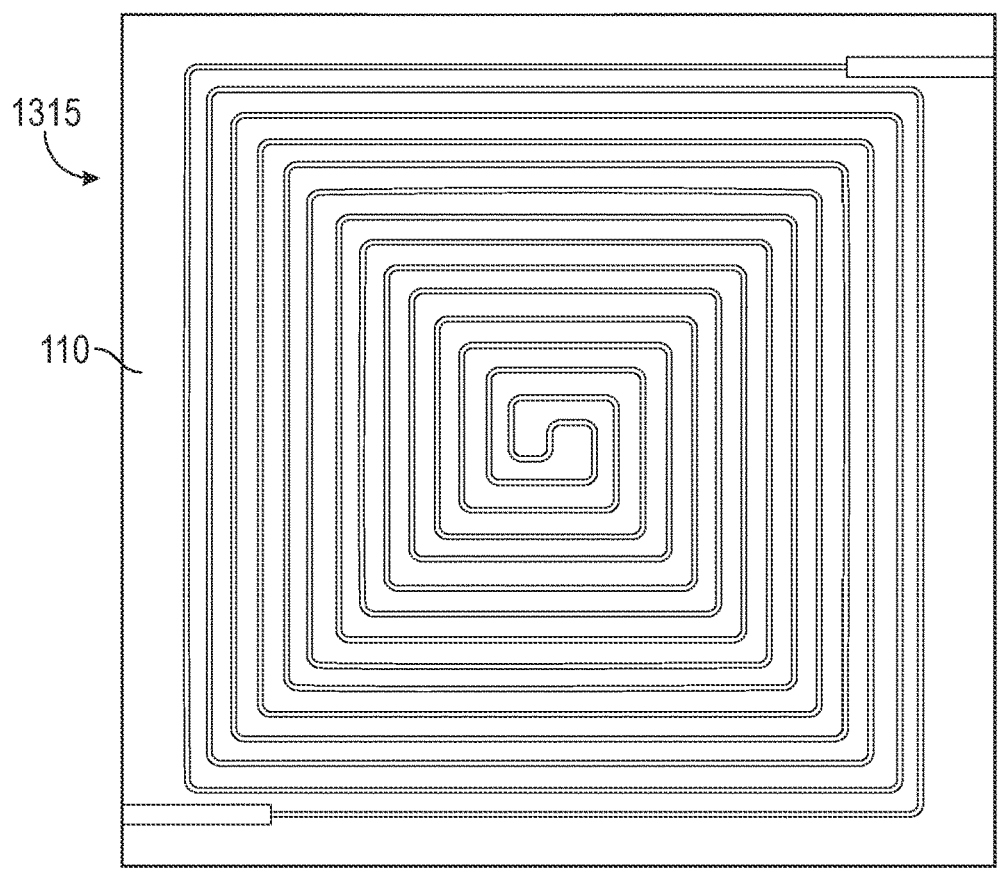
FIG. 16C shows a top view of a 3-D model of an exemplary GC microcolumn.

FIG. 16C shows a top view of a 3-D model of an exemplary GC microcolumn. In the example depicted by FIG. 16C, the exemplary GC micro-column 1315 is a device 110 defined by apertures overlapping between abutting planar layers when the planar layers are stacked to form the GC micro-column 1315.

Figure 16D:
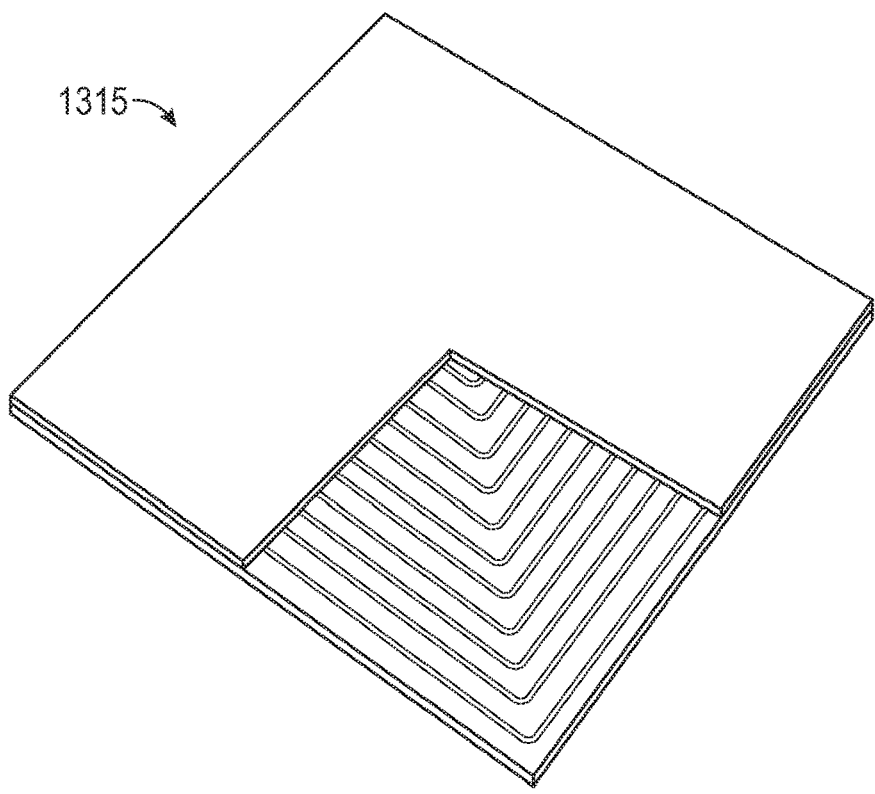
FIGS. 16D and 16E show two perspective views of a clear resin 3-D print of an exemplary GC microcolumn.
Figure 16E:
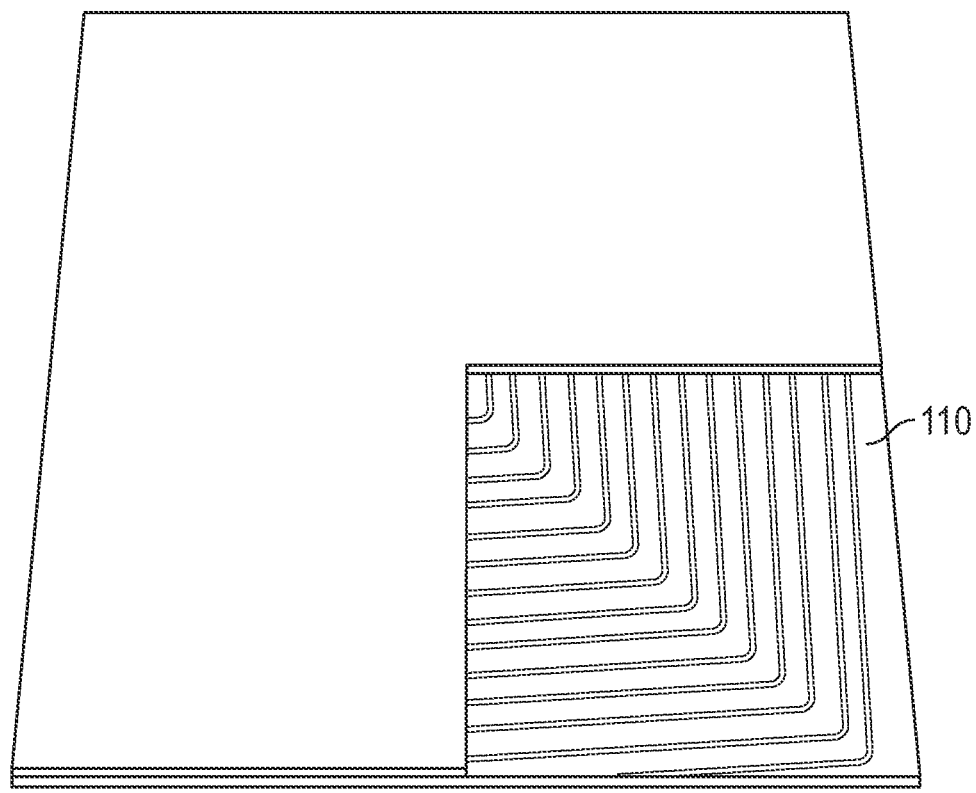

FIGS. 16D and 16E show two perspective views of a clear resin 3-D print of an exemplary GC microcolumn. In the examples depicted by FIGS. 16D-E, the GC micro-column 1315 is defined by 3-D printing.

Figure 17A:
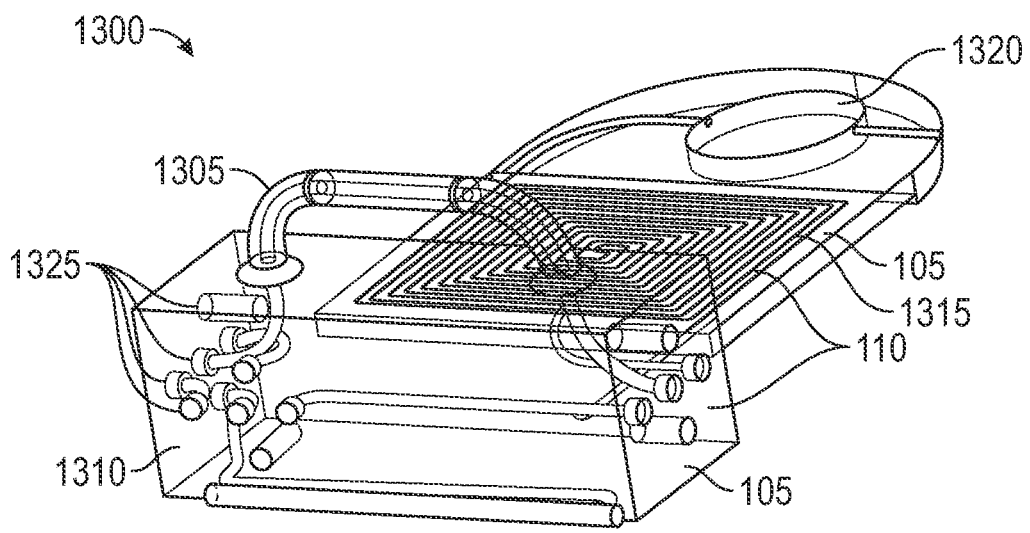
FIGS. 17A-C show perspective views of a 3D-CAD model of an exemplary gas delivery and separation system of an exemplary micro GC.
Figure 17B:
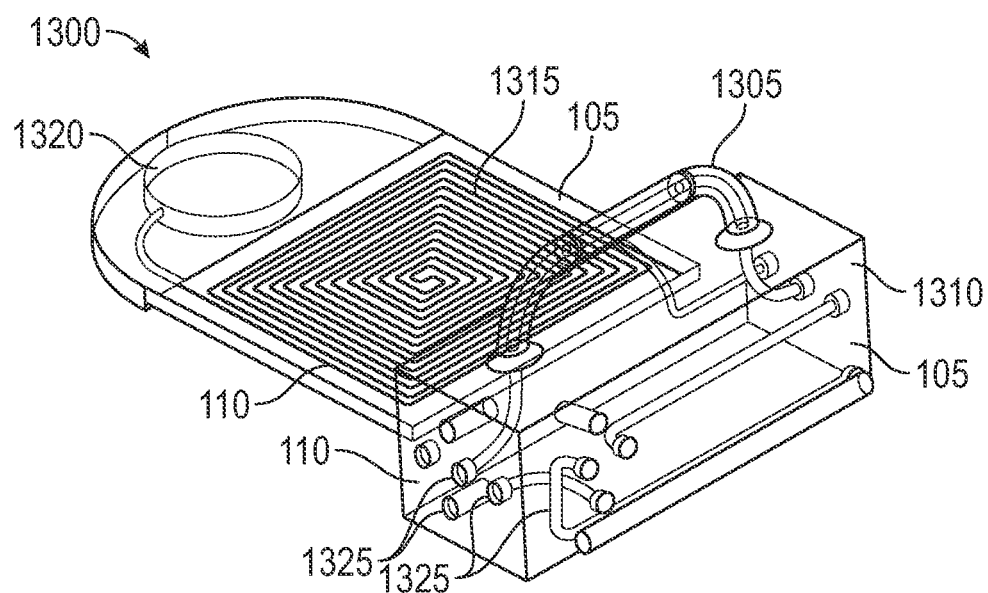
Figure 17C:
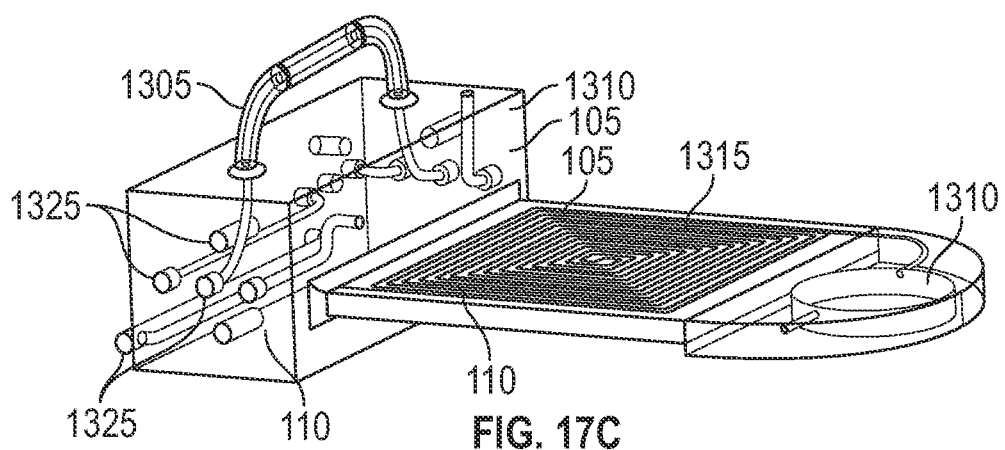

FIGS. 17A-C show perspective views of a 3D-CAD model of an exemplary gas delivery and separation system of an exemplary micro GC. In the examples depicted by FIGS. 17A-C, the exemplary micro-GC 1300 includes the pre-concentrator 1305, the injector module 1310, the micro-column 1315, the flow cap 1320 for a sensor, and multiple chambers 1325. The multiple chambers 1325 are subsumed, or in other words, housed but not contained, by the injector module 1310. In the depicted example, the micro-column 1315 and the chambers 1325 are devices 110 disposed on or defined within the respective structures 105. In the illustrated example, the micro-column 1315 and the chambers 1325 are defined by apertures overlapping between abutting planar layers when the planar layers are stacked as depicted by FIG. 1. The micro-GC 1300 depicted by FIGS. 17A-C may be constructed using 3-D printing glass/metal technology or punctuated layered glass technology disclosed herein.

Figure 18:
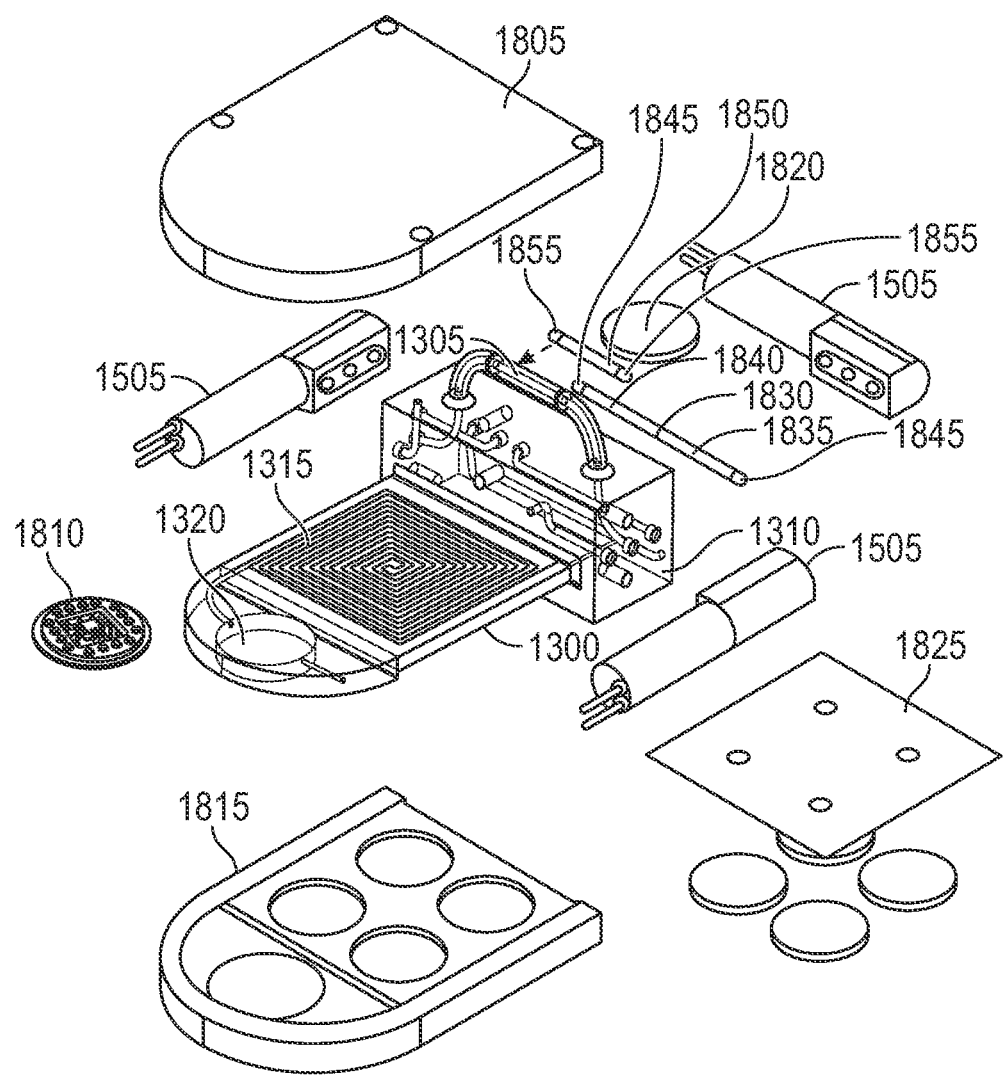
FIG. 18 shows an illustrative disassembled view of an exemplary GC column.

FIG. 18 shows an illustrative disassembled view of an exemplary GC column. In FIG. 18, the exemplary GC column 1800 includes the thermally insulated top housing 1805 and the thermally insulated bottom housing 1815 adapted with four recesses configured to support a column heater. In the illustrated example, the housing thermal insulation and thermostat temperature control help maintain the GC column 1800 at a desired temperature, while preventing heat dissipation. In the depicted example, the GC column 1800 includes the sensor array 1810, also depicted at least by FIGS. 22A and 22E. The sensor array 1810 may include multiple sensor 125 elements. In the depicted example, the GC column 1800 includes the PTC heater 1820 for the pre-concentrator 1305. In the illustrated example, the GC column 1800 includes the brass plate 1825 adapted to integrate the four column heaters depicted below the brass plate 1825. In the illustrated example, the GC column 1800 includes the scrubber 1830. In the illustrated example the scrubber 1830 includes the scrubber 1830 section 1835 configured with desiccant material designed to eliminate moisture. In the depicted example, the scrubber 1830 includes the scrubber 1830 section 1840 configured with activated charcoal for chemical filtration. In the illustrated example, the scrubber 1830 ends 1845 are configured with packed cotton fiber fill to eliminate dust or debris from an air stream. In the depicted example, the scrubber 1830 is a tube designed to eliminate moisture and contaminants from a carrier gas (air) stream. In the illustrated example the GC column 1800 includes the pre-concentrator 1305 having pre-concentrator main section 1850 configured with sorbent material. The pre-concentrator 1305 ends 1855 are configured with glass wool to prevent sorbent bleed into the GC column 1800 at high temperatures. In the depicted example, the GC column 1800 also includes three micro-solenoid valves 1505.

Figure 19:
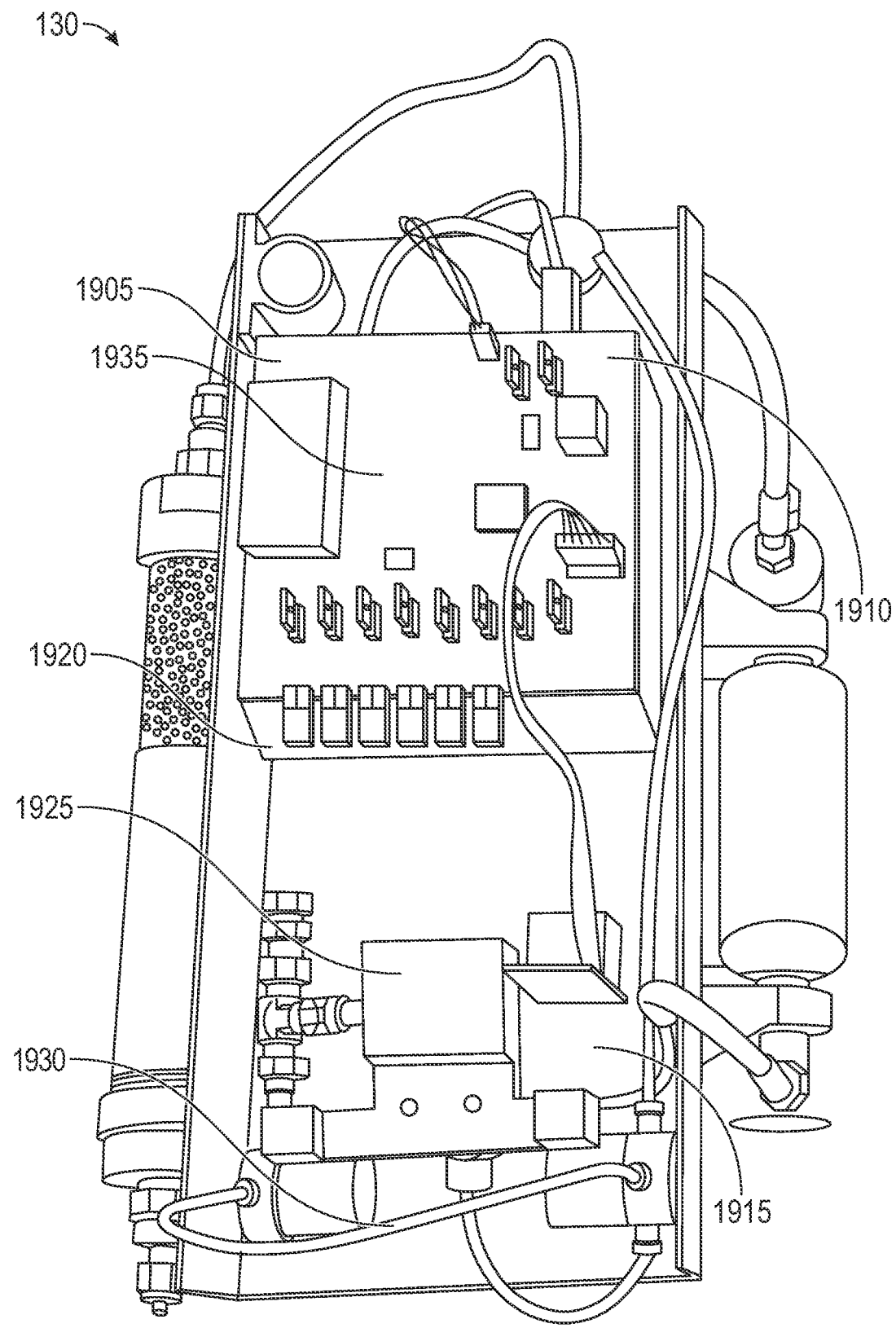
FIG. 19 shows a top view of an exemplary micro GC in an illustrative portable lab configuration.

FIG. 19 shows a top view of an exemplary micro GC in an illustrative portable lab configuration. In FIG. 19, the exemplary portable GC lab 130 includes the carrier gas generation pump 1905, the sample pump 1910, the detector module 1915, the GC column oven assembly 1920, the injector module with pre-concentrator and cooling fan 1925, the sampling input valve module 1930, and the microprocessor control board 1935. FIG. 19 shows a top view of the micro GC with the microprocessor Control board 1935 placed on top of the GC column oven assembly 1920 foam insulation. Various implementations are configured to use scrubbed ambient air as a carrier gas. The depicted analyzer's operating cycle includes: sampling, gas mixture separation, and detection. During the first step, the gas sample is injected in the system. The detection of gas components is performed by the array of sensors inside a low dead volume detector cell of 1 ml$^3$. After the analysis, the purging and cleaning cycle is applied to the systems to remove the leftover contaminants. This is an automatic function that is performed by the analyzer using its own generated clean air.

A sampling system of the analyzer is needed for quantitative determination of key target chemicals that are part of a complex gas mixture. A sample is collected and injected into a carrier gas stream, which is flowing through a chromatographic column. The column is either filled with a liquid coated support or a liquid coated on the walls of the tubing. The column has key physical properties that retard the movement of the sample though the column.

Chemical properties such as molecular weight and polarity slow the chemicals after interaction with the column support or liquid phase in comparison to the injection front. This results in the separation of the chemicals relative to the injection front and allows the individual analysis of the chemicals as they elute from the column into the detector assembly.

The MXT-WAX column is exemplary of an effective choice for this task as it is capable of separating the analytes of interest at a lower temperature than the other columns tested, 55° C., and it is stable over time with heating and the use of air as a carrier gas. The unit is designed to sample from a sampling port on the side of the instrument.

An exemplary schematic of the analyzer depicted by FIG. 19 is shown in operation by FIGS. 21A-F to describe the operating cycle. The portable gas chromatograph depicted by FIG. 19 was equipped with a MEGABORE Gas Chromatography Column: MXT-WAX, polyethylene glycol, 30 meters, 2 µm film thickness from RESTEK.

Figure 20A:
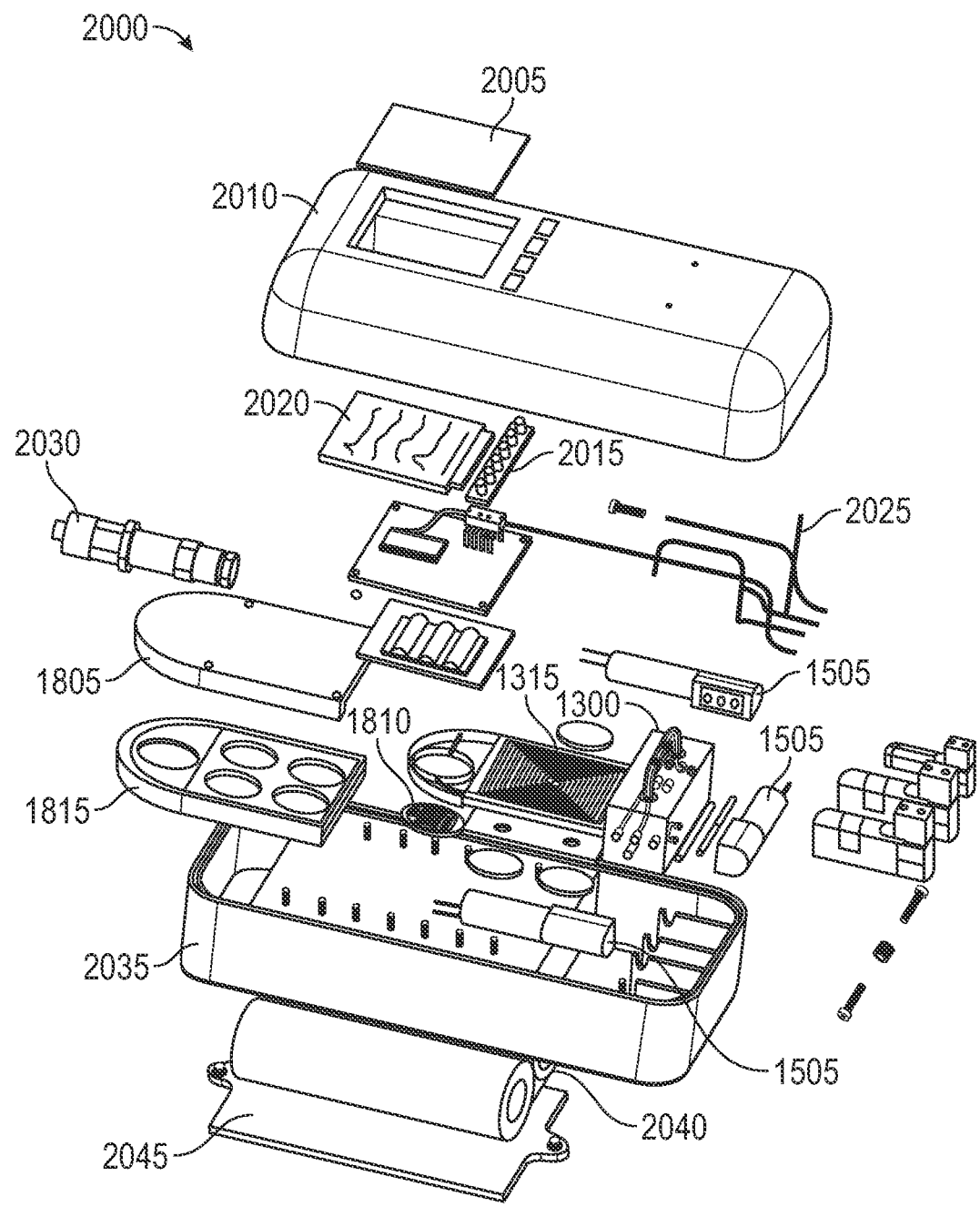

FIGS. 20A-F show various views of an exemplary micro GC in an illustrative hand-held configuration. In FIG. 20A, the exploded view 2000 of an exemplary micro-GC in an illustrative hand-held configuration includes the outer screen cover 2005, and the top case 2010. In the illustrated example, the hand-held micro-GC exploded view 2000 also includes the button pad 2015 configured for menu navigation and the OLED screen 2020 configured to display information to an operator. The depicted hand-held micro-GC example includes the stainless steel tubing 2025 configured to fluidly and operably couple the micro-GC 1300, the micro-solenoid valves 1505, and the micro-column 1315 with the sensor 1810. The illustrated hand-held micro-GC example includes the stainless steel sample fitting 2030 configured to connect a sample line to the hand-held micro-GC. The depicted hand-held micro-GC example also includes the bottom case 2035, the batteries 2040, the battery plate 2045, the thermally insulated top housing 1805, and the thermally insulated bottom housing 1815.

Figure 20B:
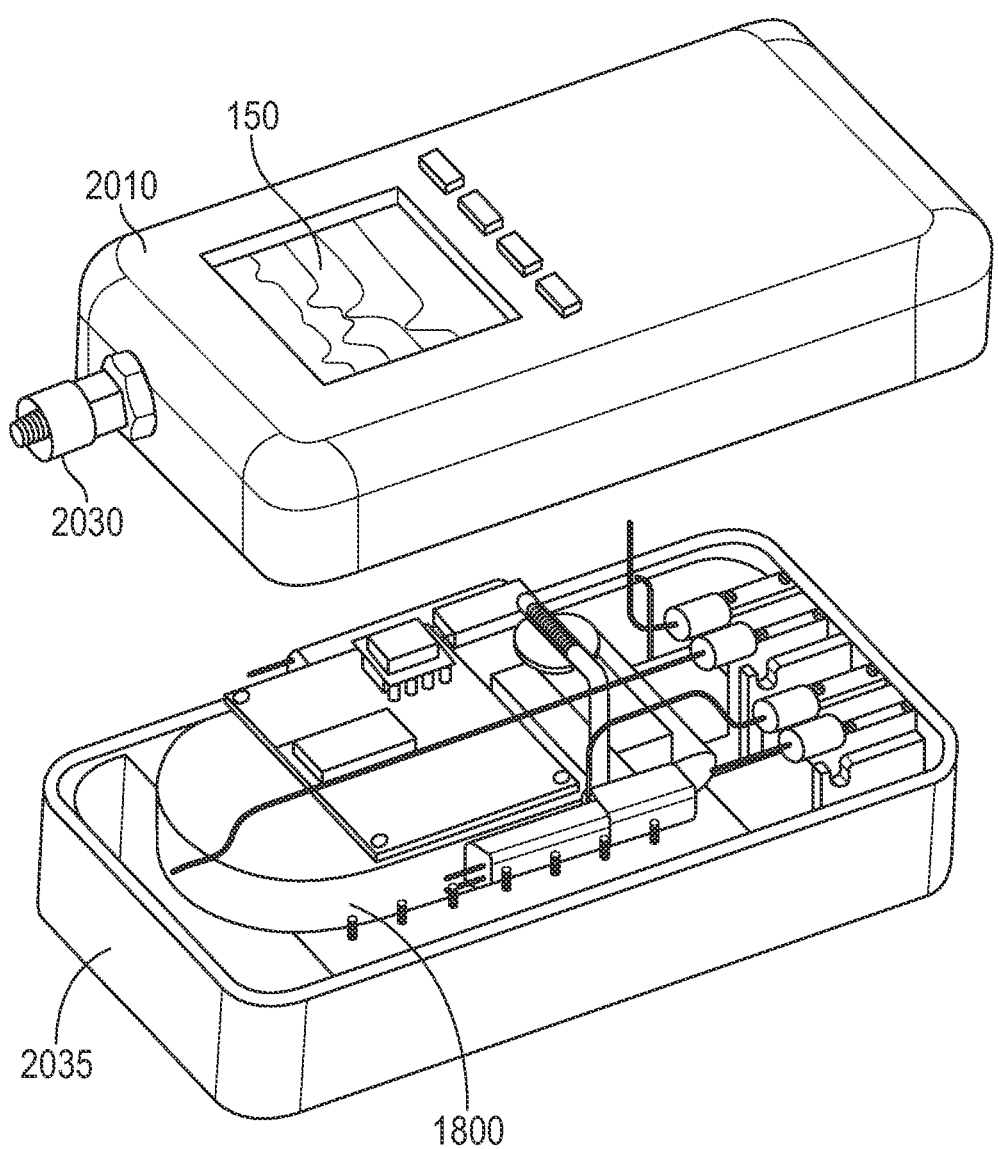

In FIG. 20B, the depicted exemplary hand-held micro-GC includes the user interface 150 also depicted by FIG. 1. In the depicted example, the user interface 150 is accessible by an operator through the top case 2010. The operator may connect a sample line to the hand-held micro-GC sample fitting 2030. The depicted hand-held micro-GC includes the GC column 1800, depicted by FIG. 18. In the illustrated example, the GC column 1800 is retained by the bottom case 2035.

Figure 20C:
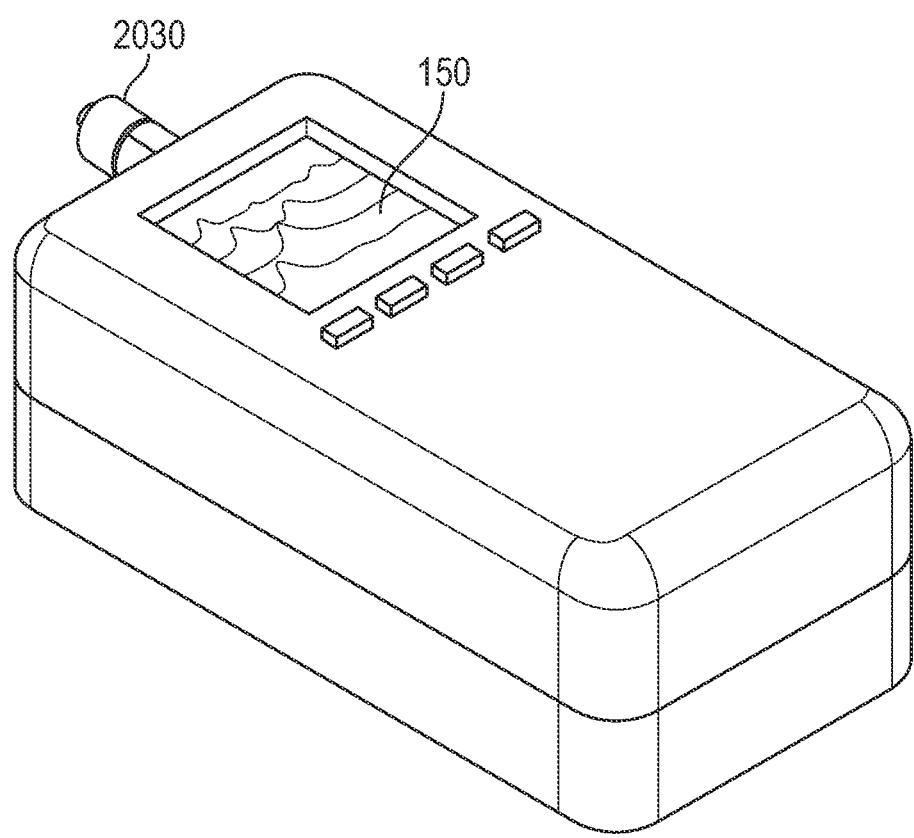

In FIG. 20C, the depicted exemplary hand-held micro-GC is illustrated in an assembled handheld GC 135 configuration, also depicted by FIG. 1. The illustrated exemplary handheld GC 135 includes the user interface 150 and the sample fitting 2030.

Figure 20D:
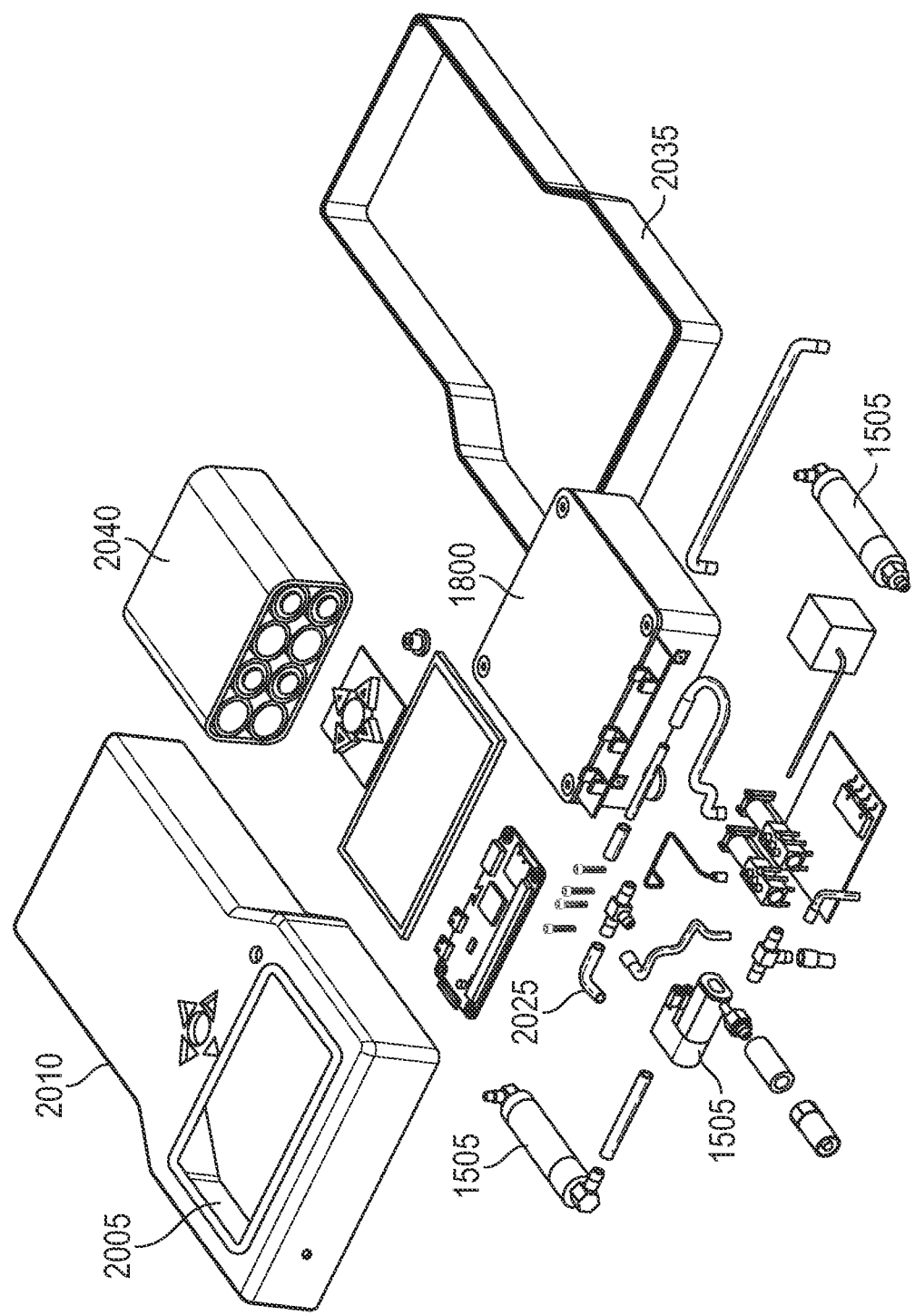

In FIG. 20D, the exemplary hand-held micro-GC illustrated in an exploded view includes the GC column 1800, the micro-solenoid valves 1505, the outer screen cover 2005, the top case 2010, the tubing 2025, the bottom case 2035, and the batteries 2040.

In FIG. 20E, one micro-solenoid valve 1505 is visible at each of the two sides of the depicted exemplary GC column 1800 front view.

Figure 20F:
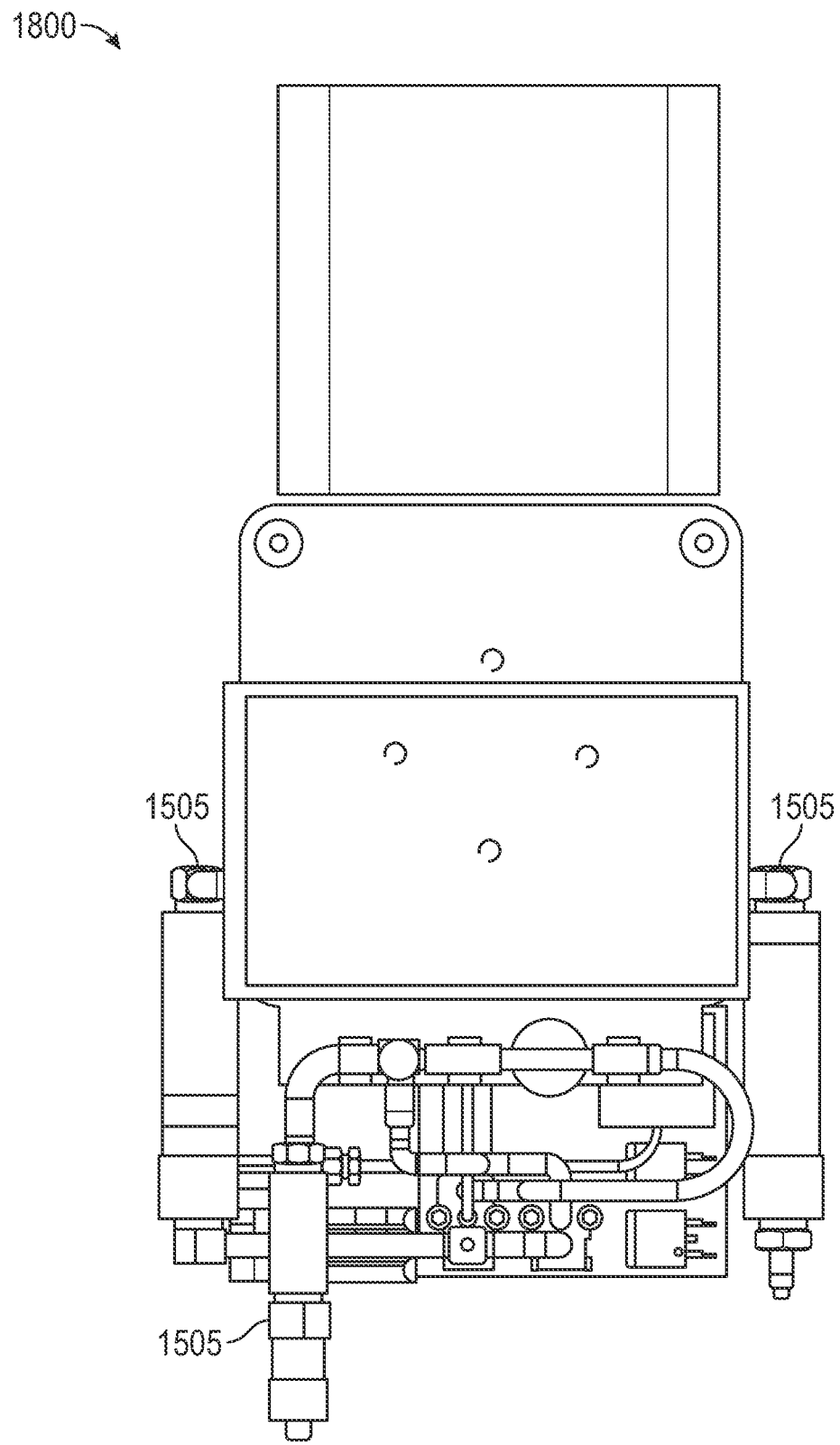

In FIG. 20F, the depicted exemplary GC column 1800 top view includes three micro-solenoid valves 1505.

In one embodiment, the flat glass technology described above can be used to create each of the micro-GC component parts illustrated at least by FIGS. 13-18. In one embodiment, each component part illustrated in FIGS. 13-18 can be 3-D printed from metal or glass. In another embodiment each component part illustrated in FIGS. 13-18 can be made using flexible flat glass that can be quickly laser cut, stacked, and formed into unitary multi-layer, flat glass structures. These unitary structures can be functional (e.g., designed for fluids to flow through them), and/or can house entire instruments or components thereof (e.g., mobiles phones, sensors, batteries, circuit boards, etc.). Because the structures can be transparent or translucent one can take advantage of the ability to direct light (e.g., UV light) into and/or through them.

Cleaning Glass 3D-GC with UV Light

One of the common problems of operating analytical gas chromatographs in the field is permanent contamination of gas delivery system (pre-concentrator, GC column and tubing) with analytes. Out of all the GC parts, the pre-concentrator suffers from contamination most of all. Several purging cycles for pre-concentrators may be required, which dramatically increases the time of scan. Permanent contamination becomes the major issue for detection of highly electronegative molecules, such as high explosives (TNT, PETN, RDX, HMX, TATP, HMDT). High adhesion energy of such molecules can make cleaning by thermal desorption especially challenging. The problem is not limited to the explosives only and concerns a wide variety of background VOCs generally present in the environment. Currently, there is no efficient solution to permanent contamination in the field conditions leading to malfunction and waste of analytical equipment in harsh environments for almost any application.

Internal surfaces of an exemplary GC gas delivery system implemented in accordance with the present disclosure may be cleaned by UV light. The oxidation reaction to decompose the molecules of contaminants is proceeded first by cutting molecular bonding of contaminants and then adding oxygen atoms to them. In the case of organic materials, chain scission of molecules happens and organic residue contaminants are gently removed from the substrates as volatile byproduct molecules such as $CO_2$, $H_2O$ and $O_2$. A cleaning mechanism like that can only be utilized in a glass-printed GC, since the UV light can transmit through the entire gas delivery system enhancing the purging cycle by breaking and oxidizing the remaining contaminants. As a result, the GC gas delivery system made of 3D printed glass resets itself faster between the scans compared to non-glass GC.

FIGS. 21A-F show a schematic flow of an illustrative VOC analysis cycle of an exemplary MGC portable lab or hand-held device configuration. The exemplary VOC analysis cycle 2100 depicted by FIGS. 21A-F is an analysis method including multiple stages (phases) described below. An exemplary portable GC lab 130 or handheld GC 135 may implement a VOC analysis cycle in accordance with the exemplary VOC analysis cycle 2100 depicted by FIGS. 21A-F. An exemplary portable GC lab 130 or handheld GC 135 may include a processor configured to implement the VOC analysis cycle 2100. The GC lab 130 or handheld GC 135 processor may be configured to be operable with pumps, valves, sensors, heaters, a GC column, and other components. The GC lab 130 or handheld GC 135 processor may implement the VOC analysis cycle 2100 based on operating at least one valve in combination with activating at least one pump and activating at least one heater as described herein, to separate a test mixture sample in the GC column while capturing a sensor signal. Active elements depicted by FIGS. 21A-F are delineated by dashed lines.

Figure 21A:
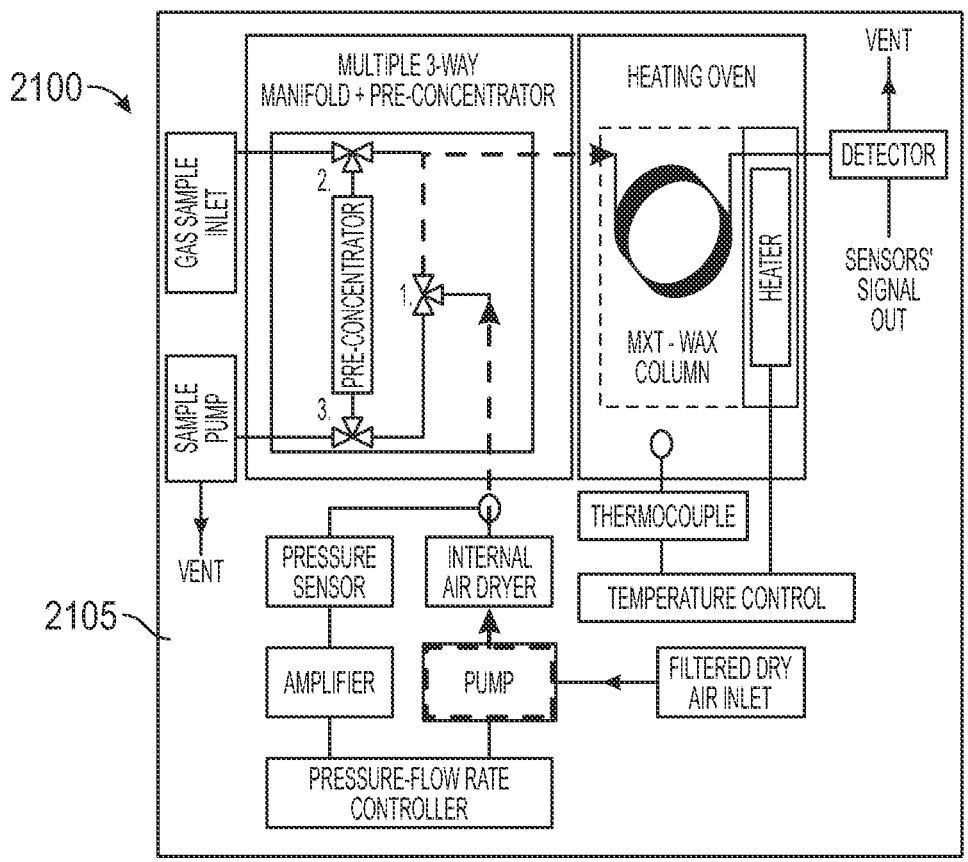
FIGS. 21A-F show a schematic flow of an illustrative VOC analysis cycle of an exemplary MGC portable lab or hand-held device configuration.

In the exemplary VOC analysis cycle 2100 phase 2105 depicted by FIG. 21A, when the power switch of the device is turned on, the main pump activates the constant stream of carrier gas (scrubbed air) flows through the column. The carrier gas first flows through a scrubber, then through valve 1 to the column and from the column to the detector module. The carrier gas is flowing through the system at all times when the device is on.

Figure 21B:
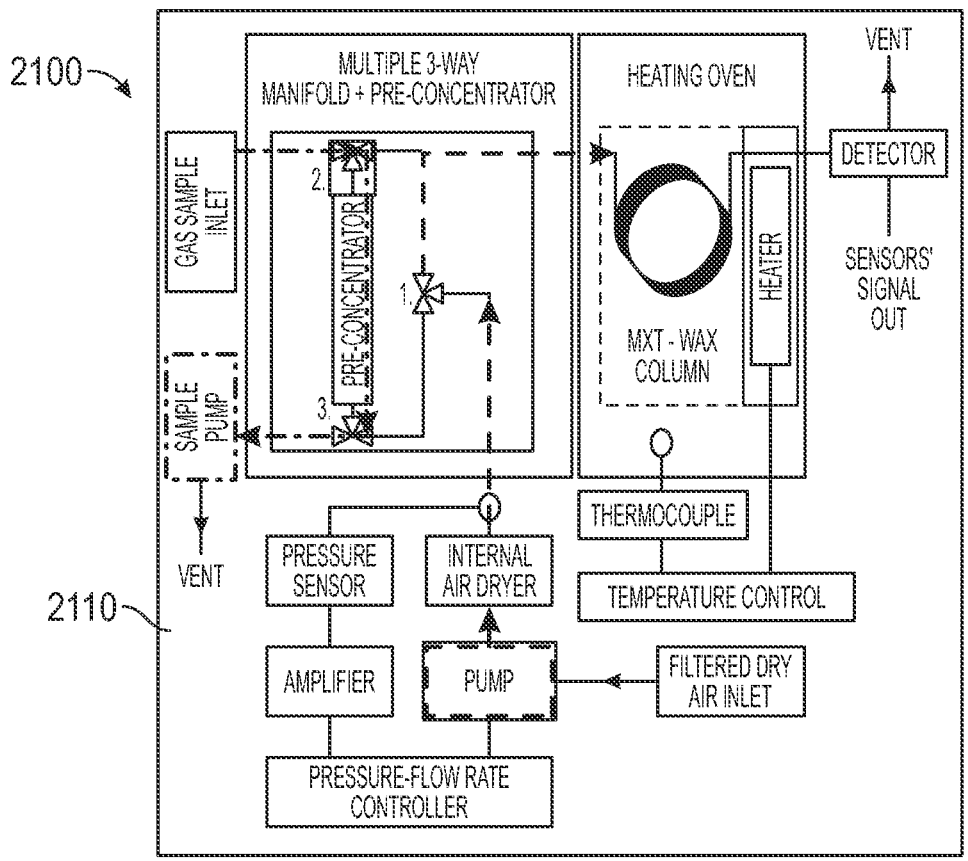

In the exemplary VOC analysis cycle 2100 phase 2110 depicted by FIG. 21B, when the sample pump is activated, the ambient air containing the analytes of interest passes through the pre-concentrator, which collects the particles of interest. In this phase of the cycle, both valves 2 and 3 are open and the pre-concentrator is at room temperature, so it efficiently absorbs the chemicals. The typical sampling time is 10 seconds. After 10 seconds the system may continue to the next step automatically.

Figure 21C:
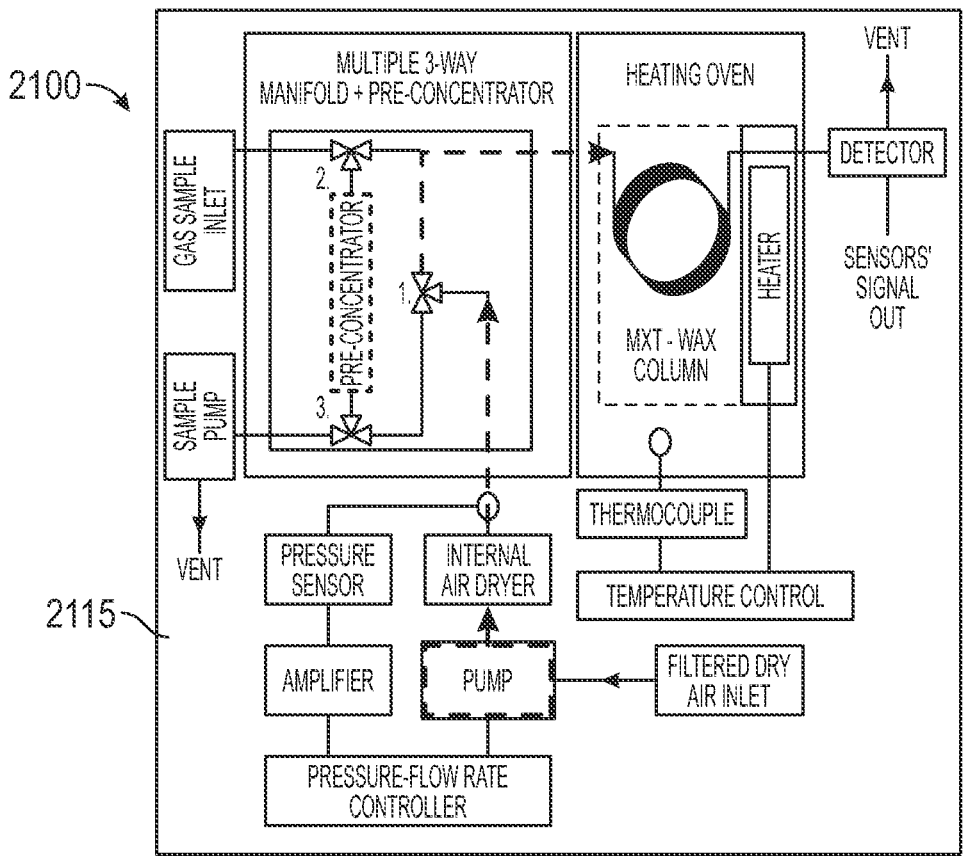

In the exemplary VOC analysis cycle 2100 phase 2115 depicted by FIG. 21C, after 10 seconds, valves 2 and 3 close and the pre-concentrator heats up to desorb the molecules. After 30 seconds the system may continue to the next step automatically.

Figure 21D:
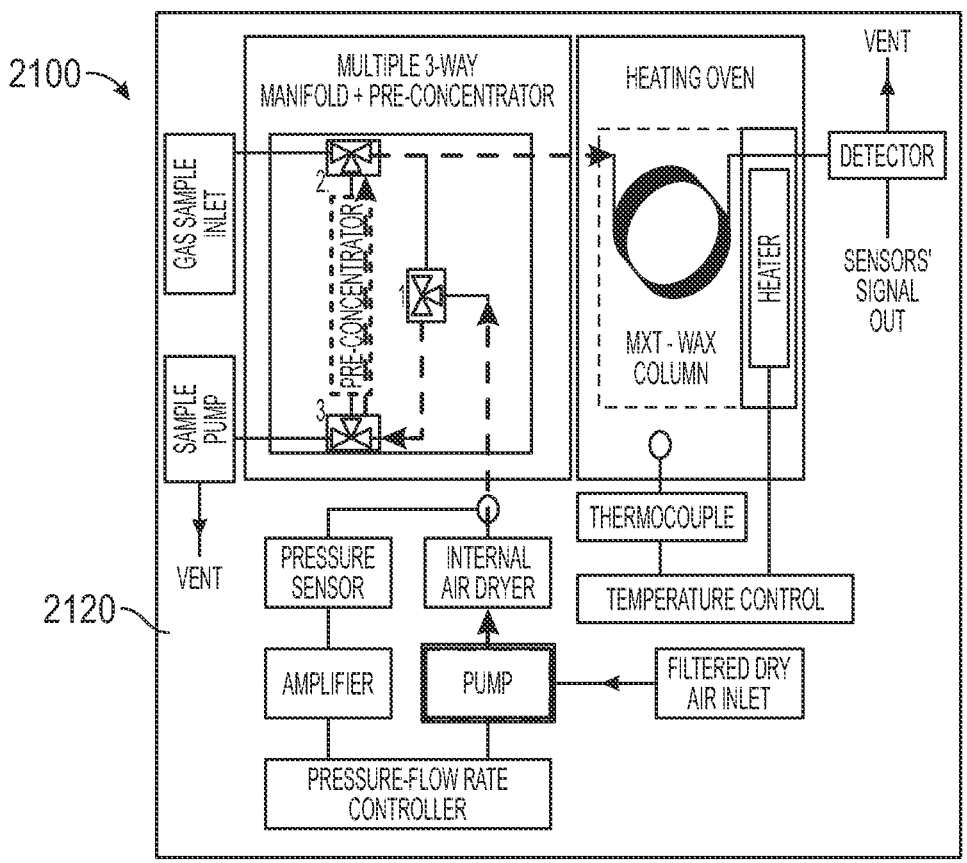

In the exemplary VOC analysis cycle 2100 phase 2120 depicted by FIG. 21D, the carrier gas is redirected by valve 1 through the pre-concentrator. Valves 2 and 3 are open and the pre-concentrator remains at high temperature during this step, so that the desorbed gas sample is injected into the column. After 30 seconds the system may continue to the next step automatically.

Figure 21E:
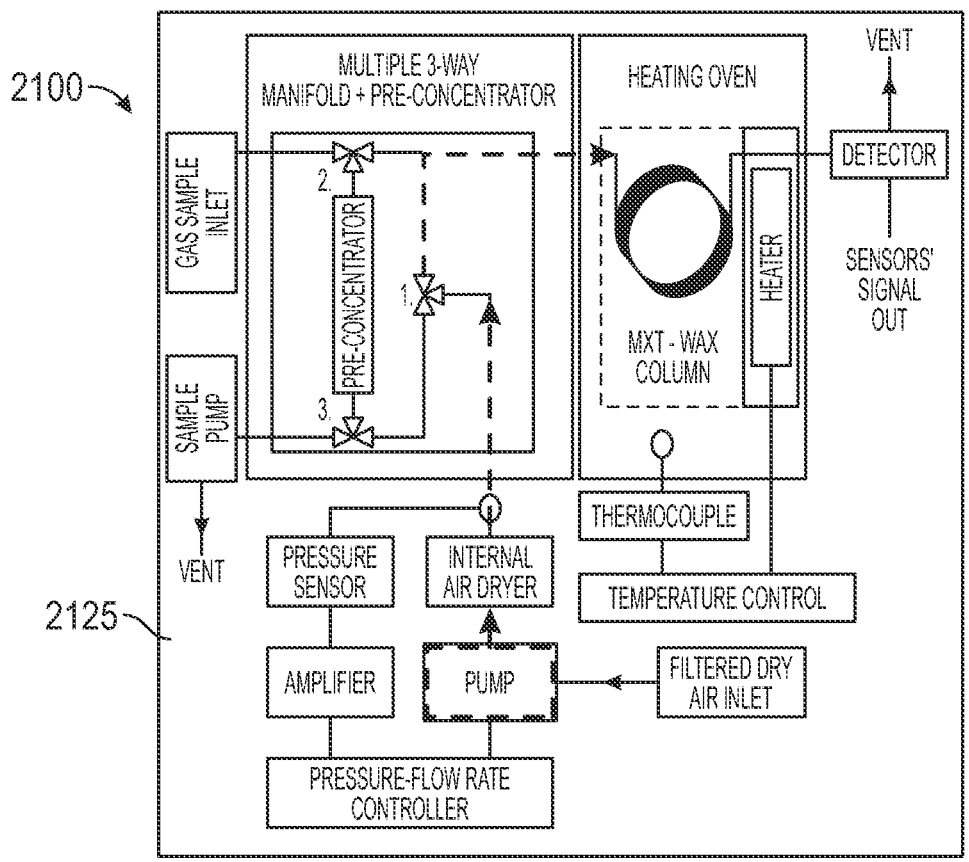

In the exemplary VOC analysis cycle 2100 phase 2125 depicted by FIG. 21E, valve 1 redirects the carrier gas directly through the column, bypassing the pre-concentrator. The analyte mixture is separated by the column. The analytes exit the column and hit the detector. The detector signal is measured and recorded. The time of this phase is determined by the retention time of the heaviest analyte in the mix. For example, in the case of BTEX, it is a retention time of Xylene, which is about 550 s. In an illustrative example, the data may be collected during 600 s, and after 600 seconds the system may continue to next step automatically.

Figure 21F:
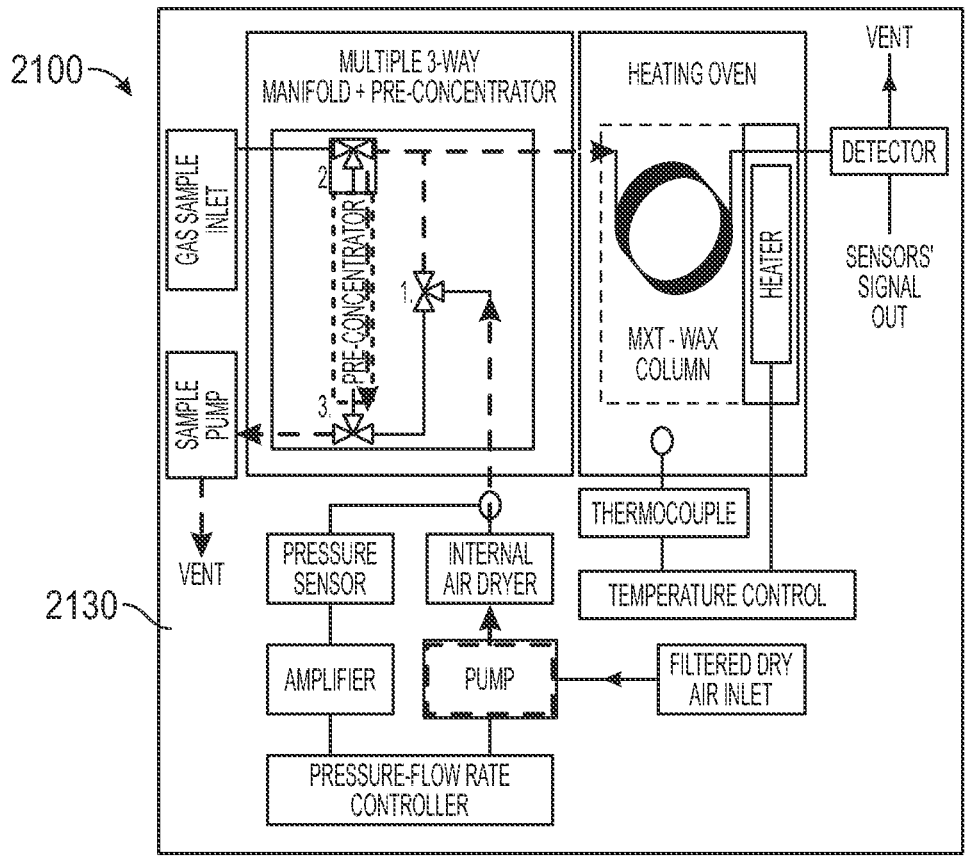

In the exemplary VOC analysis cycle 2100 phase 2130 depicted by FIG. 21F, the device is purging the pre-concentrator from the remaining particles. Valve 2 opens to branch the flow from the main pump through the pre-concentrator and out of the sample pump. In this phase the pre-concentrator remains hot to desorb the remaining particles. The sample pump is not powered, the pressure of the gas allows it to escape thorough the pump without assistance. This step concludes the exemplary GC cycle.

Figure 22A:
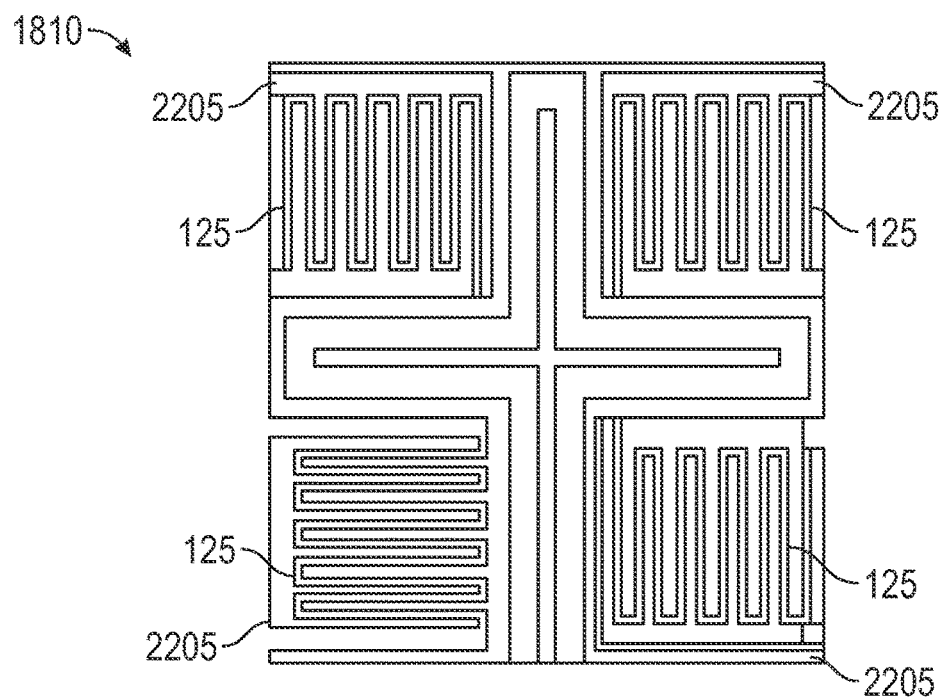
FIGS. 22A-E show various views of an exemplary MGC multi-sensor.
Figure 22B:
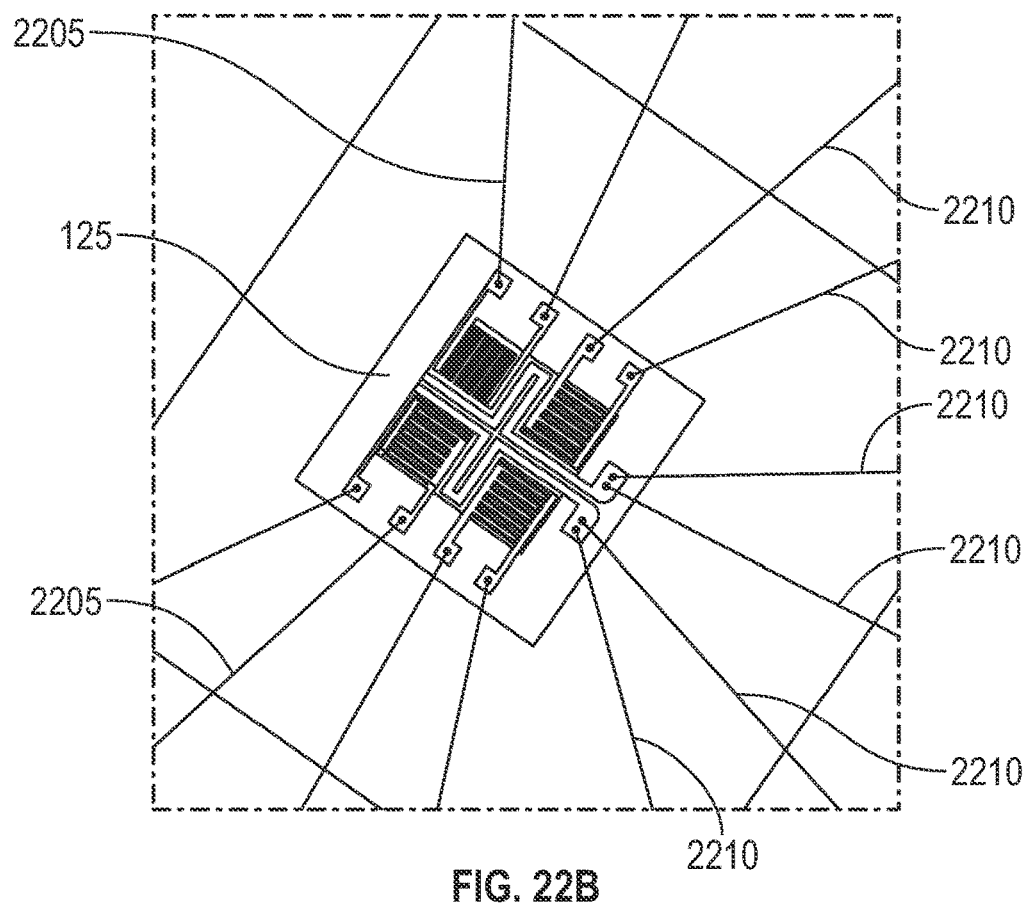
Figure 22C:
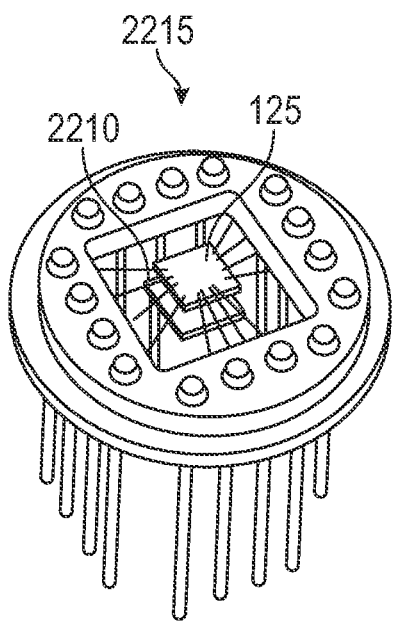
Figure 22D:
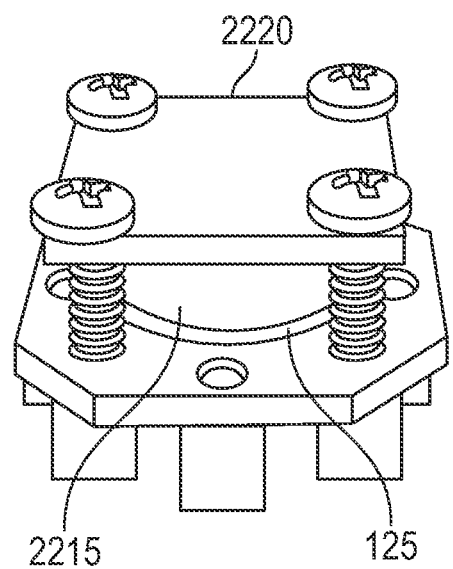
Figure 22E:
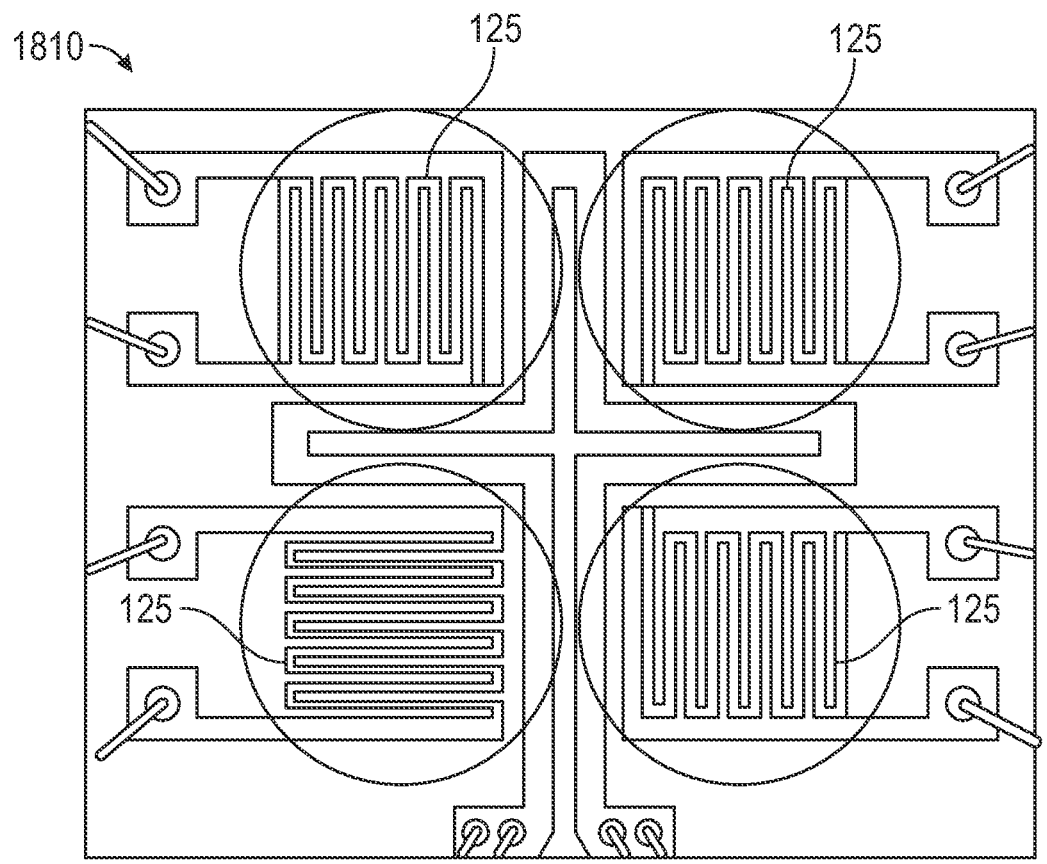

FIGS. 22A-E show various views of an exemplary MGC multi-sensor. In FIG. 22A, the integrated sensor array 1810 includes the sensor 125 elements disposed on substrates 2205 in the platform with a cross-shaped platinum heater in the middle. In FIG. 22B, the depicted sensor 125 is electrically connected by the wires 2210. In FIG. 22C, the depicted sensor 125 is mechanically and electrically attached to the electronic package 2215. In the example depicted by FIG. 22C, the electronic package 2215 is a TO-8 package. FIG. 22D depicts the exemplary GC multisensory detector 2220 with the electronic package 2215 including the sensor 125 configured to operate in a flow-chamber. FIG. 22E depicts an exemplary integrated sensor array 1810 implementation with the sensor array 1810 suspended at the corners by thin metal legs to achieve temperature insulation of the sensor array 1810. The integrated sensor array 1810 or the sensor element 125 depicted at least by FIGS. 22A and 22E may also be the sensor 8100, configured with a structure based on 3-D printing glass/metal technology, or punctuated layered glass technology, as depicted at least by FIGS. 2, 3, 9, 10, 11A, 11B, 12A, and 12B.

In one embodiment, the detector consists of an integrated multi-sensory platform, with an array of four sensory elements and a modified transistor outline (TO) package. The integrated multi-sensory platform (2.5×2.5×0.3 mm) was designed to control operation of 4 sensory elements at high temperatures, between 150 and 600° C., providing synchronized multi-sensor analysis of gas samples. The temperature insulation of the multi-sensory platform from the TO package is accomplished by suspending the platform on thin metal legs at the corners of the platform.

Table 1 summarizes four different types of sensors developed for comprehensive analysis of target analytes. The sensor S1 was left unmodified. The surface of sensor S2 was functionalized with 10 nm+/−0.2 nm of copper oxide (CuO 99.99%) deposited over the $SnO_2$ layer at 150 W RF power. The surface of sensor S3 was modified with a thin bimetal Au(90%)/Pd(10%) alloy layer by simultaneous sputtering from both Au and Pd targets. The sensor S4 is a continuous ultra-thin platinum resistance pattern used as a thermal conductivity detector.

TABLE 1

| Sensor structure and composition as deposited. | | |
|---|---|---|
| Sensor # | Sensor's bulk material | Sensor's surface modification |
| S1 | $SnO_2$ (30 nm ± 2 nm) | |
| S2 | $SnO_2$ (30 nm ± 2 nm) | CuO (20 nm ± 2 nm) |
| S3 | $SnO_2$ (30 nm ± 2 nm) | Au/Pd (1.1 nm ± 0.2 nm) |
| S4 | Pt | |

A key advantage of implementations in accordance with the present disclosure is the utilization of novel solid-state detectors for portable real-time gas chromatography (FIGS. 22A-E). Our novel nanocomposite solid state MEMS detector (integrated sensor array) demonstrated outstanding performance for detection of ultra-low concentrations of gases and vapors down to sub-ppb level. Multiple electronically independent sensing elements significantly improve signal-to-noise ratio of the detector due to independence of their outputs without chemical exposure and their synchronized response under exposure. The detector consists of an integrated multi-sensory platform, with an array of four sensory elements and a modified transistor outline (TO) package. The integrated multi-sensory platform (2.5×2.5×0.3 mm) was designed to control operation of 4 sensory elements at high temperatures, providing synchronized multi-sensor analysis of gas samples. The proposed design provides high detector stability over a long period of time at elevated temperatures in the range between 150 and 600° C. The multi-sensory platform consists of three pairs of platinum electrodes for three semiconductor sensing elements, a continuous ultra-thin platinum resistance pattern used as a thermal conductivity detector and a platinum cross-shaped heater located on the suspended membrane (1.5×1.5×0.05 mm) at the center of the platform (FIG. 22A).

The contacts and the heater were fabricated on the $Si/SiO_2$ (300/0.5 µm) substrate simultaneously, by using photolithographic (Suss Mask Aligner MA6/MA8) and magnetron sputtering technique (KJL PVD 75 Sputtering System) followed by a liftoff process. The total thickness of 300 nm+/−10 nm of Pt contacts and the heater was verified by using a surface profilometer KLA-Tencor Alpha-Step IQ.

The membrane structure was fabricated by using reactive ion etching (RIE) and deep reactive ion etching (DRIE) techniques by utilizing MARCH RIE CS-1701 and Oxford PlasmaLab System 100 ICP 300 Deep RIE instruments, respectively. The membrane is connected to the main platform's base via small $Si/SiO_2$ connectors. The temperature insulation of the multi-sensory platform from the TO package was accomplished by suspending the platform on thin metal legs at the corners of the platform. The electrical connection between the multi-sensory platform and the TO package was formed by using a wire-bonding technique (FIG. 22B).

Four different types of sensors (Table 1) were developed for comprehensive analysis of target analytes. All the depositions were conducted under 5 mTorr of argon pressure. A thin layer of $SnO_2$(30 nm+/−2 nm) was first deposited over three out of four sensors S1-S3. During the $SnO_2$ sputtering, the deposition rate was kept constant at 0.6 A/s by applying 200 W RF power to a 4-inch tin oxide ($SnO_2$ 99.99%) target under 12 mTorr of Argon pressure. The sensor S1 was left unmodified. The surface of sensor S2 was functionalized with 10 nm+/−0.2 nm of copper oxide (CuO 99.99%) deposited over the $SnO_2$ layer at 150 W RF power. The surface of sensor S3 was modified with a thin bimetal Au(90%)/Pd(10%) alloy layer by simultaneous sputtering from both Au and Pd targets. The DC power for the Pd target was 15 W to keep the deposition rate of Pd 0.1 A/s and the power for the gold target was 50 W, keeping the deposition rate 1 A/s. A 10 s deposition produced a layer of Au/Pd alloy 1.1 nm thick. The thicknesses of all the layers were monitored during the deposition process by using quartz crystal sensor (Inficon, Gold, 6 Mhz) and verified by surface profile-meter (Alpha Step 500). The sensor S4 is a continuous ultra-thin platinum resistance pattern used as a thermal conductivity detector.

The choice of detector materials was guided by experiments. In an implementation, the detector may be configured with an ultra-sensitive TCD detector for target analytes at concentrations of 10 ppm or higher.

Thermal conductivity detector (TCD). Ultra-sensitive TCD detector is ideal for monitoring VOCs at relatively high concentrations. Thanks to the extremely high surface-to-volume ratio and efficient thermal isolation of the resistance pattern, the limit of detection (LOD) for most of the compounds was found to be 10 ppm, which is substantially lower than that of the conventional TCD detectors with the suspended platinum wire.

Dual oxide $SnO_2$/CuO sensor. Most of the metal oxide sensors require the presence of atmospheric oxygen to maintain high catalytic activity. An exception from this rule is a dual oxide $SnO_2$/CuO sensor. Its unique selectivity to hydrogen sulfide and mercaptans is based on a reversible metal-semiconductor transition upon exposure to $H_2S$:

$$H_2S(g) + CuO(s) \rightarrow CuS(s) + H_2O(g) \qquad \text{Formula 1}$$

CuS is a highly conductive low band-gap semiconductor. The gas-sensitive material becomes highly conductive upon exposure to hydrogen sulfide and returns to its original state when the vapor pressure of $H_2S$ drops. These types of sensors perform with high efficiency in the air or in the inert carrier gas. Among other advantages of utilization of multilayer oxides in chemiresistors are low activation temperature, short activation time, short time of response time and short time of recovery.

Au/Pd bimetal nanoparticle sensor Metal Oxide Sensor. Semiconductor sensor functionalized with bimetal Au/Pd nanoparticles is excellent for detection and quantification of combustibles. Its detection principle is based on rapid catalytic reaction with ionized surface oxygen. Bimetal nanoparticles activate and ionize atmospheric oxygen promoting catalytic reactions with reducers, especially with combustibles.

Unmodified $SnO_2$ sensor. One of the sensors on the platform is a broadly tuned nonspecific metal oxide sensor.

Figure 23:
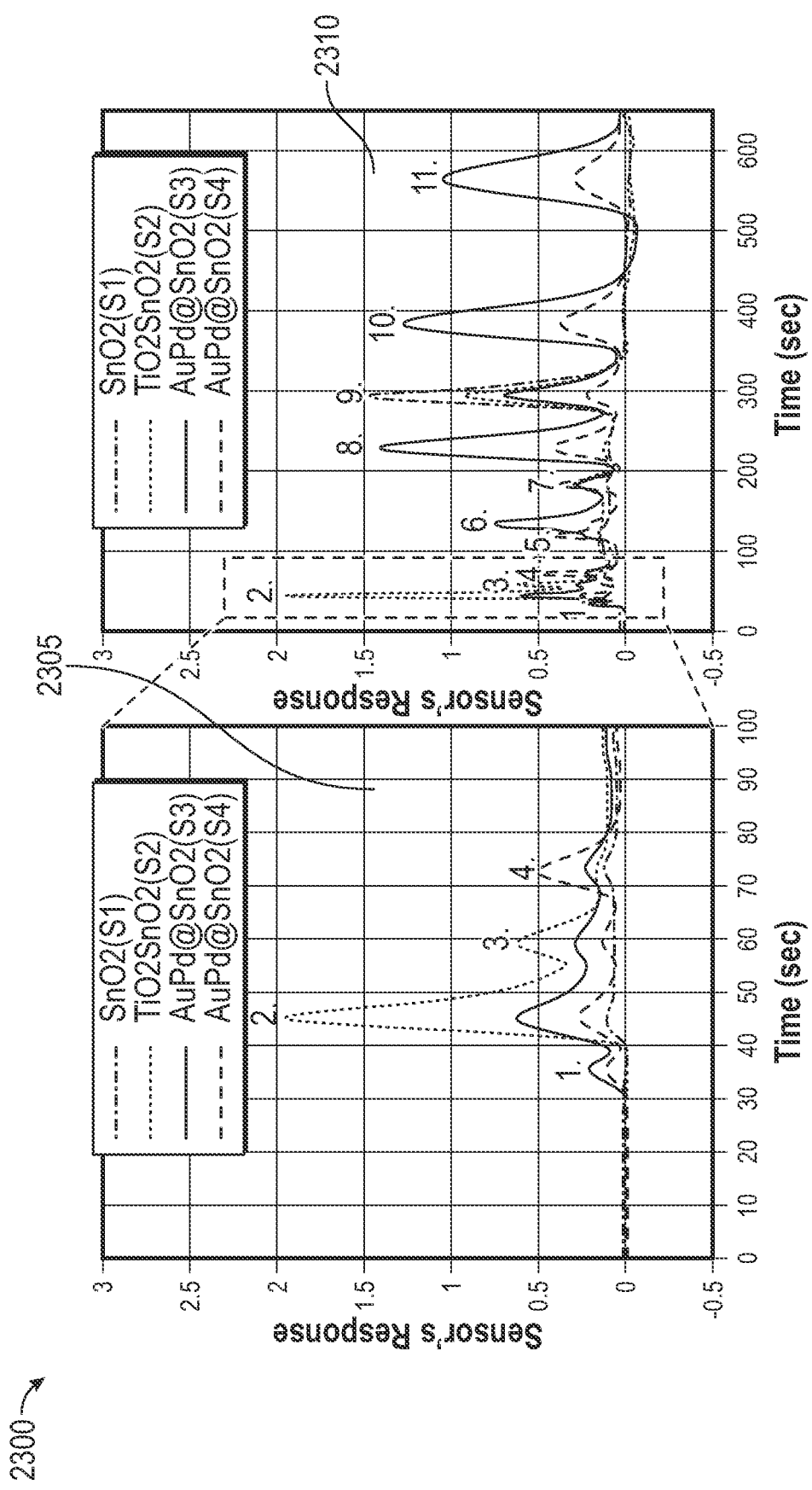
FIG. 23 shows exemplary output of an exemplary MGC integrated detector including an illustrative zoomed image of light compounds and the full gas chromatogram.

For analysis of VOCs in the field conditions, a low weight and small size of the instrument together with the short time of scan are essential. At the same time, real-life samples of VOCs are complex blends of sometimes unpredictable nature, which requires the field analysis to be as comprehensive as the laboratory analysis. A detailed chemical analysis of a complex blend using a single compact GC column requires more advanced analytical technique, than conventional separation via retention time only. The disclosed Multisensory Gas Chromatography (MGC) approach is a hybrid approach combining gas chromatography and electronic nose principles. By having an integrated sensor platform as a detector, the chemicals within a single peak can also be separated by catalytic reactivity, adding an extra dimension to conventional analytical GC. Our MGC approach disclosed herein can be demonstrated on a gaseous blend of nine common environmental pollutants. The following mixture was used for demonstration: carbon monoxide (10 ppm), hydrogen sulfide (100 ppb), ethyl-mercaptan (50 ppb), acetone (50 ppb), ethanol (50 ppb), benzene (10 ppb), toluene (10 ppb), ethylbenzene (10 ppb), and o-xylene (10 ppb). The mixture was introduced into the MGC and the output of 4 sensors from the integrated array is shown in FIG. 23. The individual sensor's response is defined in the equation below as the ratio of the sensor's resistance in carrier gas to its resistance in the presence of analytes:

$$\text{Sensor's response} = \frac{R_{carrier\ gas}}{R_{analyte}} \qquad \text{Formula 2}$$

The exemplary MGC analyzing the gaseous blend test mix was configured with an exemplary detector implemented in accordance with the present disclosure. The detector output is shown in FIG. 23. As it can be seen from FIG. 23, the chemicals from 1 to 3 and 5 & 6 would be inseparable by a conventional detector and would come out as single peaks on the chromatogram if measured by a conventional detector, due at least to the conventional detector not being able to measure the chemical's partial concentrations. In stark contrast with a conventional detector, due to the quick response and recovery of the multisensory detector implemented in accordance with the present disclosure, these chemicals are separated in time as individual peaks illustrated by FIG. 23. Also, because of the quasi-orthogonality of sensors in the array implemented in accordance with the present disclosure, the integrated electronic signature (combination of signals from 4 sensors) is unique for each of the analytes. By combining time separation, using a chromatography column with chemical separation (by catalytic reactivity), and using a quasi-orthogonal array of sensors, a substantially more comprehensive analysis of a gas mixtures, can be then obtained. That is, by utilizing 4 very different sensory elements in one detector, 4 chromatograms are obtained in a single analysis cycle, adding another dimension to the separation and recognition of chemicals.

FIG. 23 shows exemplary output of an exemplary MGC integrated detector including an illustrative zoomed image of light compounds and the full gas chromatogram. In FIG. 23, the exemplary MGC integrated detector output 2300 includes the zoomed image 2305 of light compounds and the full gas chromatogram 2310. The depicted output 2300 data are: 1. CO 10 ppm, 2. H2S 100 ppb, 3. Ethyl-Mercaptan 50 ppb, 4. Acetone 50 ppb, 5. Ethanol 50 ppb, 6. Benzene 10 ppb, 7. Unknown, 8. Toluene 10 ppb, 9. Water, 10. Ethylbenzene 10 ppb, 11. O-Xylene 10 ppb.

Figure 24:
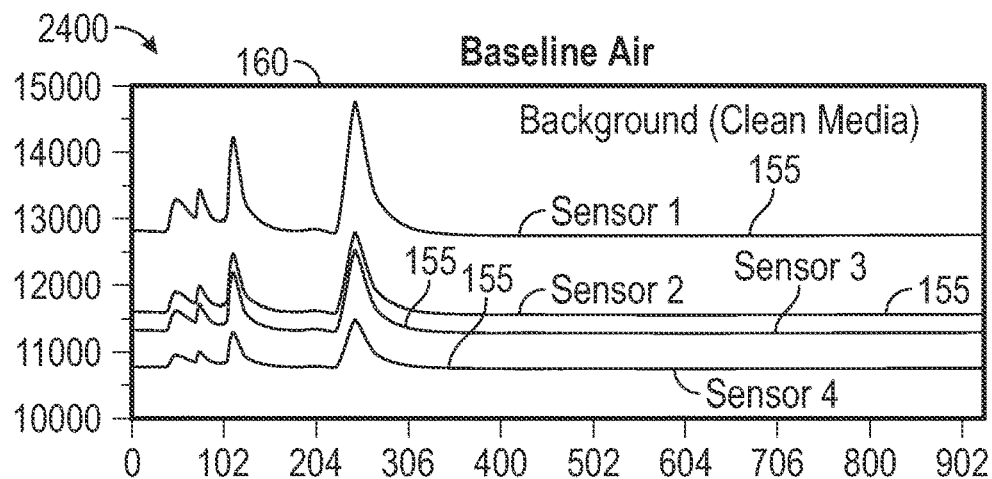
FIG. 24 shows examples of chromatograms obtained from cultured bacteria by an exemplary MGC.
Figure 24:
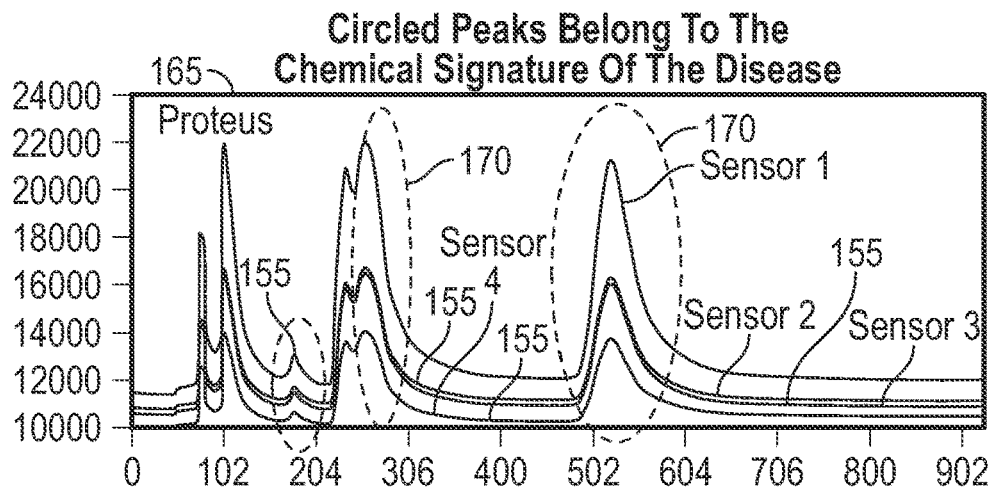
Figure 24:
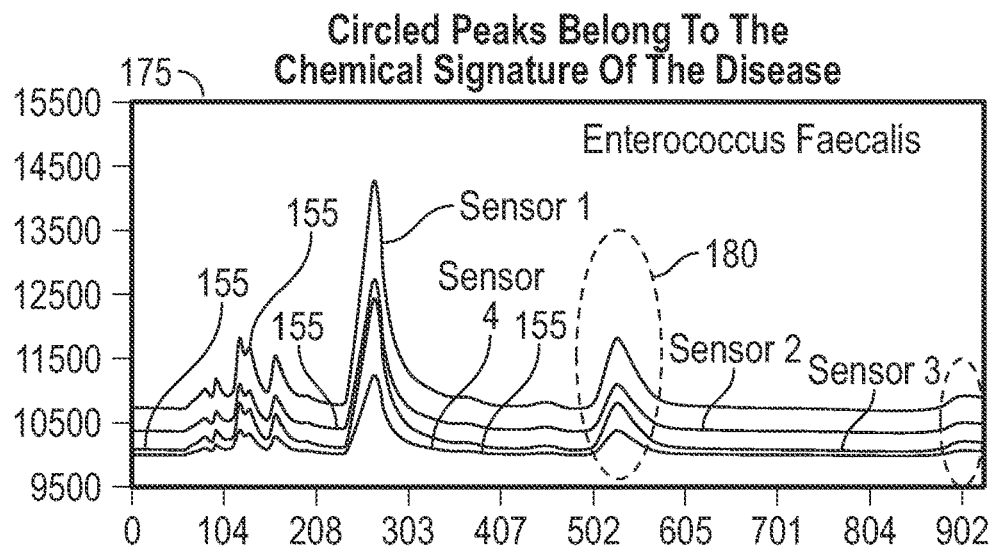

FIG. 24 shows examples of chromatograms obtained from cultured bacteria by an exemplary MGC. In FIG. 24, the exemplary MGC identifies a pathogen of interest based on an electronic chemical signature determined as a function of combined chromatogram data peaks separated based on sensor measurement response characteristic differences resulting from catalytic reactivity diversity among a plurality of sensors. The depicted example combined chromatograms 2400 were constructed by an exemplary MGC from cultured bacteria. In the depicted example, the MGC processor creates a distinct individual chromatogram 155 for each of the signals received by the processor from multiple sensors. In the illustrated example, the processor constructs a chromatogram combining time separation with catalytic separation from the multiple individual chromatograms 155 generated by the processor from the multiple sensor signals. In the depicted example, the chromatogram combining time separation with catalytic separation is generated by the processor based on catalytic reactivity diversity among the multiple sensors. The catalytic reactivity diversity among the sensors results in different sensor measurement response characteristics among the sensors, illustrated in FIG. 24 by the different sensor data signal shapes of the diverse sensors measuring the same physical quantity. In the depicted example, the processor generates a test mixture electronic signature determined as a function of the combined chromatogram. In the illustrated example, the combined chromatogram 160 includes the multiple individual chromatograms 155. In the depicted example, the processor constructs the combined chromatogram 160 based on sensor measurement of clean air as a baseline. In the illustrated example, the combined chromatogram 165 was constructed by the processor based on sensor measurement of emissions from a pathogen of interest in a test sample collected by the exemplary MGC. In the illustrated example, the MGC processor identifies the pathogen of interest based on associating the test mixture electronic signature with a predetermined reference mixture signature. The predetermined reference mixture signature may be a signature of a known pathogen. In the depicted example, the circled peaks 170 belong to the signature of the pathogen identified by the MGC. In the illustrated example, the combined chromatogram 175 is constructed by the processor based on sensor measurement of a pathogen of interest in a test sample received by an exemplary handheld MGC. In the illustrated example, the handheld MGC processor identifies the pathogen of interest based on associating the test mixture electronic signature with a predetermined reference mixture signature. The predetermined reference mixture signature may be a signature of a known pathogen. In the depicted example, the circled peaks 180 belong to the signature of the pathogen identified by the handheld MGC.

Figure 25:
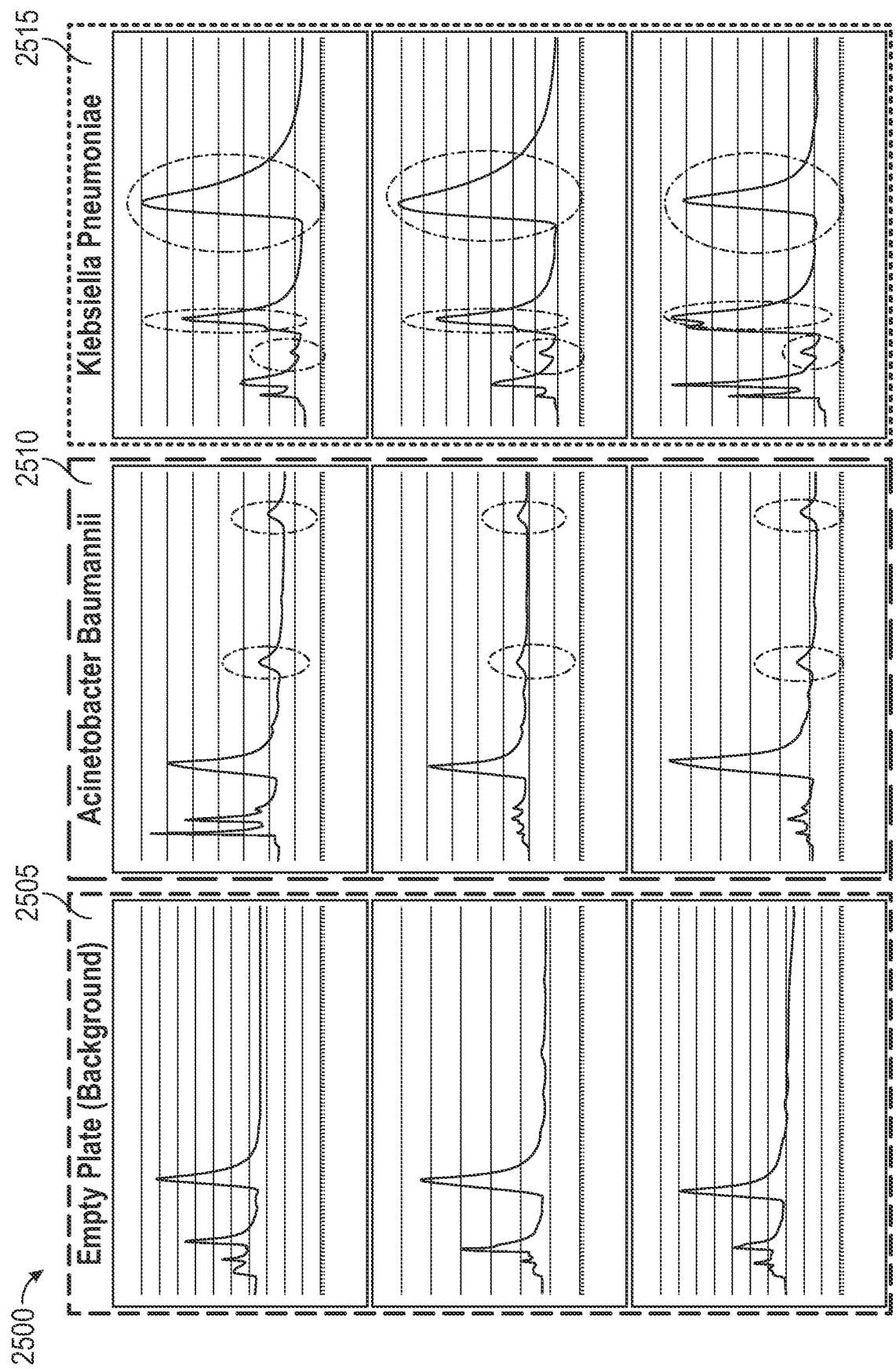
FIG. 25 shows example chromatograms of the same pathogens obtained from different patients by an exemplary MGC.

FIG. 25 shows example chromatograms of the same pathogens obtained from different patients by an exemplary MGC. In FIG. 25, the exemplary chromatograms 2500 include chromatograms of the same pathogens (2505 Empty Plate (Background), 2510 *Acinetobacter Baumannii*, and 2515 *Klebsiella Pneumoniae*) obtained from different patients. The circled peaks belong to the electronic signature of the particular pathogen. Only one sensor output (out of 4) is shown for clarity.

Figure 26A:
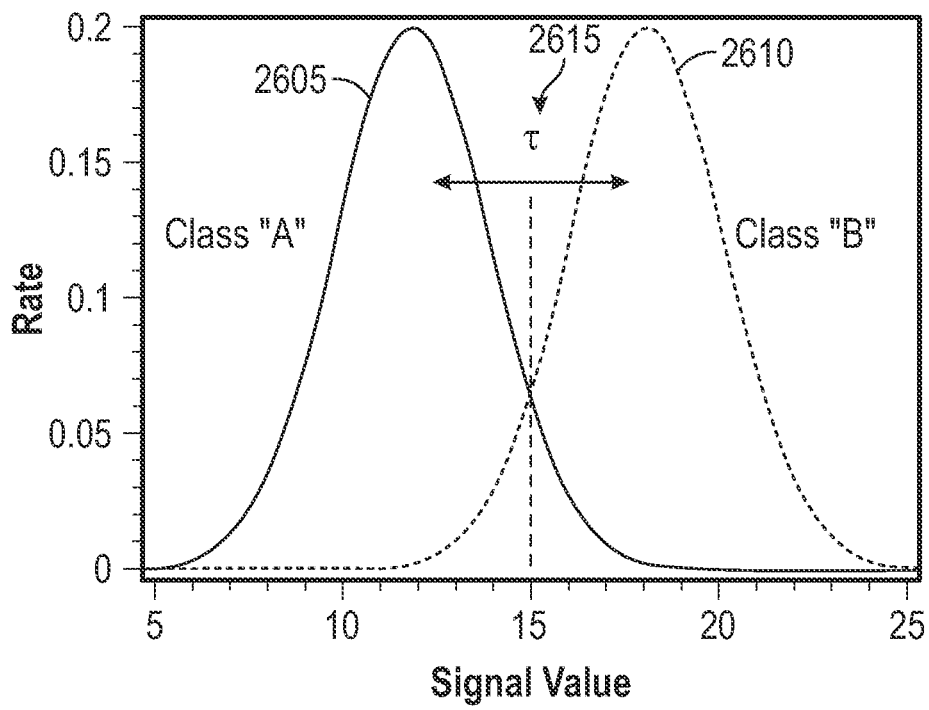
FIGS. 26A-B show an illustrative classification example.
Figure 26B:
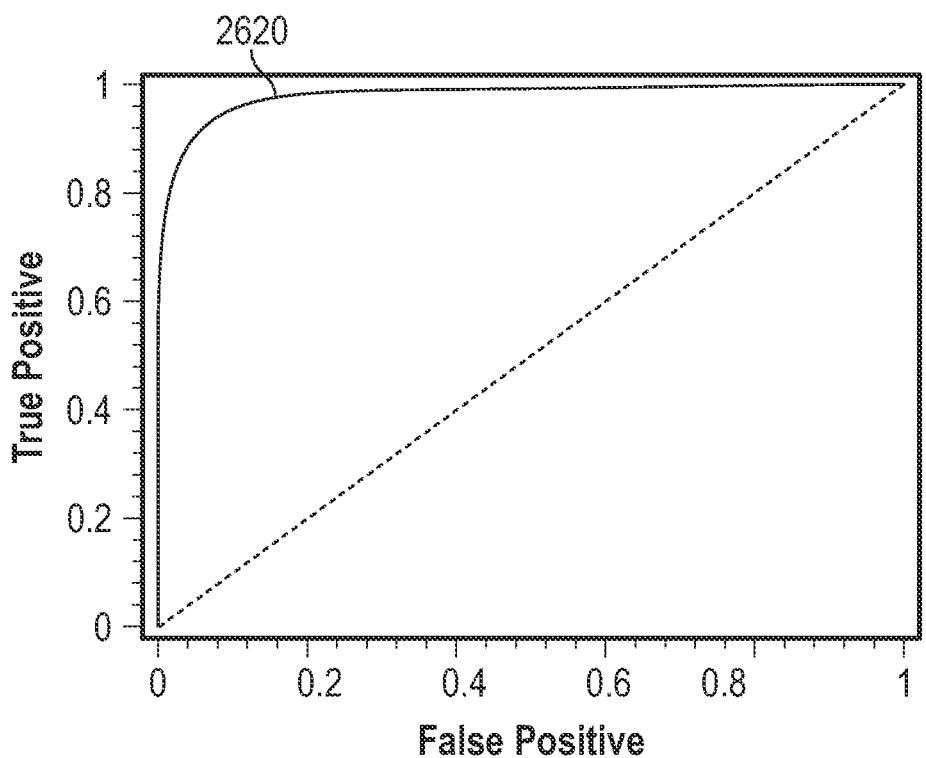

FIGS. 26A-B show an illustrative classification example. FIG. 26A depicts exemplary MGC pathogen identification based on classification. The example classification illustrates distribution a single parameter for Class A 2605 and Class B 2610 based on the threshold parameter $\tau_{threshold}$ 2615. In FIG. 26B, the performance of the algorithm may be characterized by the ROC curve 2620, obtained by varying the threshold parameter $\tau_{threshold}$ 2615 and counting true positive and false positive identifications. Each threshold parameter $\tau_{threshold}$ 2615 value corresponds to a point on the ROC curve 2620. The optimal threshold parameter 2615 $\tau_{threshold}$ value is defined as the closest to the (0, 1) point on the ROC curve 2620. The dashed diagonal in FIG. 26B represents an exemplary 50/50 classifier.

Figure 27A:
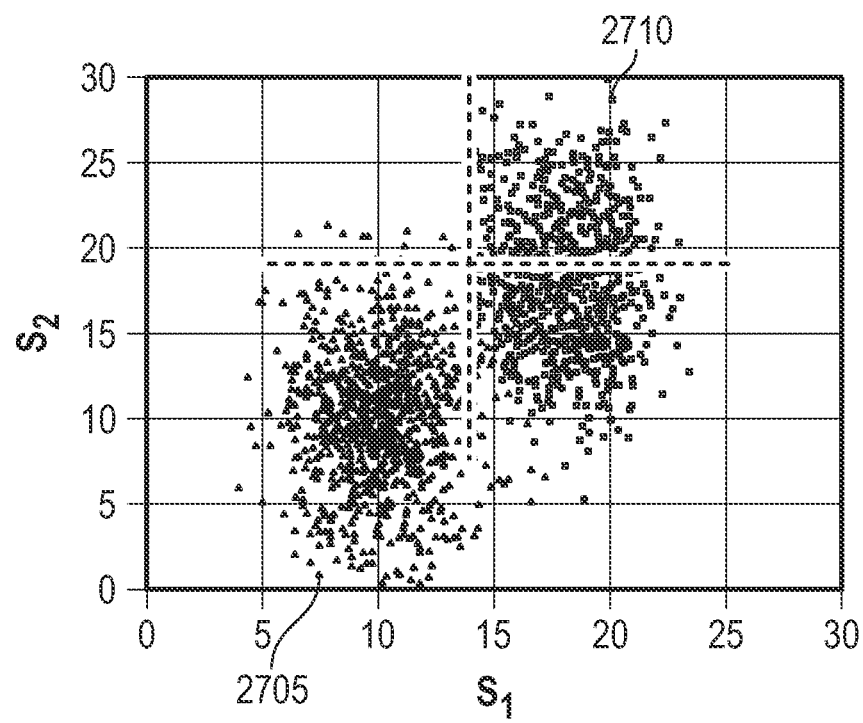
FIGS. 27A-B show illustrative VOC sample classification by an exemplary MGC in two-parameter hyperspace.
Figure 27B:
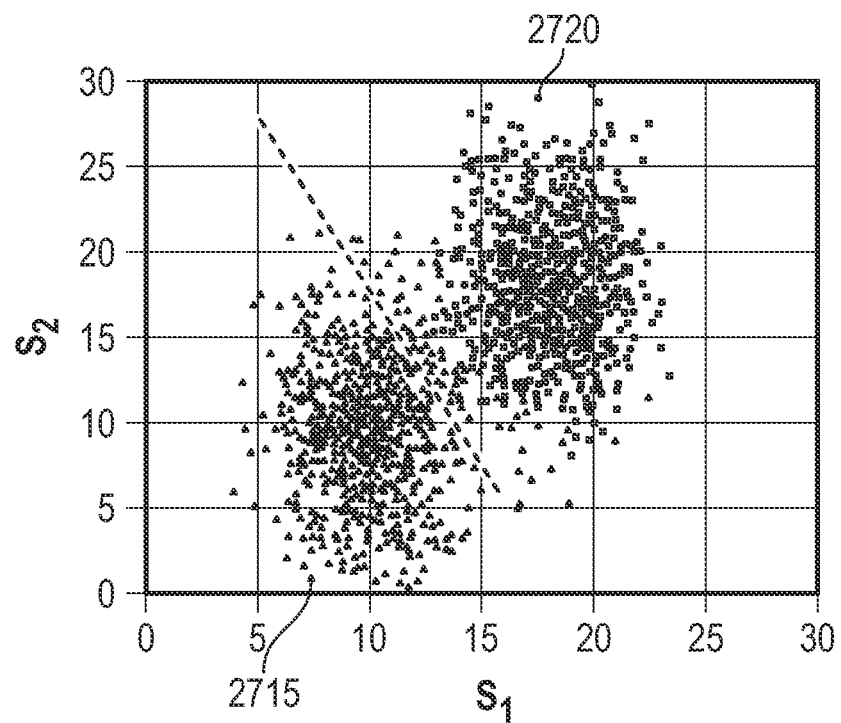

FIGS. 27A-B show illustrative VOC sample classification by an exemplary MGC in two-parameter hyperspace. In FIG. 27A, VOC class 1 2705 and VOC class 2 2710 are illustrated in two-parameters hyperspace. In the illustrated example, an exemplary threshold approach for classification is depicted by the intersecting dashed lines. In FIG. 27B, VOC class 1 2705 and VOC class 2 2710 are respectively depicted as VOC class 1 2715 and VOC class 2 2720 separated by the dashed linear boundary. In general the boundary between classes can be a non-linear function.

Various implementations in accordance with the present disclosure may be configured with processor executable program instructions implementing automatic pattern recognition and decision-making algorithms providing diagnosis instantly in a field environment. In various processor-implemented configurations, the chromatograms combining retention time separation data and catalytic separation data are input data to one or more pattern recognition algorithm. Some implementations may determine the best pathogen recognition strategy based on decision-making algorithm performance evaluated as a function of the algorithm's ability to perform differentiation between patterns, characterized by the Receiver-Operating-Characteristic (ROC) curve. In an illustrative example, input data to the decision-making algorithm may be the digitized voltage signal patterns produced by all integrated detector sensor elements upon the exposure to VOCs. Thus, every exposure will be represented as a point in a multi-parameter hyperspace. Due to the complex nature of analytes in real field testing, in various processor-implemented configurations each pathogen may be represented not with one point in the hyperspace, but rather "a cloud" of points when data from many different VOC exposure patterns will be available. These cloud patterns can overlap or be separable. Therefore, the decision-making algorithm is configured to separate these rather complicated patterns with minimal misidentification rate, using techniques that would be known to one of ordinary skill.

Figure 28A:
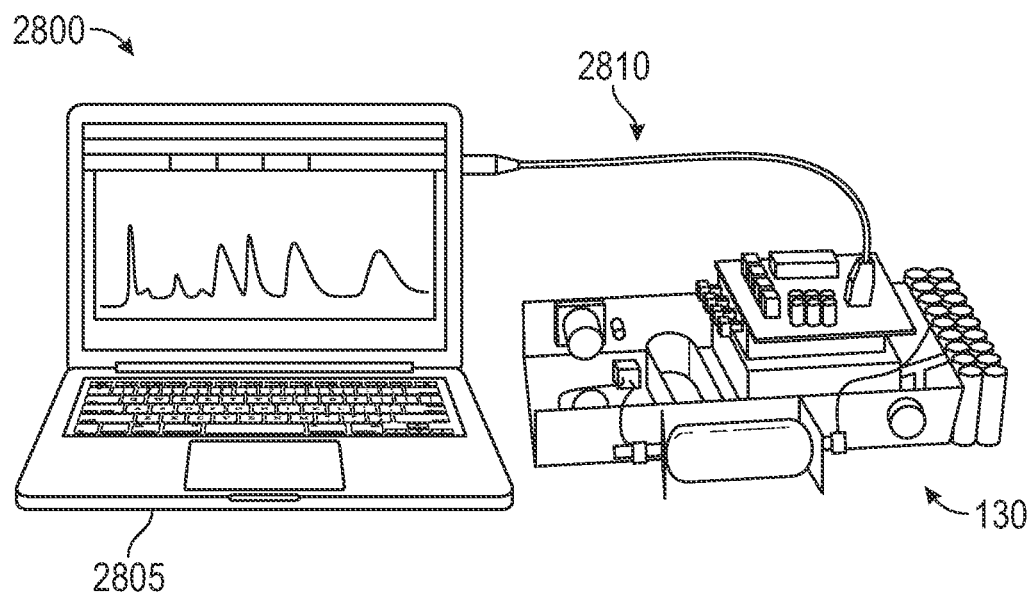
FIGS. 28A-B show exemplary MGC portable lab configurations.
Figure 28B:
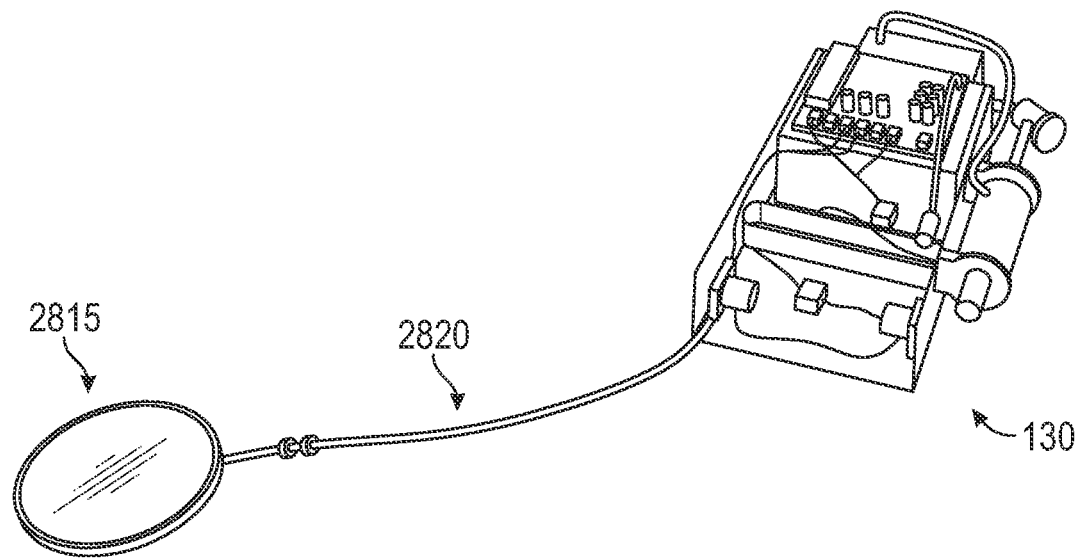

FIGS. 28A-B show exemplary MGC portable lab configurations. In FIG. 28A, the exemplary lab 2800 includes the portable computer 2805 communicatively coupled by the interface cable 2810 with the exemplary portable GC lab 130. The portable GC lab 130 is also depicted at least by FIG. 1. In FIG. 28B, the exemplary portable GC lab 130 is fluidly coupled with the collection device 2815 by the tubing 2820. In the example depicted by FIG. 28B, the portable GC lab 130 may collect a sample emitted by a pathogen in the collection device 2815.

Figure 29:
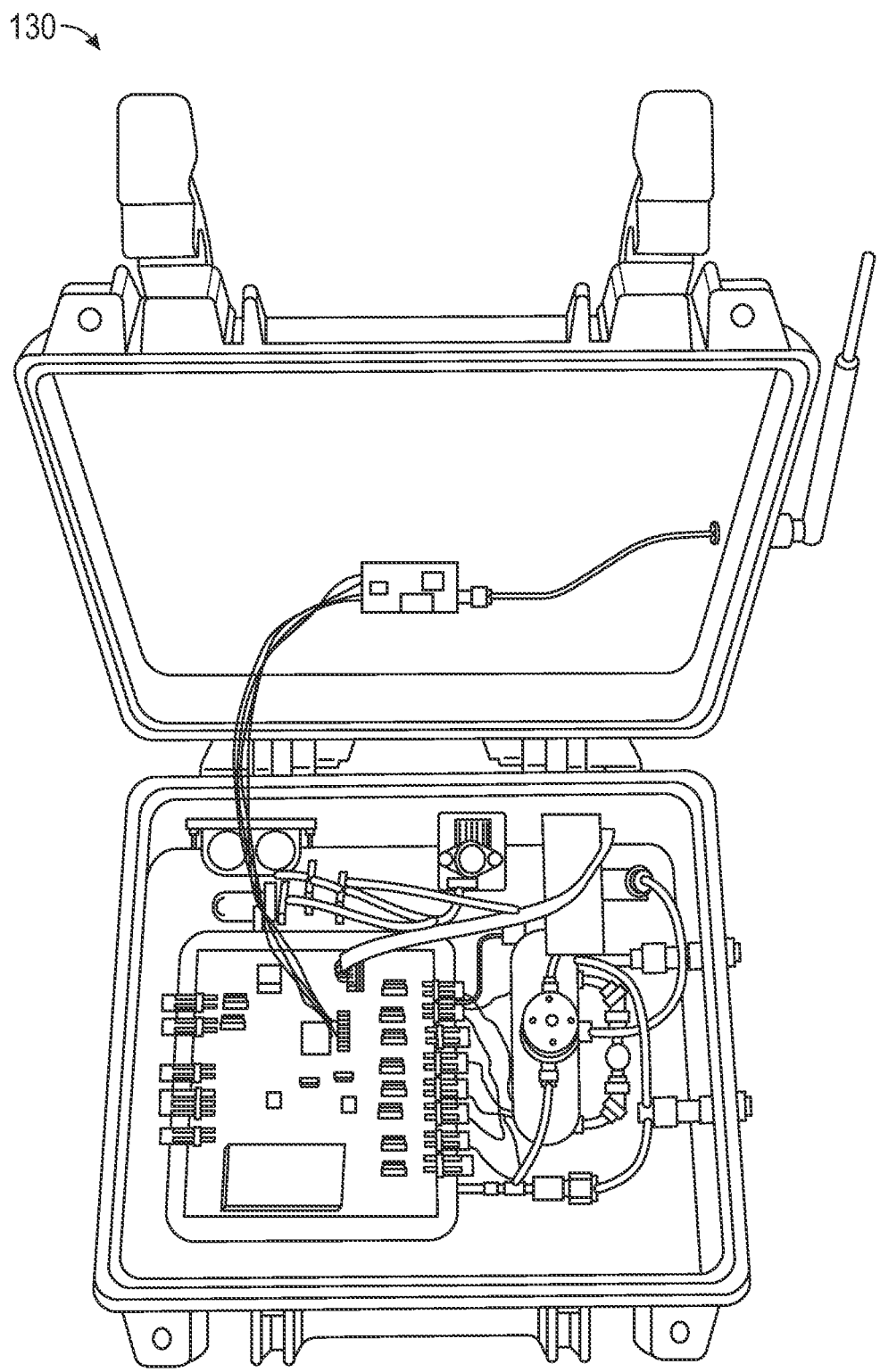
FIG. 29 shows a perspective view of an ultra-compact GC unit with a wireless data transmission system.

FIG. 29 shows a perspective view of an ultra-compact GC unit with a wireless data transmission system. The depicted exemplary ultra-compact GC unit includes the exemplary portable GC lab 130. The portable GC lab 130 is also depicted at least by FIG. 1. In the portable GC lab 130 depicted by FIG. 29, all port connections are made with standard ⅛" OD tubing, preferably TEFLON™. Swagelok® bulkhead fittings are supplied for making all port connections. The portable GC lab 130 has an internal sample pump, which will automatically pull the sample through the pre-concentrator when an analysis is initiated. This sample is collected and desorbed from the injection assembly into the column for chemical separation.

The sample injection uses a pump to load a pre-set amount of sample onto a pre-concentrator, which contains an adsorbent media for gas collection. This media is selected specifically for the application of interest and designed to collect the gas of interest and minimize the non-target chemicals. The pre-concentrator is thermally desorbed and transferred to the column assembly for chromatographic separation and elution into the detector.

Figure 30:
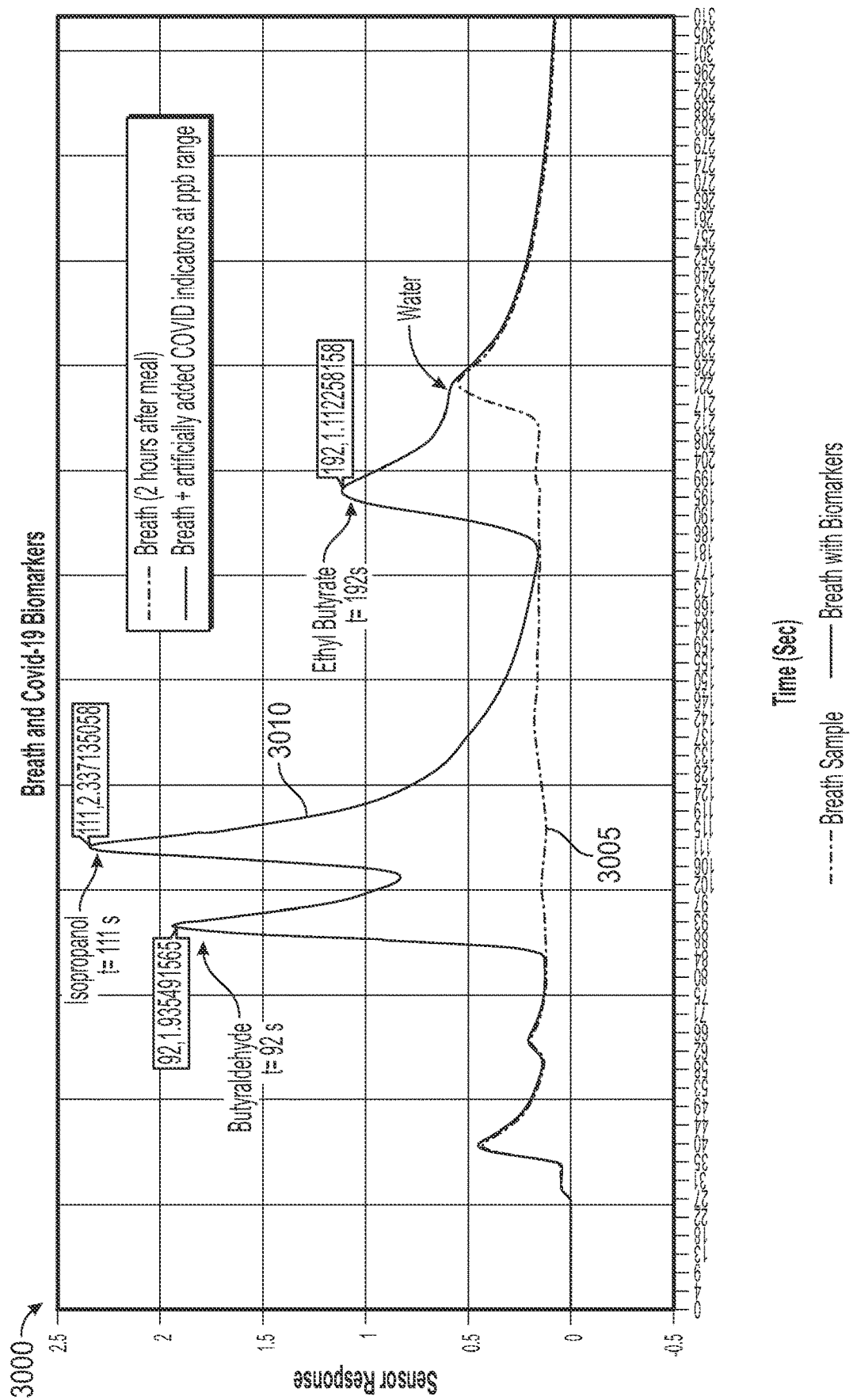
FIG. 30 shows an illustrative example of COVID-19 biomarker identification by an exemplary MGC.

FIG. 30 shows an illustrative example of COVID-19 biomarker identification by an exemplary MGC. FIG. 30 illustrates the exemplary detection 3000 of COVID-19 target VOCs by an exemplary handheld GC 135 in an exemplary breathalyzer configuration. In FIG. 30, the dashed graph 3005 shows a breath sample two hours after meal. The solid graph 3010 shows the same breath sample with artificially added COVID 19 biomarkers at ppb levels of concentrations.

Figure 31:
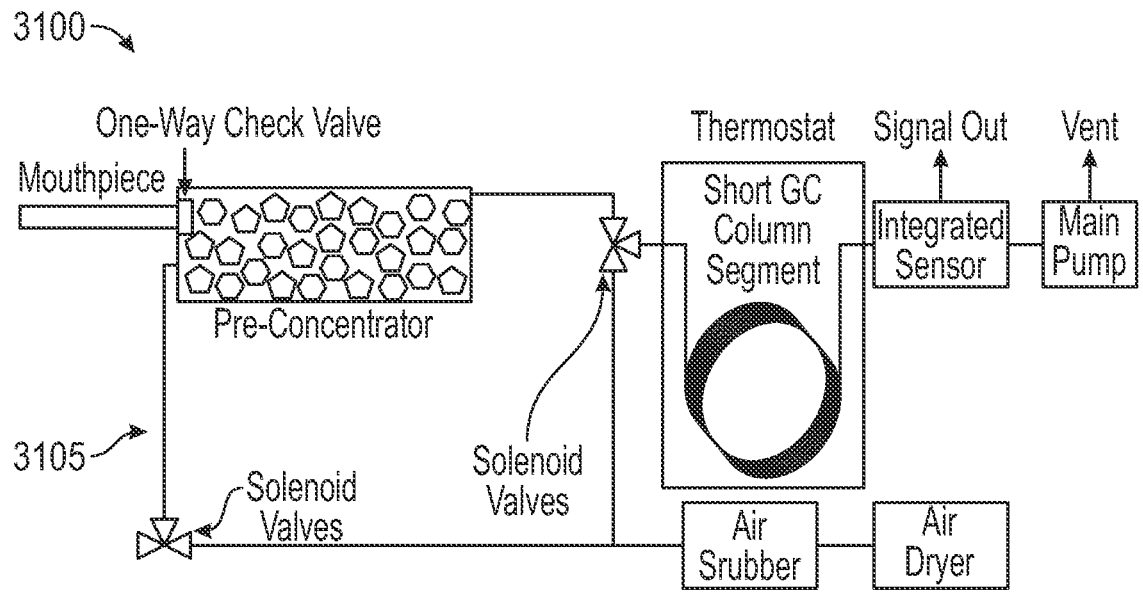
FIG. 31 shows a schematic flow of an illustrative VOC analysis cycle phase of an exemplary MGC hand-held breathalyzer.

FIG. 31 shows a schematic of an exemplary MGC hand-held breathalyzer. The MGC hand-held breathalyzer schematic depicted by FIG. 31 introduces the exemplary MGC hand-held breathalyzer to present the VOC analysis cycle 3100 further depicted by FIGS. 32-35. The MGC hand-held breathalyzer VOC analysis cycle 3100 is an analysis method including multiple stages (phases) described below with reference to FIGS. 31-35. A handheld GC 135 in an exemplary breathalyzer configuration may implement a VOC analysis cycle in accordance with the exemplary VOC analysis cycle 3100 depicted by FIGS. 31-35. The handheld GC 135 breathalyzer processor may be configured to be operable with pumps, valves, sensors, heaters, a GC column, and other components. Some implementations of the depicted design may include a short 3 m segment of MTX-WAX gas chromatography column from RESTEK at 60° C. In an illustrative example, cost of such a short segment may be low, but performs well enough to quickly separate the target substances in the breath. Advantages of the depicted design include the utilization of scrubbed ambient air as a carrier gas, and the utilization of a multisensory integrated platform as a detector. The schematic of the analyzer design shown in FIGS. 31-35 uses a single diaphragm pump and two solenoid microvalves, to reduce the size, weight, and cost of the device. The handheld GC 135 breathalyzer processor may implement the VOC analysis cycle 3100 based on operating at least one valve in combination with activating at least one pump and activating at least one heater as described herein, to separate a test mixture sample in the GC column while capturing a sensor signal. In FIG. 31, the MGC hand-held breathalyzer schematic includes the mouthpiece, pre-concentrator, scrubber, and main pump integrated for fluid coupling with the GC column and the sensor by the solenoid valves. Active elements depicted by FIGS. 31-35 are delineated by dashed lines. In the exemplary VOC analysis cycle 3100 phase 3105 depicted by FIG. 31, the MGC hand-held breathalyzer is in an exemplary inactive mode.

Figure 32:
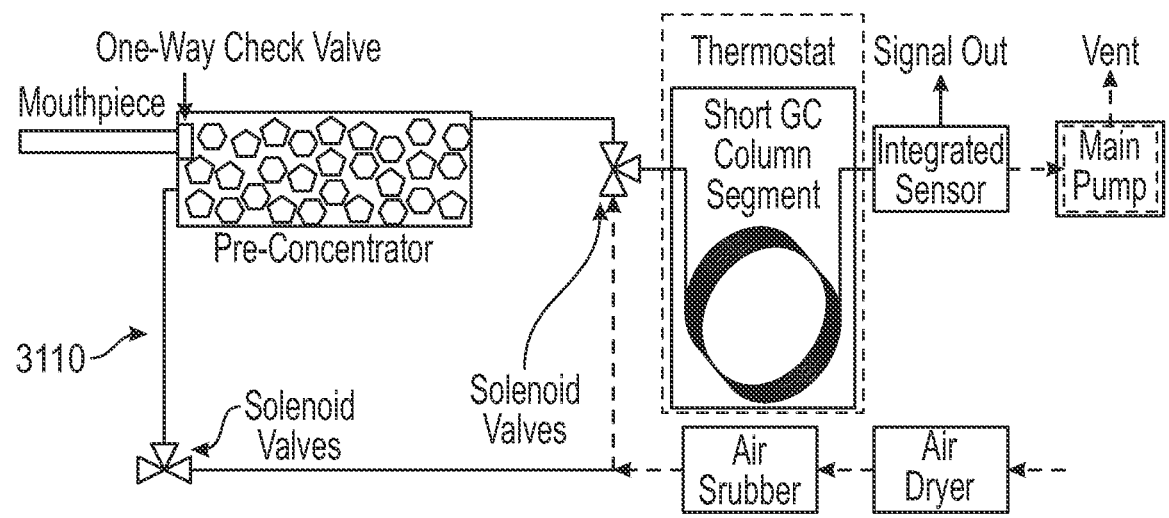
FIG. 32 shows a schematic flow of an illustrative VOC analysis cycle phase of an exemplary MGC hand-held breathalyzer.

FIG. 32 shows a schematic flow of an illustrative VOC analysis cycle phase of an exemplary MGC hand-held breathalyzer. In the exemplary VOC analysis cycle 3100 activation phase 3110 depicted by FIG. 32, when the breathalyzer main switch is turned on, it simultaneously activates the main pump and the column heater (see FIG. 31). The duty cycle of the main pump is chosen to maintain a continuous 14 sccm flow of carrier gas (scrubbed air) through the column. The activated system reaches the stationary baseline (steady state) within 5 min. The activated breathalyzer can perform quick 3 min scans routinely for 5 hours without recharging the battery.

Figure 33:
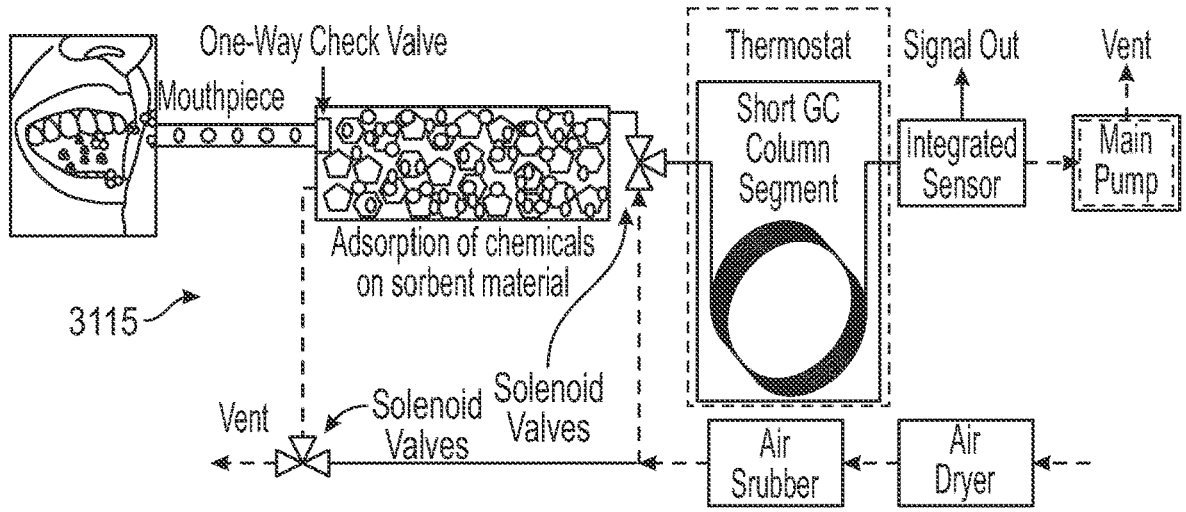
FIG. 33 shows a schematic flow of an illustrative VOC analysis cycle phase of an exemplary MGC hand-held breathalyzer.

FIG. 33 shows a schematic flow of an illustrative VOC analysis cycle phase of an exemplary MGC hand-held breathalyzer. The sample collection initiates when a human subject is blowing into the pre-concentrator through a disposable mouthpiece. In the exemplary VOC analysis cycle 3100 sample collection phase 3115 depicted by FIG. 33, during sample collection, the pre-concentrator is isolated from the rest of the device and the air is flowing from the one-way check valve, through the sorbent material and exhausts through one of the solenoid valves. In some implementations CARBOPACK B is used as a sorbent for trapping VOC molecules from the breath. When the sample collection is complete, the valves close automatically and the heat is applied to the sorbent. By heating up the pre-concentrator with the built-in heater, VOC molecules thermally desorb from the sorbent and remain trapped inside of the pre-concentrator volume (see FIG. 34).

Figure 34:
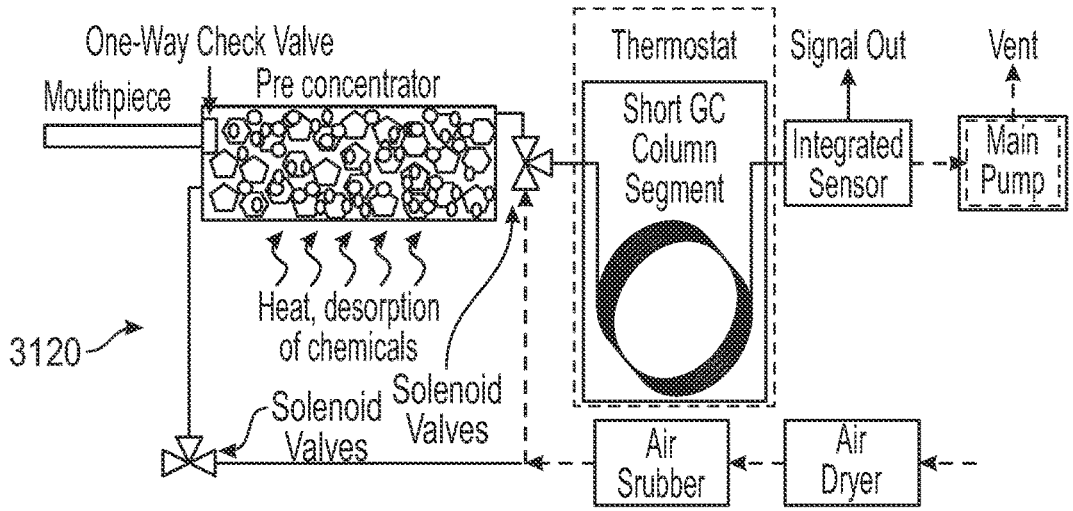
FIG. 34 shows a schematic flow of an illustrative VOC analysis cycle phase of an exemplary MGC hand-held breathalyzer.

FIG. 34 shows a schematic flow of an illustrative VOC analysis cycle phase of an exemplary MGC hand-held breathalyzer. In the exemplary VOC analysis cycle 3100 thermal desorption phase 3120 depicted by FIG. 34, for VOC analysis, the carrier gas is rerouted through the pre-concentrator delivering the trapped VOC molecules to the GC column segment and then to the integrated detector (see FIG. 35).

Figure 35:
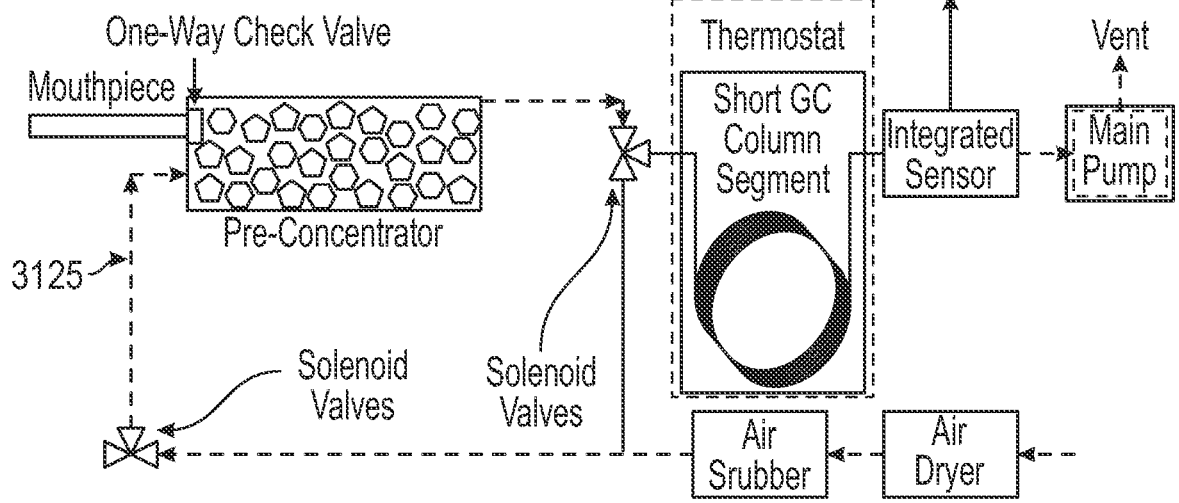
FIG. 35 shows a schematic flow of an illustrative VOC analysis cycle phase of an exemplary MGC hand-held breathalyzer.

FIG. 35 shows a schematic flow of an illustrative VOC analysis cycle phase of an exemplary MGC hand-held breathalyzer. In the exemplary VOC analysis cycle 3100 analysis phase 3125 depicted by FIG. 35, the retention time on the GC column is indicative of the VOC nature. Types of VOCs are identified and the diagnosis may be determined by a pattern recognition algorithm.

Figure 36:
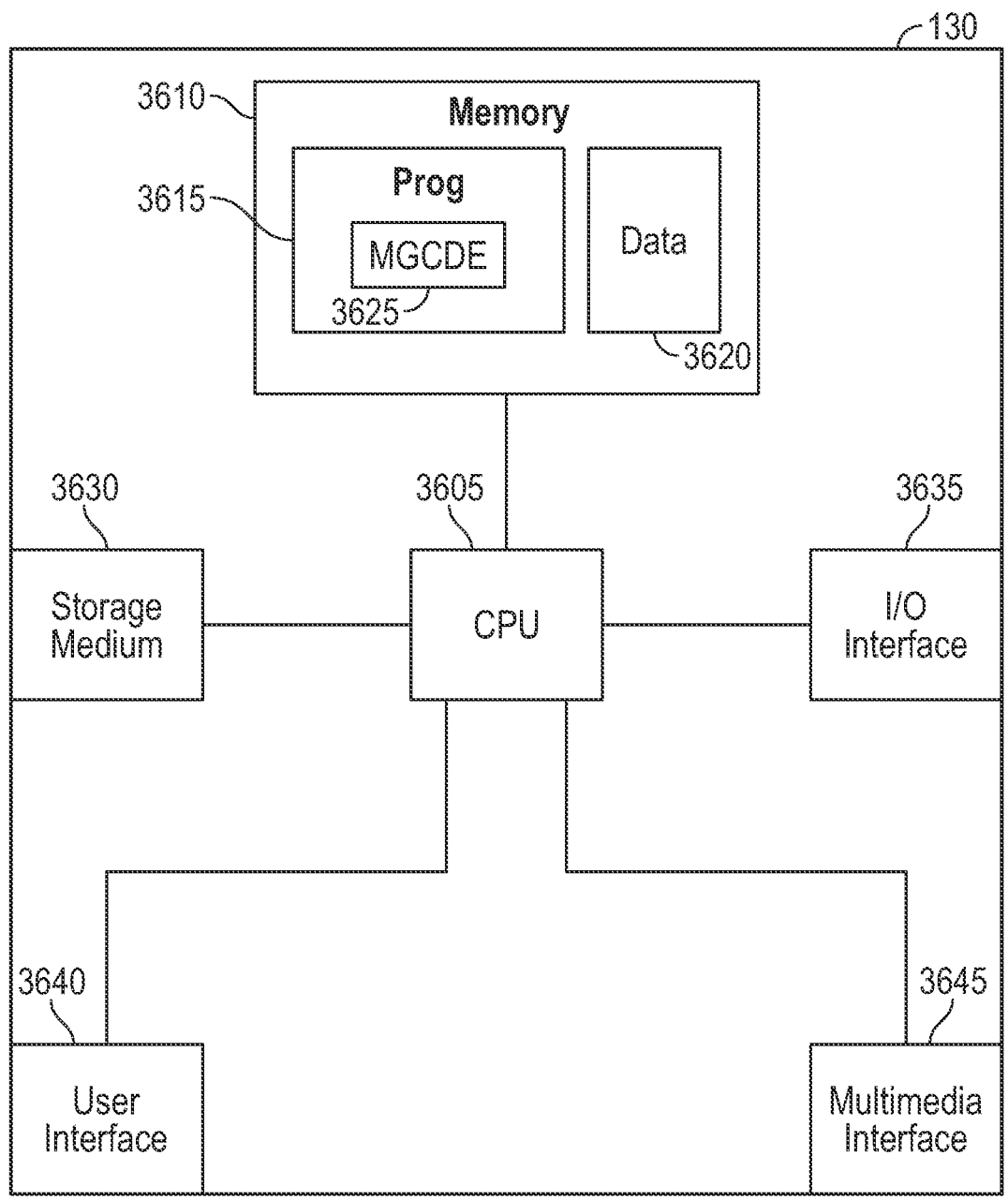
FIG. 36 shows an electronic block diagram of an exemplary MGC configured with a Multisensory Gas Chromatography Diagnosis Engine (MGCDE) to detect and identify a pathogen of interest.

FIG. 36 shows an electronic block diagram of an exemplary MGC configured with a Multisensory Gas Chromatography Diagnosis Engine (MGCDE) to detect and identify a pathogen of interest. The block diagram of the exemplary MGC 130 depicted by FIG. 36 is an exemplary block diagram of the portable GC lab 130, depicted at least by FIG. 1. The block diagram of the exemplary MGC 130 depicted by FIG. 36 is also an exemplary block diagram of the handheld GC 135, depicted at least by FIG. 1. The block diagram of the exemplary MGC 130 depicted by FIG. 36 is also an exemplary block diagram of a handheld GC 135 in an exemplary breathalyzer configuration. In FIG. 36, the block diagram of the exemplary MGC 130 includes processor 3605 and memory 3610. The processor 3605 is in electrical communication with the memory 3610. The depicted memory 3610 includes program memory 3615 and data memory 3620. The depicted program memory 3615 includes processor-executable program instructions implementing the Multisensory Gas Chromatography Diagnosis Engine (MGCDE) 3625. The illustrated program memory 3615 may encode processor-executable program instructions configured to implement an OS (Operating System). The OS may include processor executable program instructions configured to implement various operations when executed by the processor 3605. The OS may be omitted. The illustrated program memory 3615 may encode processor-executable program instructions configured to implement various Application Software. The Application Software may include processor executable program instructions configured to implement various operations when executed by the processor 3605. The Application Software may be omitted. In the depicted implementation, the processor 3605 is communicatively and operably coupled with the storage medium 3630. In the depicted implementation, the processor 3605 is communicatively and operably coupled with the I/O (Input/Output) interface 3635. In the depicted implementation, the I/O interface 3635 includes a network interface. The network interface may be a wireless network interface. The network interface may be a Wi-Fi interface. The network interface may be a Bluetooth® interface. The MGC 130 may include more than one network interface. The network interface may be a wireline interface. The network interface may be omitted. In the depicted implementation, the processor 3605 is communicatively and operably coupled with the user interface 3640. In the depicted implementation, the processor 3605 is communicatively and operably coupled with the multimedia interface 3645. In the illustrated implementation, the multimedia interface 3645 includes interfaces adapted to input and output of audio, video, and image data.

The multimedia interface 3645 may include one or more still image camera or video camera. Useful examples of the illustrated MGC 130 include, but are not limited to, personal computers, servers, tablet PCs, smartphones, or other computing devices. Multiple MGC 130 devices may be operably linked to form a computer network in a manner as to distribute and share one or more resources, such as clustered computing devices and server banks/farms. Various arrangements of such general-purpose multi-unit computer networks suitable for implementations of the disclosure, their typical configuration, and standardized communication links are well known to one skilled in the art. An exemplary MGC 130 design may be realized in a distributed implementation. Some MGC 130 designs may be partitioned between a client device, such as, for example, a phone, and a more powerful server system. An MGC 130 partition hosted on a PC or mobile device may choose to delegate some parts of computation, such as, for example, machine learning or deep learning, to a host server. A client device partition may delegate computation-intensive tasks to a host server to take advantage of a more powerful processor, or to offload excess work. Some MGC 130 devices may be configured with a mobile chip including an engine adapted to implement specialized processing, such as, for example, neural networks, machine learning, artificial intelligence, image recognition, audio processing, or digital signal processing. Such an engine adapted to specialized processing may have sufficient processing power to implement some MGC 130 features. However, an exemplary MGC 130 may be configured to operate on a device with less processing power, such as, for example, various gaming consoles, which may not have sufficient processor power, or a suitable CPU architecture, to adequately support MGC 130. Various implementations configured to operate on a such a device with reduced processor power may work in conjunction with a more powerful server system.

Figure 37:
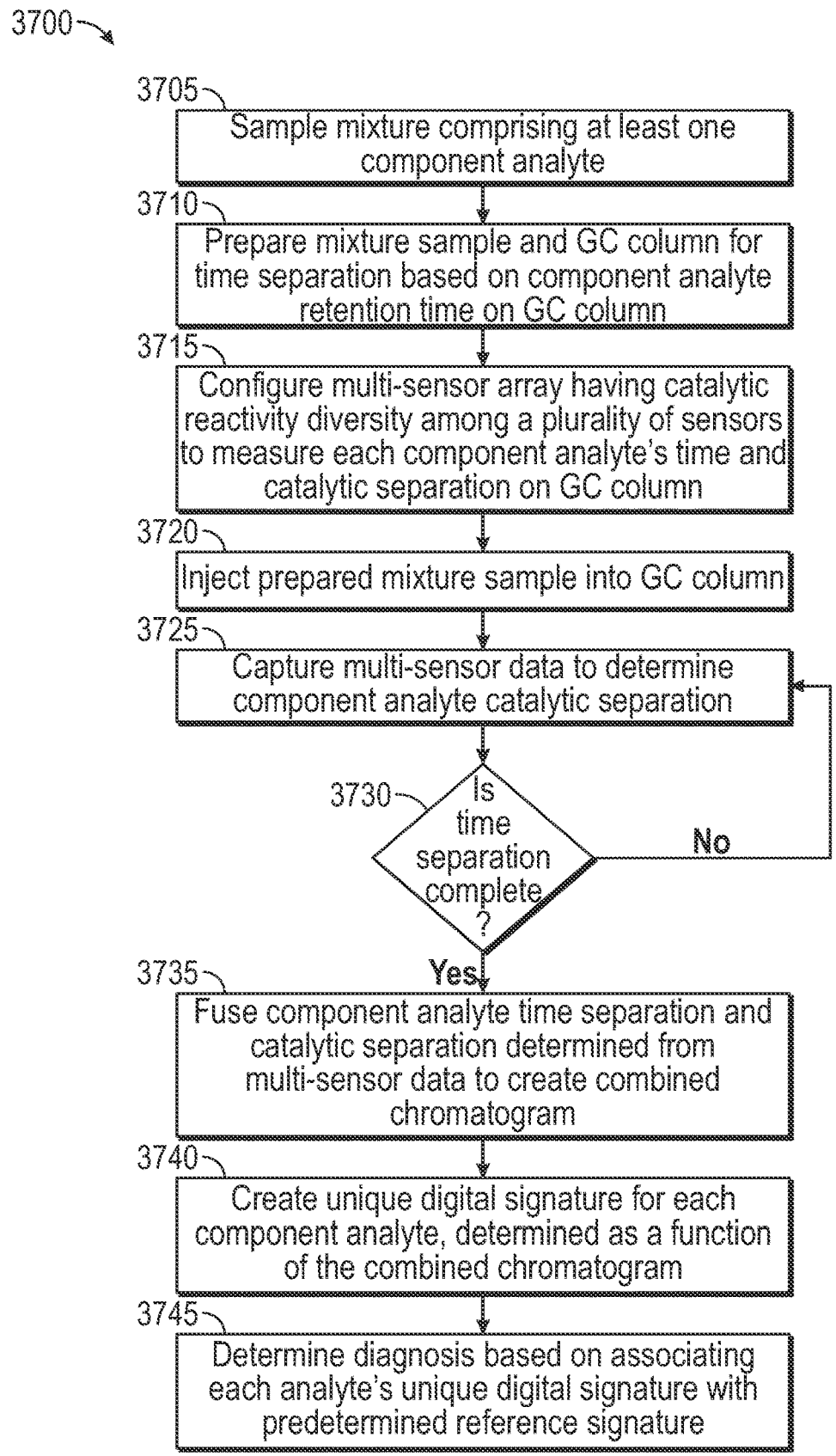
FIG. 37 shows a process flow of an exemplary MGCDE detecting and identifying a pathogen of interest.

FIG. 37 shows a process flow of an exemplary MGCDE detecting and identifying a pathogen of interest. In FIG. 37, the depicted method is given from the perspective of the Multisensory Gas Chromatography Diagnosis Engine (MGCDE) 3625 implemented via processor-executable program instructions executing on the MGC 130 processor 3605, depicted in FIG. 36. In various implementations, the method depicted in FIG. 37 may also be understood by one of ordinary skill as if given from the perspective of the handheld GC 135 in exemplary micro-GC or breathalyzer configurations, implemented via processor-executable program instructions executing on a processor configured in the handheld GC 135. In the illustrated implementation, the MGCDE 3625 executes as program instructions on the processor 3605 configured in the MGCDE 3625 host MGC 130 or handheld GC 135, depicted in at least FIG. 1. In some implementations, the MGCDE 3625 may execute as a cloud service communicatively and operatively coupled with system services, hardware resources, or software elements local to and/or external to the MGCDE 3625 host MGC 130 or handheld GC 135.

The processor-executable program instructions executing on the processor 3605 may implement the method 3700 based on operating at least one valve in combination with activating at least one pump and activating at least one heater as described herein, to separate a test mixture sample in the GC column while capturing a sensor signal. The processor 3605 may be configured to activate one or more sensor. In some implementations, one or more heater may not be connected to the processor 3605, and instead of the heater being configured to be activated by the processor, the heater may be configured that the heater is activated when one or more sensor is activated, wherein when the sensor is on, the heater is also on. In some implementations, the activity of one or more heater may be modulated by the processor 3605.

The depicted method 3700 begins at step 3705 with the processor 3605 sampling a mixture comprising at least one chemical component analyte.

Then, the method continues at step 3710 with the processor 3605 preparing the mixture sample and GC column for time separation based on component analyte retention time on the GC column.

Then, the method continues at step 3715 with the processor 3605 configuring a multi-sensor array having catalytic reactivity diversity among a plurality of sensors to measure each chemical component analyte's time separation and catalytic separation on the GC column.

Then, the method continues at step 3720 with the processor 3605 injecting the prepared mixture sample into the GC column.

Then, the method continues at step 3725 with the processor 3605 capturing multi-sensor data to determine chemical component analyte catalytic separation.

Then, the method continues at step 3730 with the processor 3605 performing a test to determine if the time separation is complete. The processor 3605 may determine if the time separation is complete based on the retention time of the heaviest analyte in the mixture sample.

Upon a determination by the processor 3605 at step 3730 that time separation is not complete, the method continues at step 3725 with the processor 3605 capturing multi-sensor data. Upon a determination by the processor 3605 at step 3730 that time separation is complete, the method continues at step 3735.

At step 3735, the processor 3605 fuses component analyte time separation and catalytic separation determined from multi-sensor data to create a combined chromatogram.

Then, the method continues at step 3740 with the processor 3605 creating a unique digital signature for each component analyte, determined as a function of the combined chromatogram.

Then, the method continues at step 3745 with the processor 3605 determining a diagnosis or identifying a pathogen of interest, based on associating each analyte's unique digital signature with a predetermined reference signature.

In some implementations, the method may repeat. In various implementations, the method may end.

Although various features have been described with reference to the Figures, other implementations of the various features are possible. For example, GC operations may be governed by a Proportional Integral Derivative (PID) algorithm. The PID algorithm may be implemented, for example, by the MGC 130 or handheld GC 135 processor.

In an illustrative example, the MGC 130 or handheld GC 135 processor may perform several functions, including but not limited to examples such as: Head Pressure Routine; Column PID update; Critical Error Detection; Update Control state machine; Check for commands from the Control Program; and, Data collection Routine; each of which are briefly described below.

Head Pressure Routine

Hysteresis control routine: In an illustrative example, flow rate is calculated as a function of the inner volume of the column, pressure, and viscosity of the carrier gas. Flow rate is adjusted by the pressure generated by the pump. Readings from the pressure sensor are compared to upper and lower limits of the pressure setting +/−0.5 KPa. A pump run timer is updated based on the pressure reading. A minimum time of 2 ms is needed for the pump to begin to generate pressure, longer times may be necessary depending on the pressure difference.

Column PID Update

In an illustrative example, a PID algorithm may be used to regulate the temperature of the column. The voltage of a thermistor is measured and converted to Celsius. The PID output is recalculated to adjust the duty cycle of the power applied to the heater.

Critical Error Detection

In an illustrative example, checks for errors that could cause harm to the GC if operation continues. Checks for failures of the temperature or pressure sensors. Checks for failures of the heater or pressure pumps (over/under maximum and minimum values). If any critical errors occur, then all outputs are immediately disabled and an error message detailing the failure is sent the control program.

Update Control State Machine

In an illustrative example, the Control State Machine controls the stages of GC operation. The state machine update executes every time the main loop cycles. States control IO status for various and provides status to the control program. Criteria for each stage must be met before proceeding to the next stage. (Ex. Temperature must stabilize before the system can reach Idle or the data collection time must be reached before the system advances to the purge cycle). Stages of operation include: Initialization—Initial setup of setting all outputs into their default state (only runs once when powered up); Pressurization—A checkpoint to ensure the pressure setpoint is reached. This is important to check for leaks or failed pumps; Column Warmup—The column must reach its operating temperature and remain stable at the temperature for a minimum about of time before the system is considered ready; Idle—No special functions. The GC is now ready to perform samples; The GC returns to Idle after completing a sample run and purging the pre-concentrator; Sample Collection—A sample is pulled by the Sample Pump through the Pre-concentrator or Sample Loop for a specified time; Sample Preheat—The pre-concentrator's fan is turned off and its heater is turned on to thermally desorb the sample; Sample Inject—Valves are switched to change the flow path and push the sample into the GC for a specified time; Data Collection—Valves are turned and the pre-concentrator heater are turned off. The pre-concentrator fan is turned back on to cool the system. Data from the chemical sensor is collected for a specified time; Purge—Valve 2 is turned on, the pre-concentrator heater is turned on and the pre-concentrator fan are turned off. These changes force carrier gas backwards through the pre-concentrator or sample loop to purge the system of any potentially remaining sample. At the end of this cycle the GC returns to the Idle state to prepare for the next sample.

Check for Commands from the Control Program

In an illustrative example, if the GC receives commands from the control program they are processed to determine if they are in a valid format. If valid commands are received, they are then processed to perform the specified action. Commands can range from adjusting variables in the GC (Temperature, Pressure, Timing) to recalling data (retrieving previous setpoints) or Starting/aborting a sample cycle.

Data Collection Routine

In an illustrative example, data from the chemical sensor is collected for a specified time.

In an illustrative example, various implementations in accordance with the present disclosure may be based on principles of analytical gas chromatography (GC) and utilize a novel highly integrated multisensory detector, also known as electronic nose or Enose. Via implementation of a multisensory detector, the device collects multiple chromatograms in a single run. The sensors in the integrated MEMS platform are near-orthogonal and possess very distinct catalytic properties. Hence, the time separation by chromatographic column is complemented by catalytic separation by a multisensory detector. The outcome of this GC/Enose hybrid technology is the ability to monitor a very broad range of analytes from light to heavy on a relatively short and compact GC column in a short period of time of 12.5 min. Also, the device can perform the analysis in a broad range of concentrations from sub-ppb to 100% for most of the analytes of interest.

Various sensor structure designs may include holes or apertures located in the layers so that holes overlap to form a curved or bent edge as abutting layers are stacked. In an illustrative example, an artisan of ordinary skill should appreciate that structures herein disclosed at least with reference to FIGS. 1, 2, 3, 9, 10, 11A-B, 12A-B, 13, 14A-F, 16A-16E, and 17A-17C may include at least one cavity, channel, or chamber defined by holes located in the layers so the holes would overlap to form a curved or bent edge as abutting layers are stacked. Some sensor structure implementations in accordance with the present disclosure may include at least one cavity, channel, or chamber with bends having curved edges resulting from holes overlapping between layers to form a structural edge disposed at an angle offset from an axis perpendicular with the planes of the stacked layers' major planar surfaces. In an example illustrative of various sensor structure implementations, each layer may be in contact with, or abutting, another layer. Each layer of an exemplary sensor structure may be in contact with another layer such that the layers in contact with each other are not separated by something that is not a layer. Each layer of an exemplary sensor structure may be in contact with, or abutting, another layer along the layers' major (planar) surfaces. For example, in an exemplary sensor structure design, layers may be abutting along planar major surfaces, wherein the holes in adjoining or abutting layers overlap.

For example, the present disclosure with reference at least to FIGS. 1, 2, and 3 depicts multiple exemplary channel bend 122 structural features defining curved or bent edges in the exemplary channel 124. Each exemplary channel 124 bend 122 may result from holes located in the layers so the holes would overlap to form the curved or bent edges as abutting layers are stacked. An artisan of ordinary skill would appreciate that a channel 124 bend 122 having a desired radius may be formed based on adjusting the number of layers, the layer thickness, and the locations of holes in the layers, such that the holes located in the layers would overlap to form a curved or bent edge defined by the hole interior edges, as abutting layers are stacked. In an illustrative example, a sensor structure having a channel defined by holes located in the layers so the holes would overlap to form a curved or bent edge as abutting layers are stacked may result in improved flow in the channel. Improved flow in the channel may improve the accuracy or usefulness of analysis obtained using the channel, based on improved flow as a result of reduced resistance to flow in the channel. For example, replacing a channel having stepwise perpendicular interior edges defined by overlapping holes in only a few layers, with a smoother channel 124 bend 122 defined by holes offset from layer to layer of a greater number of thinner layers, may result in reduced flow resistance. In an illustrative example, an artisan of ordinary skill would recognize that as the number of layers is increased and the thickness of the layers with overlapping apertures is reduced, an exemplary channel 124 bend 122 could become smoother in contrast with the stepwise perpendicular interior edges defined by overlapping holes in only a few layers. The depicted sensor structures having bent curved top or bottom edges that comprise channel 124 bend 122 features may be a result of Applicant's "cavity defined by overlapping holes through abutting layers" features. For example, the disclosed sensor structure and method to make may include holes that overlap between layers to form a structural edge disposed at an angled offset from a line perpendicular with the stacked layers' planar major surfaces. As depicted at least by FIGS. 1, 2, and 3, the curved edges that may result may extend through multiple layers, as the holes overlap from layer to layer.

In an illustrative example, a portable GC lab implementation is the most general case, discussing a device for identifying various pathogens by their volatile traces. In this disclosure we are mainly discussing bacterial pathogens, sniffing infectious wounds and bacterial colonies. However, we do mention the possibility of diagnostics of diseases by breath and possible diagnostics of COVID-19 as well. The device is compact. Some implementations may be hand-held. The time of scan is about 30 min, which is reasonable for this application. A sampling pump is included for the active sample intake.

In an illustrative example, a handheld GC implementation has no sampling pump—the lungs work as a pump injecting the sample into the device. The time of scan for the target COVID biomarkers may be under 3 minutes.

In an illustrative example, SARS-CoV-2 is a novel coronavirus that has recently been identified as the causative agent of COVID-19, a respiratory disease that exhibits a wide range of clinical outcomes from asymptomatic and mild disease to severe viral pneumonia, Acute Respiratory Distress Syndrome (ARDS), Multisystem Inflammatory Syndrome in Children (MIS-C), acute kidney injury, thrombotic disorders, and serious cardiac, cerebrovascular, and vascular complications.

As the COVID-19 pandemic continues to spread, early identification of SARS-CoV-2 infected individuals is pivotal in interrupting infection chains. With the tentative opening of many states came an increase in COVID-19 cases, thus, there is a critical need for nontraditional testing technologies that are non-invasive, not reagent intensive, and that do not take a long time to gather results. It is highly desirable for an accurate and sensitive system that can provide results in real time and is mobile/portable and deployable in any clinical, community and everyday setting. Current testing technologies are not practical for field use, requiring expensive reagents and enzymes and laboratories certified for potentially virulent samples. These tests are cumbersome to perform as they use aqueous solutions, require multiple steps and hours, if not days, to get results.

Volatile organic compounds (VOCs) produced during respiratory infections can cause specific signatures, which can be detected by analytical instrumentation with a high rate of precision. The oral cavity is excellent for noninvasive VOC detection because it is readily accessible. For example, exhaled breath could be captured and analyzed for direct detection of the respiratory tract infection from unique volatile organic metabolite byproducts of SARS-CoV2 infection. VOCs from the oral cavity offer opportunities for continuous or periodic monitoring of viral infection and disease presentation.

There are two interesting approaches for analysis of VOCs in the breath. The first approach utilizes analytical instrumentation, such as gas chromatography (GC) and mass spectrometry (MS). Conventional laboratory GC/MS systems are capable of providing a comprehensive analysis of complex VOC samples, but are not suitable for monitoring of VOCs in the field due to their bulky size, heavy weight, high cost, long time of scan, special carrier gases requirement and high maintenance.

The second approach is based on utilization of integrated multisensory systems, also known as electronic noses (Enoses). An electronic nose is a biologically inspired device, which consists of a mechanism for chemical detection, such as an array of electronic sensors, and a mechanism for pattern recognition, such as a neural network. A VOC stimulus generates a characteristic fingerprint (or electronic signature) from the sensor array. Patterns or fingerprints from known VOCs are used to construct a database and train a pattern recognition system to classify and identify unknown VOCs.

Enoses are significantly more compact than analytical instrumentation and can be deployed in a hand-held form. However, after almost 30 years of research and development by numerous scientists and engineers, the electronic noses are still not fully commercialized. The reason for that is the difficulties with analysis on multicomponent mixtures. Since the human breath may contain hundreds of chemical compounds with variations in concentration, training and calibration of electronic noses becomes a time-consuming process, which requires testing in almost any possible background. This complicates scaling and commercialization of such technologies.

Signature metabolites released in the body from viral pathogen infections and bacteria of various infectious diseases during their lifecycle produce volatile organic compounds (VOCs) that can be used as unique chemical signatures of the disease for diagnostics. Chemical signatures of various diseases were successfully detected by a portable gas chromatograph (GC) equipped with novel multisensory solid-state detector, also known as electronic nose or Enose. Thanks to the ultra-high sensitivity and quick response of the detector, the unique identifiers of diseases can be obtained.

In an illustrative example, an exemplary Portable Lab implementation may be primarily configured to sniff bacterial metabolites. For example, an exemplary portable lab can sniff and identify bacteria. In contrast, an exemplary Breathalyzer implementation may be primarily configured to sniff the chemical response to viruses in the breath of an infected person, that is, sniffing the response of a human body to viruses, without actually sniffing the virus itself. However, a Portable Lab implementation may also be configured to detect COVID-19 using this technology. In an illustrative example, while a Breathalyzer implementation may use GC principles and components, the Breathalyzer implemented in accordance with the present disclosure may not be useful as a classical GC for general chemical analysis applications, and instead may find most effective applications limited to breath analysis. In contrast, a Portable Lab implementation in accordance with the present disclosure may be useful in a broad range of chemical analysis applications. In an illustrative example, the glass 3D-GC disclosure is an ideal design for both Portable Lab and the Breathalyzer technologies. Both Portable Lab and the Breathalyzer devices implemented in accordance with the present disclosure may be glass-printed. The technology can be used for on-site chemical analysis at the civilian & defense government facilities, specialized in: oil & gas production and distribution, petrochemical, pharmaceutical, water & wastewater, thermal power, food & beverages, pulp & paper, metal & mining, cement & glass, and other utilizing chemically active substances. The technology performs successfully in humid and contaminated environments.

COVID-19 is a respiratory disease that appears to have among other effects irreversible damage to the lungs. It is therefore likely that in response to the primary pathogen there are signature imprints in the lungs and likely elsewhere in the body such as in the breath, saliva, blood, urine, and fecal material that produce metabolites that are detectable by the proposed technology. In addition to signature metabolites in the human body in response to the primary pathogen, there may also be resulting secondary disease and/or pathogens that also produce signature metabolites in the human body to as a result of the primary COVID-19 pathogen.

The current demand for advanced COVID-19 breathalyzers requires a paradigm shift in sensor design. The use of bulky analytical instrumentation is not applicable in the field. At the same time, the idea of utilizing a multisensory array alone, without a proper designed sampling system for breath analysis, is not very practical either.

The most efficient approach for advanced COVID-19 breathalyzer is to use a hybrid technology utilizing the features of analytical instruments and Enoses in a single product, so that they would be enhancing and reinforcing each other. A breathalyzer implementation in accordance with the present disclosure is small and inexpensive, but at the same time is sensitive, selective, robust, and suitable for quick scans. The measurements are repeatable and reproducible regardless of the background complexity. Based on several recent studies, the target VOCs for viral diseases include aldehydes, ketones, and spirits. In particular, the target compounds for COVID-19 supported by recent research on human subjects are Butyraldehyde, Isopropanol and Ethyl Butyrate. Preliminary testing of COVID-19 biomarkers was conducted a compact setup equipped with the advanced multisensory detector (described with reference to at least FIGS. 22A-E) in accordance with the present disclosure. The system implemented in accordance with the present disclosure was able to identify and quantify those compounds with high sensitivity, selectivity and in short periods of approximately 3 minutes (described with reference to at least FIG. 30).

In an illustrative example, a breathalyzer in accordance with the present disclosure is envisioned to be used in a hospital, clinic setting, community or even home and workplace. For example, instead of taking temperatures at entrances to establishments, the disclosed device may be used for more informative and accurate data. The danger of contamination is minimal thanks to the self-cleaning preconcentrator and a disposable mouthpiece. Additionally, the disclosed analyzer may be able to differentiate between COVID-negative and COVID-positive-asymptomatic subjects.

In an illustrative example, in the current COVID-19 epidemic, this quick screening device would enable doctors to detect and diagnose COVID-19 symptomatic and asymptomatic individuals leading to appropriate treatment and/or quarantine procedures. In the long run, the disclosed analyzer is not limited to COVID-19 diagnosis, and can be readily adapted to other pandemics, as well as for the detection of other diseases and conditions.

Identification of at least the following pathogens have been successfully tested by portable GC technology implemented in accordance with the present disclosure: 1) empty plate for background measurements, 2) MSSA, 3) MRSA, 4) *Pseudomonas aeruginosa,* 5) *Proteus mirabilis,* 6) *Streptococcus pneumoniae,* 7) *Enterococcus faecalis,* 8) *Klebsiella pneumoniae,* 9) *E.coli,* 10) *Enterobacter cloacae,* and 11) *Acinetobacter baumanii.* In an illustrative example, the identification and susceptibility antibiogram report was printed, and all patient-identifying information was blacked out and collected separately for further analysis. All the tested bacteria demonstrated distinct and stable VOC patterns. Circled peaks belong to the electronic signatures of the pathogens. The experiment was repeated over the course of 10 weeks and the characteristic features were verified. For each of the studied pathogens, the pattern of VOCs was found to be the same in all the 10 experiments.

In the Summary above and in this Detailed Description, and the Claims below, and in the accompanying drawings, reference is made to particular features of various implementations. It is to be understood that the disclosure of particular features of various implementations in this specification is to be interpreted to include all possible combinations of such particular features. For example, where a particular feature is disclosed in the context of a particular aspect or implementation, or a particular claim, that feature can also be used—to the extent possible—in combination with and/or in the context of other particular aspects and implementations, and in an implementation generally.

While multiple implementations are disclosed, still other implementations will become apparent to those skilled in the art from this detailed description. Disclosed implementations may be capable of myriad modifications in various obvious aspects, all without departing from the spirit and scope of the disclosed implementations. Accordingly, the drawings and descriptions are to be regarded as illustrative in nature and not restrictive.

It should be noted that the features illustrated in the drawings are not necessarily drawn to scale, and features of one implementation may be employed with other implementations as the skilled artisan would recognize, even if not explicitly stated herein. Descriptions of well-known components and processing techniques may be omitted so as to not unnecessarily obscure the implementation features.

In the present disclosure, various features may be described as being optional, for example, through the use of the verb "may;" or, through the use of any of the phrases: "in some implementations," "in some designs," "in various implementations," "in various designs," "in an illustrative example," or, "for example." For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be implemented in seven different ways, namely with just one of the three possible features, with any two of the three possible features or with all three of the three possible features.

In various implementations, elements described herein as coupled or connected may have an effectual relationship realizable by a direct connection or indirectly with one or more other intervening elements.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various implementations have been disclosed and described in detail herein, it will be apparent to those skilled in the art that various changes may be made to the disclosed configuration, operation, and form without departing from the spirit and scope thereof. In particular, it is noted that the respective implementation features, even those disclosed solely in combination with other implementation features, may be combined in any configuration excepting those readily apparent to the person skilled in the art as nonsensical. Likewise, use of the singular and plural is solely for the sake of illustration and is not to be interpreted as limiting.

The Abstract is provided to comply with 37 C. F. R. § 1.72(b), to allow the reader to quickly ascertain the nature of the technical disclosure and is submitted with the understanding that it will not be used to interpret or limit the scope or meaning of the claims.

In the present disclosure, all descriptions where "comprising" is used may have as alternatives "consisting essentially of," or "consisting of." In the present disclosure, any method or apparatus implementation may be devoid of one or more process steps or components. In the present disclosure, implementations employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an implementation "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

Many suitable methods and corresponding materials to make each of the individual parts of implementation apparatus are known in the art. One or more implementation part may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins, and elastomers as may be described hereinabove may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112 (f). Specifically, any use of "step of" in the claims herein is not intended to invoke the provisions of 35 U.S.C. § 112 (f). Elements recited in means-plus-function format are intended to be construed in accordance with 35 U.S.C. § 112 (f).

Recitation in a claim of the term "first" with respect to a feature or element does not necessarily imply the existence of a second or additional such feature or element.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The terms "abutting" or "in mechanical union" refer to items that are in direct physical contact with each other, although the items may not necessarily be attached together.

The word "exemplary" is used herein to mean "serving as an example, instance, or illustration." Any implementation described herein as "exemplary" is not necessarily to be construed as preferred over other implementations. While various aspects of the disclosure are presented with reference to drawings, the drawings are not necessarily drawn to scale unless specifically indicated.

Reference throughout this specification to "an implementation" or "the implementation" means that a particular feature, structure, or characteristic described in connection with that implementation is included in at least one implementation. Thus, the quoted phrases, or variations thereof, as recited throughout this specification are not necessarily all referring to the same implementation.

Similarly, it should be appreciated that in the above description, various features are sometimes grouped together in a single implementation, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects may lie in a combination of fewer than all features of any single foregoing disclosed implementation. Thus, the claims following this Detailed Description are hereby expressly incorporated into this Detailed Description, with each claim standing on its own as a separate implementation. This disclosure is intended to be interpreted as including all permutations of the independent claims with their dependent claims.

A system or method implementation in accordance with the present disclosure may be accomplished through the use of one or more computing devices. For example, as depicted by and described with reference to at least FIG. 36 and FIG. 37, one of ordinary skill in the art would appreciate that an exemplary system appropriate for use with implementation in accordance with the present application may generally include one or more of a Central processing Unit (CPU), Random Access Memory (RAM), a storage medium (e.g., hard disk drive, solid state drive, flash memory, cloud storage), an operating system (OS), one or more application software, a display element, one or more communications means, or one or more input/output devices/means. Examples of computing devices usable with implementations of the present disclosure include, but are not limited to, proprietary computing devices, personal computers, mobile computing devices, tablet PCs, mini-PCs, servers, or any combination thereof. The term computing device may also describe two or more computing devices communicatively linked in a manner as to distribute and share one or more resources, such as clustered computing devices and server banks/farms. One of ordinary skill in the art would understand that any number of computing devices could be used, and implementation of the present disclosure are contemplated for use with any computing device.

In various implementations, communications means, data store(s), processor(s), or memory may interact with other components on the computing device, in order to effect the provisioning and display of various functionalities associated with the system and method detailed herein. One of ordinary skill in the art would appreciate that there are numerous configurations that could be utilized with implementations of the present disclosure, and implementations of the present disclosure are contemplated for use with any appropriate configuration.

According to an implementation of the present disclosure, the communications means of the system may be, for instance, any means for communicating data over one or more networks or to one or more peripheral devices attached to the system. Appropriate communications means may include, but are not limited to, circuitry and control systems for providing wireless connections, wired connections, cellular connections, data port connections, Bluetooth® connections, or any combination thereof. One of ordinary skill in the art would appreciate that there are numerous communications means that may be utilized with implementations of the present disclosure, and implementations of the present disclosure are contemplated for use with any communications means.

Throughout this disclosure and elsewhere, block diagrams and flowchart illustrations depict methods, apparatuses (i.e., systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general purpose hardware and computer instructions; and so on—any and all of which may be generally referred to herein as a "circuit," "module," or "system."

While the foregoing drawings and description may set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an implementation may include an alternate order of the steps adapted to a particular application of a technique disclosed herein. All such variations and modifications are intended to fall within the scope of this disclosure. The depiction and description of steps in any particular order is not intended to exclude implementations having the steps in a different order, unless required by a particular application, explicitly stated, or otherwise clear from the context.

Traditionally, a computer program consists of a sequence of computational instructions or program instructions. It will be appreciated that a programmable apparatus (that is, computing device) can receive such a computer program and, by processing the computational instructions thereof, produce a further technical effect.

A programmable apparatus may include one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computer can include any and all suitable combinations of at least one general purpose computer, special-purpose computer, programmable data processing apparatus, processor, processor architecture, and so on.

It will be understood that a computer can include a computer-readable storage medium and that this medium may be internal or external, removable, and replaceable, or fixed. It will also be understood that a computer can include a Basic Input/Output System (BIOS), firmware, an operating system, a database, or the like that can include, interface with, or support the software and hardware described herein.

Implementations of the system as described herein are not limited to applications involving conventional computer programs or programmable apparatuses that run them. It is contemplated, for example, that implementations of the disclosure as claimed herein could include an optical computer, quantum computer, analog computer, or the like.

Regardless of the type of computer program or computer involved, a computer program can be loaded onto a computer to produce a particular machine that can perform any and all of the depicted functions. This particular machine provides a means for carrying out any and all of the depicted functions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Computer program instructions can be stored in a computer-readable memory capable of directing a computer or other programmable data processing apparatus to function in a particular manner. The instructions stored in the computer-readable memory constitute an article of manufacture including computer-readable instructions for implementing any and all of the depicted functions.

A computer readable signal medium may include a propagated data signal with computer readable program code encoded therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code encoded by a computer readable medium may be transmitted using any appropriate medium, including but not limited to wireless, wireline, optical fiber cable, RF, etc., or any suitable combination of the foregoing.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software modules, or as modules that employ external routines, code, services, and so forth, or any combination of these. All such implementations are within the scope of the present disclosure.

Unless explicitly stated or otherwise clear from the context, the verbs "execute" and "process" are used interchangeably to indicate execute, process, interpret, compile, assemble, link, load, any and all combinations of the foregoing, or the like. Therefore, implementations that execute or process computer program instructions, computer-executable code, or the like can suitably act upon the instructions or code in any and all of the ways just described.

The functions and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the art, along with equivalent variations. In addition, implementations of the disclosure are not described with reference to any particular programming language. It is appreciated that a variety of programming languages may be used to implement the present teachings as described herein, and any references to specific languages are provided for disclosure of enablement and best mode of implementations of the disclosure. Implementations of the disclosure are well suited to a wide variety of computer network systems over numerous topologies. Within this field, the configuration and management of large networks include storage devices and computers that are communicatively coupled to dissimilar computers and storage devices over a network, such as the Internet.

In the foregoing description, it will be readily appreciated by those skilled in the art that modifications may be made to the invention without departing from the concepts disclosed herein. Such modifications are to be considered as included in the following claims, unless the claims by their language expressly state otherwise. Variations described for exemplary embodiments of the present invention can be realized in any combination desirable for each particular application. Thus, particular limitations, and/or embodiment enhancements described herein, which may have particular limitations, need be implemented in methods, systems, and/or apparatuses including one or more concepts describe with relation to exemplary embodiments of the present invention.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present invention should not be limited by any of the above-described exemplary embodiments.

A number of implementations have been described. Nevertheless, it will be understood that various modifications may be made. For example, the steps of the disclosed techniques may be performed in a different sequence, components of the disclosed systems may be combined in a different manner, or the components may be supplemented with other components. Accordingly, other implementations are contemplated, within the scope of the following claims.

What is claimed is:

1. An apparatus comprising:
  at least four abutting planar layers of flexible flat glass comprising at least one cavity formed by individual overlapping apertures through the thickness of and having an opening central axis substantially perpendicular to the plane of at least two of the planar layers, wherein the at least one cavity comprises a plurality of chambers, wherein the central axis follows a path that alternates between a linear path and a curvilinear path, and wherein at least one chamber of the plurality of chambers is configured to be in fluid coupling with at least one other chamber.

2. The apparatus of claim 1, wherein the at least one cavity having the opening central axis following the curvilinear path that alternates between a linear path and a curvilinear path further comprises a Gas Chromatograph (GC) column.

3. The apparatus of claim 2, wherein the GC column further comprises the at least one chamber extending substantially across the length of at least one planar layer.

4. The apparatus of claim 2, wherein the GC column further comprises the at least one chamber forming a spiral disposed substantially parallel to the plane of at least one planar layer, and wherein the path followed by the opening central axis alternates from a first linear path substantially parallel to the plane of at least one planar layer, to a curvilinear path defined by the spiral, and to a second linear path substantially parallel with the plane of at least one planar layer.

5. The apparatus of claim 1, wherein the apparatus further comprises a valve configured to govern the fluid coupling interchangeably between a coupled and an uncoupled state.

6. The apparatus of claim 1, wherein the apparatus further comprises a sensor that is on top of or in plane with at least one of the flat glass layers.

7. The apparatus of claim 1, wherein the apparatus further comprises a heater that is on top of or in plane with at least one of the flat glass layers.

8. The apparatus of claim 1, wherein the plurality of chambers is at least four chambers.

9. The apparatus of claim 1, wherein the at least one cavity further comprises at least one bend.

10. The apparatus of claim 9, wherein the at least one bend is defined by apertures disposed in at least two planar layers.

11. The apparatus of claim 1, wherein the at least one cavity further comprises at least one bend defined by apertures disposed in more than two planar layers.

12. The apparatus of claim 1, wherein at least one planar layer includes a plurality of apertures having different sizes.

13. The apparatus of claim 1, wherein at least one planar layer includes a plurality of apertures having different shapes.

14. The apparatus of claim 1, wherein the plurality of chambers further comprises at least four chambers, and wherein at least one chamber is configured to be in fluid communication with at least one other chamber, and wherein the fluid communication is governed by a valve configured to be in fluid coupling with at least one chamber of the plurality of chambers.

15. The apparatus of claim 1, wherein the at least one cavity further comprises a Gas Chromatograph (GC) column defined by overlapping apertures through a plurality of the flexible flat glass layers, and wherein the GC column further comprises at least one bend defined by apertures disposed in more than two flexible flat glass layers.

16. The apparatus of claim 1, wherein the at least one cavity further comprises an injector defined by overlapping apertures through a plurality of the flexible flat glass layers.

17. The apparatus of claim 1, wherein the at least one cavity further comprises a pre-concentrator tube defined by overlapping apertures through a plurality of the flexible flat glass layers, and wherein the apparatus further comprises a mouthpiece configured to be fluidly coupled with the pre-concentrator tube.

18. The apparatus of claim 1, wherein the apparatus further comprises a pump configured to be in fluid coupling with at least one chamber of the plurality of chambers.

19. The apparatus of claim 1, wherein the apparatus further comprises at least one 3D printed sensor that is on top of or in plane with at least one of the flat glass layers.

20. The apparatus of claim 1, wherein the apparatus further comprises a mouthpiece configured to be in fluid coupling with at least one chamber of the plurality of chambers.

21. The apparatus of claim 1, wherein the apparatus further comprises at least one of the abutting planar layers of flexible flat glass is configured to admit ultraviolet (UV) light into at least one chamber of the plurality of chambers.

22. The apparatus of claim 2, wherein the apparatus further comprises a scrubber configured to be in fluid communication with the GC column.

23. The apparatus of claim 1, wherein the apparatus further comprises at least one 3D printed structure disposed on at least one of the at least four abutting planar layers of flexible flat glass.

* * * * *